US010213311B2

(12) United States Patent
Mahfouz

(10) Patent No.: US 10,213,311 B2
(45) Date of Patent: *Feb. 26, 2019

(54) DEFORMABLE ARTICULATING TEMPLATES

(71) Applicant: ZIMMER, INC., Warsaw, IN (US)

(72) Inventor: Mohamed Rashwan Mahfouz, Knoxville, TN (US)

(73) Assignee: ZIMMER INC., Warsaw, IN (US)

(*) Notice: Subject to any disclaimer, the term of this patent is extended or adjusted under 35 U.S.C. 154(b) by 31 days.

This patent is subject to a terminal disclaimer.

(21) Appl. No.: 15/264,488

(22) Filed: Sep. 13, 2016

(65) Prior Publication Data
US 2017/0000615 A1 Jan. 5, 2017

Related U.S. Application Data

(60) Continuation of application No. 14/640,082, filed on Mar. 6, 2015, now Pat. No. 9,675,461, which is a division of application No. 13/203,012, filed as application No. PCT/US2010/025466 on Feb. 25, 2010, now Pat. No. 8,989,460.

(60) Provisional application No. 61/208,509, filed on Feb. 25, 2009, provisional application No. 61/222,560, filed on Jul. 2, 2009.

(51) Int. Cl.
A61F 2/30 (2006.01)
G06T 19/00 (2011.01)
A61F 2/38 (2006.01)
G06F 17/18 (2006.01)
A61B 8/00 (2006.01)
A61B 34/10 (2016.01)
A61F 2/36 (2006.01)
A61F 2/40 (2006.01)
G16H 50/50 (2018.01)
G06F 19/00 (2018.01)
G06K 9/00 (2006.01)

(52) U.S. Cl.
CPC ........ A61F 2/30942 (2013.01); A61B 8/4245 (2013.01); A61B 34/10 (2016.02); A61F 2/3094 (2013.01); A61F 2/3601 (2013.01); A61F 2/389 (2013.01); A61F 2/3859 (2013.01); A61F 2/4003 (2013.01); G06F 17/18 (2013.01); G06F 19/00 (2013.01); G06T 19/00 (2013.01); G16H 50/50 (2018.01); A61B 2034/102 (2016.02); A61B 2034/108 (2016.02); A61F 2/38 (2013.01); A61F 2002/30943 (2013.01); A61F 2002/30948 (2013.01); A61F 2002/3863 (2013.01); A61F 2002/3895 (2013.01); G06K 9/00 (2013.01); G06T 2210/41 (2013.01)

(58) Field of Classification Search
CPC ..... G06T 7/0012; G06T 7/0014; G06T 19/20; G06T 2207/30008; G06T 2207/30052; A61F 2/30; A61F 2002/30199; A61F 2/3094; A61F 2/30942; A61F 2002/30943; A61F 2002/30948; A61F 2002/30963; A61B 2034/102; A61B 2034/108

See application file for complete search history.

(56) References Cited

U.S. PATENT DOCUMENTS

| 4,841,975 | A | 6/1989 | Woolson | 128/653 |
|---|---|---|---|---|
| 5,098,383 | A | 3/1992 | Hemmy et al. | 604/116 |
| 5,490,854 | A | 2/1996 | Fisher et al. | 606/88 |
| 5,609,643 | A | 3/1997 | Colleran et al. | 623/20 |
| 5,768,134 | A | 6/1998 | Swaelens et al. | 364/468.28 |
| 5,871,018 | A | 2/1999 | Delp et al. | 128/898 |
| 5,916,219 | A | 6/1999 | Matsuno et al. | 606/88 |
| 6,893,467 | B1 | 5/2005 | Bercovy | 623/20.14 |
| 7,239,908 | B1 | 7/2007 | Alexander et al. | 600/427 |
| 7,269,241 | B2 | 9/2007 | Siltanen et al. | 378/4 |
| 7,357,057 | B2 | 4/2008 | Chiang | 83/614 |
| 7,468,075 | B2 | 12/2008 | Lang et al. | 623/16.11 |
| 7,510,557 | B1 | 3/2009 | Bonutti | 606/86 R |
| 7,534,263 | B2 | 5/2009 | Burdulis, Jr. et al. | 623/14.12 |
| 7,618,451 | B2 | 11/2009 | Berez et al. | 623/14.12 |
| 7,634,119 | B2 | 12/2009 | Tsougarakis et al. | 382/128 |
| 7,717,956 | B2 | 5/2010 | Lang | 623/14.12 |
| 7,796,791 | B2 | 9/2010 | Tsougarakis et al. | 382/128 |
| 7,799,077 | B2 | 9/2010 | Lang et al. | 623/14.12 |
| 7,806,896 | B1 | 10/2010 | Bonutti | 606/86 R |
| 7,806,897 | B1 | 10/2010 | Bonutti | 606/86 R |

(Continued)

FOREIGN PATENT DOCUMENTS

| AU | 2004293091 A1 | 6/2005 |
|---|---|---|
| AU | 2004293104 A1 | 6/2005 |

(Continued)

OTHER PUBLICATIONS

Taylor et al, "Computer-Integrated Surgery, Technology and Clinical Applications", The MIT Press, Cambridge, MA, London, UK, pp. 451-463, 1995.

(Continued)

Primary Examiner — Andrew W Johns
(74) Attorney, Agent, or Firm — Norton Rose Fulbright Canada LLP

(57) ABSTRACT

A system for generating a patient-specific implant is described which includes a means for generating a three dimensional electronic representation of a human anatomical feature including size and curvature features matching the human anatomical feature, a means for selecting a prosthetic implant template from a database of prosthetic implant templates, the database being formed of the prosthetic implant templates by a means for generating a series of the virtual implant templates, a means for designing the patient-specific implant to imitate the size and curvature features based at least in part on the selected prosthetic implant template, and a means for virtually testing fit of the patient-specific implant using the three dimensional electronic representation of the human anatomical feature.

24 Claims, 56 Drawing Sheets

(56) References Cited

U.S. PATENT DOCUMENTS

| | | | |
|---|---|---|---|
| 7,967,868 B2 | 6/2011 | White et al. | 623/20.35 |
| 7,981,158 B2 | 7/2011 | Fitz et al. | 623/17.16 |
| 8,062,302 B2 | 11/2011 | Lang et al. | 606/87 |
| 8,066,708 B2 | 11/2011 | Lang et al. | 606/87 |
| 8,070,752 B2 | 12/2011 | Metzger et al. | 606/88 |
| 8,077,950 B2 | 12/2011 | Tsougarakis et al. | 382/128 |
| 8,083,745 B2 | 12/2011 | Lang et al. | 606/87 |
| 8,092,465 B2 | 1/2012 | Metzger et al. | 606/96 |
| 8,094,900 B2 | 1/2012 | Steines et al. | 382/128 |
| 8,105,330 B2 | 1/2012 | Fitz et al. | 606/88 |
| 8,122,582 B2 | 2/2012 | Burdulis, Jr. et al. | 29/527.1 |
| 8,133,234 B2 | 3/2012 | Meridew et al. | 606/91 |
| 8,160,345 B2 | 4/2012 | Pavlovskaia et al. | 382/131 |
| 8,175,683 B2 | 5/2012 | Roose | 600/427 |
| 8,221,430 B2 | 7/2012 | Park et al. | 606/88 |
| 8,234,097 B2 | 7/2012 | Steines et al. | 703/1 |
| 8,241,293 B2 | 8/2012 | Stone et al. | 606/87 |
| 8,282,646 B2 | 10/2012 | Schoenefeld et al. | 606/88 |
| 8,298,237 B2 | 10/2012 | Schoenefeld et al. | 606/87 |
| 8,337,501 B2 | 12/2012 | Fitz et al. | 606/86 R |
| 8,337,507 B2 | 12/2012 | Lang et al. | 606/102 |
| 8,343,218 B2 | 1/2013 | Lang et al. | 623/16.11 |
| 8,366,771 B2 | 2/2013 | Burdulis, Jr. et al. | 623/14.12 |
| 8,377,129 B2 | 2/2013 | Fitz et al. | 623/14.12 |
| 8,439,926 B2 | 5/2013 | Bojarski et al. | 606/88 |
| 8,460,304 B2 | 6/2013 | Fitz et al. | 606/88 |
| 8,480,754 B2 | 7/2013 | Bojarski et al. | 623/20.35 |
| 8,500,740 B2 | 8/2013 | Bojarski et al. | 606/86 R |
| 8,529,568 B2 | 9/2013 | Bouadi | 606/84 |
| 8,529,630 B2 | 9/2013 | Bojarski et al. | 623/20.14 |
| 8,545,569 B2 | 10/2013 | Fitz et al. | 623/20.14 |
| 8,551,099 B2 | 10/2013 | Lang et al. | 606/86 R |
| 8,551,102 B2 | 10/2013 | Fitz et al. | 606/88 |
| 8,551,103 B2 | 10/2013 | Fitz et al. | 606/88 |
| 8,551,169 B2 | 10/2013 | Fitz et al. | 623/14.12 |
| 8,556,906 B2 | 10/2013 | Fitz et al. | 606/87 |
| 8,556,907 B2 | 10/2013 | Fitz et al. | 606/87 |
| 8,556,971 B2 | 10/2013 | Lang | 623/14.12 |
| 8,556,983 B2 | 10/2013 | Bojarski et al. | 623/20.35 |
| 8,561,278 B2 | 10/2013 | Fitz et al. | 29/407.09 |
| 8,562,611 B2 | 10/2013 | Fitz et al. | 606/80 |
| 8,562,618 B2 | 10/2013 | Fitz et al. | 606/88 |
| 8,568,479 B2 | 10/2013 | Fitz et al. | 623/14.12 |
| 8,568,480 B2 | 10/2013 | Fitz et al. | 623/14.12 |
| 8,585,708 B2 | 11/2013 | Fitz et al. | 606/88 |
| 8,617,172 B2 | 12/2013 | Fitz et al. | 606/88 |
| 8,617,242 B2 | 12/2013 | Philipp | 623/16.11 |
| 8,623,026 B2 | 1/2014 | Wong et al. | 606/96 |
| 8,634,617 B2 | 1/2014 | Tsougarakis et al. | 382/128 |
| 8,638,998 B2 | 1/2014 | Steines et al. | 382/128 |
| 8,641,716 B2 | 2/2014 | Fitz et al. | 606/80 |
| 8,657,827 B2 | 2/2014 | Fitz et al. | 606/87 |
| 8,682,052 B2 | 3/2014 | Fitz et al. | 382/131 |
| 8,989,460 B2 * | 3/2015 | Mahfouz | A61F 2/3094 382/128 |
| 9,895,230 B2 * | 2/2018 | Mahfouz | A61F 2/3094 |
| 2002/0055692 A1 | 5/2002 | Tanaka et al. | 600/587 |
| 2003/0040806 A1 | 2/2003 | MacDonald | 623/23.49 |
| 2003/0055502 A1 | 3/2003 | Lang et al. | 623/16.11 |
| 2003/0181831 A1 | 9/2003 | Tanaka et al. | 600/587 |
| 2003/0216669 A1 | 11/2003 | Lang et al. | 600/587 |
| 2004/0039259 A1 | 2/2004 | Krause et al. | 600/300 |
| 2004/0068187 A1 | 4/2004 | Krause et al. | 600/443 |
| 2004/0098132 A1 | 5/2004 | Andriacchi et al. | 623/20.35 |
| 2004/0133276 A1 | 7/2004 | Lang et al. | 623/14.12 |
| 2004/0138754 A1 | 7/2004 | Lang et al. | 623/20.14 |
| 2004/0147927 A1 | 7/2004 | Tsougarakis et al. | 606/83 |
| 2004/0153079 A1 | 8/2004 | Tsougarakis et al. | 606/77 |
| 2004/0204644 A1 | 10/2004 | Tsougarakis et al. | 600/410 |
| 2004/0204760 A1 | 10/2004 | Fitz et al. | 623/14.12 |
| 2004/0236424 A1 | 11/2004 | Berez et al. | 623/14.12 |
| 2005/0010444 A1 | 1/2005 | Iliff | 705/2 |
| 2005/0197709 A1 | 9/2005 | Schaefer et al. | 623/20.3 |
| 2005/0197814 A1 | 9/2005 | Aram et al. | 703/11 |
| 2005/0234461 A1 | 10/2005 | Burdulis, Jr. et al. | 606/79 |
| 2005/0267584 A1 | 12/2005 | Burdulis, Jr. et al. | 623/20.19 |
| 2006/0111722 A1 | 5/2006 | Bouadi | 606/79 |
| 2006/0195198 A1 | 8/2006 | James | 700/1 |
| 2007/0081706 A1 | 4/2007 | Zhou et al. | 382/128 |
| 2007/0083266 A1 | 4/2007 | Lang | 623/17.11 |
| 2007/0100462 A1 | 5/2007 | Lang et al. | 623/20.29 |
| 2007/0113243 A1 | 5/2007 | Schroeder et al. | 700/118 |
| 2007/0156171 A1 | 7/2007 | Lang et al. | 606/205 |
| 2007/0157783 A1 | 7/2007 | Chiang | 88/485 |
| 2007/0168225 A1 | 7/2007 | Haider et al. | 705/2 |
| 2007/0179626 A1 | 8/2007 | De La Barrera et al. | 623/20.14 |
| 2007/0198022 A1 | 8/2007 | Lang et al. | 606/88 |
| 2007/0226986 A1 | 10/2007 | Park et al. | 29/592 |
| 2007/0233141 A1 | 10/2007 | Park et al. | 606/88 |
| 2007/0233269 A1 | 10/2007 | Steines et al. | 623/20.21 |
| 2007/0250169 A1 | 10/2007 | Lang | 623/17.12 |
| 2007/0255288 A1 | 11/2007 | Mahfouz et al. | 606/102 |
| 2007/0276214 A1 | 11/2007 | Dachille et al. | 600/407 |
| 2008/0058945 A1 | 3/2008 | Hajaj et al. | 623/20.14 |
| 2008/0097187 A1 | 4/2008 | Gielen et al. | 600/409 |
| 2008/0114370 A1 | 5/2008 | Schoenefeld | 606/96 |
| 2008/0147072 A1 | 6/2008 | Park et al. | 606/87 |
| 2008/0161815 A1 | 7/2008 | Schoenefeld et al. | 606/87 |
| 2008/0172125 A1 | 7/2008 | Ek | 623/14.12 |
| 2008/0195216 A1 | 8/2008 | Philipp | 623/18.11 |
| 2008/0243127 A1 | 10/2008 | Lang et al. | 606/87 |
| 2008/0275452 A1 | 11/2008 | Lang et al. | 606/88 |
| 2008/0281328 A1 | 11/2008 | Lang et al. | 606/87 |
| 2008/0281329 A1 | 11/2008 | Fitz et al. | 606/88 |
| 2008/0281426 A1 | 11/2008 | Fitz et al. | 623/17.16 |
| 2008/0287954 A1 | 11/2008 | Kunz et al. | 606/87 |
| 2009/0024131 A1 | 1/2009 | Metzger et al. | 606/88 |
| 2009/0043556 A1 | 2/2009 | Axelson et al. | 703/11 |
| 2009/0088753 A1 | 4/2009 | Aram et al. | 606/79 |
| 2009/0088754 A1 | 4/2009 | Aker et al. | 606/79 |
| 2009/0088755 A1 | 4/2009 | Aker et al. | 606/79 |
| 2009/0088758 A1 | 4/2009 | Bennett | 606/82 |
| 2009/0088759 A1 | 4/2009 | Aram et al. | 606/87 |
| 2009/0088760 A1 | 4/2009 | Aram et al. | 606/87 |
| 2009/0088761 A1 | 4/2009 | Roose et al. | 606/87 |
| 2009/0088763 A1 | 4/2009 | Aram et al. | 606/88 |
| 2009/0093816 A1 | 4/2009 | Roose et al. | 606/87 |
| 2009/0099567 A1 | 4/2009 | Zajac | 606/79 |
| 2009/0110498 A1 | 4/2009 | Park | 408/1 R |
| 2009/0131941 A1 | 5/2009 | Park et al. | 606/87 |
| 2009/0131942 A1 | 5/2009 | Aker et al. | 606/88 |
| 2009/0138020 A1 | 5/2009 | Park et al. | 606/88 |
| 2009/0157083 A1 | 6/2009 | Park et al. | 606/88 |
| 2009/0222014 A1 | 9/2009 | Bojarksi et al. | 606/88 |
| 2009/0222016 A1 | 9/2009 | Park et al. | 606/89 |
| 2009/0222103 A1 | 9/2009 | Fitz et al. | 623/18.11 |
| 2009/0226068 A1 | 9/2009 | Fitz et al. | 382/131 |
| 2009/0228113 A1 | 9/2009 | Lang et al. | 623/20.32 |
| 2009/0254093 A1 | 10/2009 | White et al. | 606/89 |
| 2009/0270868 A1 | 10/2009 | Park et al. | 606/87 |
| 2009/0276045 A1 | 11/2009 | Lang | 623/14.12 |
| 2009/0306676 A1 | 12/2009 | Lang et al. | 606/102 |
| 2009/0307893 A1 | 12/2009 | Burdulis, Jr. et al. | 29/527.1 |
| 2009/0312805 A1 | 12/2009 | Lang et al. | 606/86 R |
| 2010/0023015 A1 | 1/2010 | Park | 606/87 |
| 2010/0042105 A1 | 2/2010 | Park et al. | 606/87 |
| 2010/0049195 A1 | 2/2010 | Park et al. | 606/87 |
| 2010/0054572 A1 | 3/2010 | Tsougarakis et al. | 382/131 |
| 2010/0082035 A1 | 4/2010 | Keefer | 606/91 |
| 2010/0087829 A1 | 4/2010 | Metzger et al. | 606/96 |
| 2010/0152741 A1 | 6/2010 | Park et al. | 606/89 |
| 2010/0152782 A1 | 6/2010 | Stone et al. | 606/280 |
| 2010/0160917 A1 | 6/2010 | Fitz et al. | 606/88 |
| 2010/0168754 A1 | 7/2010 | Fitz et al. | 606/88 |
| 2010/0174376 A1 | 7/2010 | Lang | 623/18.11 |
| 2010/0185202 A1 | 7/2010 | Lester et al. | 606/88 |
| 2010/0191244 A1 | 7/2010 | White et al. | 606/88 |
| 2010/0212138 A1 | 8/2010 | Carroll et al. | 29/446 |
| 2010/0217270 A1 | 8/2010 | Polinski et al. | 606/87 |
| 2010/0217338 A1 | 8/2010 | Carroll et al. | 606/86 R |
| 2010/0228257 A1 | 9/2010 | Bonutti | 606/87 |
| 2010/0234849 A1 | 9/2010 | Bouadi | 606/84 |
| 2010/0256479 A1 | 10/2010 | Park et al. | 600/410 |

(56) References Cited

U.S. PATENT DOCUMENTS

| | | |
|---|---|---|
| 2010/0262150 A1 | 10/2010 | Lian ........................ 606/87 |
| 2010/0274534 A1 | 10/2010 | Steines et al. ................ 703/1 |
| 2010/0281678 A1 | 11/2010 | Burdulis, Jr. et al. ........ 29/592 |
| 2010/0286700 A1 | 11/2010 | Snider et al. ................. 606/89 |
| 2010/0298894 A1 | 11/2010 | Bojarski et al. .......... 606/86 R |
| 2010/0298946 A1 | 11/2010 | Sun et al. ................. 623/20.24 |
| 2010/0303313 A1 | 12/2010 | Lang et al. .................. 382/128 |
| 2010/0303317 A1 | 12/2010 | Tsougarakis et al. ........ 382/128 |
| 2010/0303324 A1 | 12/2010 | Lang et al. .................. 382/131 |
| 2010/0305573 A1 | 12/2010 | Fitz et al. ..................... 606/87 |
| 2010/0305574 A1 | 12/2010 | Fitz et al. ..................... 606/88 |
| 2010/0305708 A1 | 12/2010 | Lang et al. ................ 623/20.18 |
| 2010/0305907 A1 | 12/2010 | Fitz et al. ........................ 703/1 |
| 2010/0329530 A1 | 12/2010 | Lang et al. .................. 382/131 |
| 2011/0015636 A1 | 1/2011 | Katrana et al. ................ 606/87 |
| 2011/0015637 A1 | 1/2011 | De Smedt et al. ............ 606/89 |
| 2011/0015639 A1 | 1/2011 | Metzger et al. ............... 606/91 |
| 2011/0022179 A1 | 1/2011 | Andriacchi et al. ....... 623/20.18 |
| 2011/0029091 A1 | 2/2011 | Bojarski et al. ........... 623/20.32 |
| 2011/0029093 A1 | 2/2011 | Bojarski et al. ........... 623/20.35 |
| 2011/0040168 A1 | 2/2011 | Arnaud et al. ............... 600/407 |
| 2011/0054478 A1 | 3/2011 | Vanasse et al. ................ 606/87 |
| 2011/0060341 A1 | 3/2011 | Angibaud et al. ............. 606/89 |
| 2011/0066193 A1 | 3/2011 | Lang et al. ............... 606/86 R |
| 2011/0066245 A1 | 3/2011 | Lang et al. ................ 623/18.11 |
| 2011/0071533 A1 | 3/2011 | Metzger et al. ............... 606/88 |
| 2011/0071581 A1 | 3/2011 | Lang et al. ............... 606/89 R |
| 2011/0071645 A1 | 3/2011 | Bojarski et al. ........... 623/20.35 |
| 2011/0071802 A1 | 3/2011 | Bojarski et al. .................. 703/1 |
| 2011/0087332 A1 | 4/2011 | Bojarski et al. ........... 623/20.32 |
| 2011/0092977 A1 | 4/2011 | Salehi et al. ................... 606/87 |
| 2011/0093108 A1 | 4/2011 | Ashby et al. ................. 700/103 |
| 2011/0106093 A1 | 5/2011 | Romano et al. ............... 606/88 |
| 2011/0125275 A1 | 5/2011 | Lipman et al. ............ 623/20.11 |
| 2011/0144760 A1 | 6/2011 | Wong et al. ............... 623/20.14 |
| 2011/0153026 A1 | 6/2011 | Heggendorn et al. ..... 623/20.35 |
| 2011/0160736 A1 | 6/2011 | Meridew et al. ............... 606/89 |
| 2011/0160867 A1 | 6/2011 | Meridew et al. .......... 623/20.36 |
| 2011/0166578 A1 | 7/2011 | Stone et al. ................... 606/88 |
| 2011/0172672 A1 | 7/2011 | Dubeau et al. ................ 606/87 |
| 2011/0184419 A1 | 7/2011 | Meridew et al. ............... 606/80 |
| 2011/0196377 A1 | 8/2011 | Hodorek et al. ............... 606/87 |
| 2011/0213368 A1 | 9/2011 | Fitz et al. ...................... 606/80 |
| 2011/0213373 A1 | 9/2011 | Fitz et al. ...................... 606/87 |
| 2011/0213374 A1 | 9/2011 | Fitz et al. ...................... 606/87 |
| 2011/0213376 A1 | 9/2011 | Maxson et al. ................ 606/88 |
| 2011/0213377 A1 | 9/2011 | Lang et al. .................... 606/89 |
| 2011/0213427 A1 | 9/2011 | Fitz et al. ................... 606/86 R |
| 2011/0213428 A1 | 9/2011 | Fitz et al. ................... 606/86 R |
| 2011/0213429 A1 | 9/2011 | Lang et al. ................ 606/86 R |
| 2011/0213430 A1 | 9/2011 | Lang et al. ................ 606/86 R |
| 2011/0213431 A1 | 9/2011 | Fitz et al. ................... 606/86 R |
| 2011/0214279 A1 | 9/2011 | Park et al. ...................... 29/592 |
| 2011/0218539 A1 | 9/2011 | Fitz et al. ...................... 606/87 |
| 2011/0218545 A1 | 9/2011 | Catanzarite et al. ........... 606/96 |
| 2011/0218584 A1 | 9/2011 | Fitz et al. ................... 606/86 R |
| 2011/0224674 A1 | 9/2011 | White et al. ................... 606/91 |
| 2011/0230888 A1 | 9/2011 | Lang et al. .................... 606/87 |
| 2011/0238073 A1 | 9/2011 | Lang et al. .................... 606/89 |
| 2011/0245835 A1 | 10/2011 | Dodds et al. ................. 606/87 |
| 2011/0266265 A1 | 11/2011 | Lang ........................ 219/121.72 |
| 2011/0295329 A1 | 12/2011 | Fitz et al. ................... 606/86 R |
| 2011/0295378 A1 | 12/2011 | Bojarski et al. ........... 623/20.35 |
| 2011/0313423 A1 | 12/2011 | Lang et al. .................... 606/87 |
| 2011/0313424 A1 | 12/2011 | Bono et al. .................... 606/91 |
| 2011/0319897 A1 | 12/2011 | Lang et al. .................... 606/79 |
| 2011/0319900 A1 | 12/2011 | Lang et al. .................... 606/87 |
| 2012/0010711 A1 | 1/2012 | Antonyshyn et al. ..... 623/16.11 |
| 2012/0029520 A1 | 2/2012 | Lang et al. .................... 606/89 |
| 2012/0041445 A1 | 2/2012 | Roose et al. ................... 606/96 |
| 2012/0041446 A1 | 2/2012 | Wong et al. ................... 606/96 |
| 2012/0065640 A1 | 3/2012 | Metzger et al. ............... 606/88 |
| 2012/0066892 A1 | 3/2012 | Lang et al. .................... 29/592 |
| 2012/0071881 A1 | 3/2012 | Lang et al. .................... 606/87 |
| 2012/0071882 A1 | 3/2012 | Lang et al. .................... 606/88 |
| 2012/0071883 A1 | 3/2012 | Lang et al. .................... 606/88 |
| 2012/0072185 A1 | 3/2012 | Lang et al. ....................... 703/1 |
| 2012/0078254 A1 | 3/2012 | Ashby et al. .................. 606/79 |
| 2012/0078258 A1 | 3/2012 | Lo et al. ........................ 606/87 |
| 2012/0078259 A1 | 3/2012 | Meridew ....................... 606/87 |
| 2012/0093377 A1 | 4/2012 | Tsougarakis et al. ........ 382/128 |
| 2012/0101503 A1 | 4/2012 | Lang et al. .................... 606/87 |
| 2012/0109138 A1 | 5/2012 | Meridew et al. ............... 606/91 |
| 2012/0116203 A1 | 5/2012 | Vancraen et al. ............. 600/407 |
| 2012/0116562 A1 | 5/2012 | Agnihotri et al. ............. 700/98 |
| 2012/0123422 A1 | 5/2012 | Agnihotri et al. ............. 606/89 |
| 2012/0123423 A1 | 5/2012 | Fryman ......................... 606/89 |
| 2012/0130382 A1 | 5/2012 | Iannotti et al. ................ 606/87 |
| 2012/0130687 A1 | 5/2012 | Otto et al. ........................ 703/1 |
| 2012/0141034 A1 | 6/2012 | Iannotti et al. ............... 382/199 |
| 2012/0143197 A1 | 6/2012 | Lang et al. .................... 606/87 |
| 2012/0151730 A1 | 6/2012 | Fitz et al. .................. 29/407.01 |
| 2012/0158001 A1 | 6/2012 | Burdulis, Jr. et al. .......... 606/88 |
| 2012/0165820 A1 | 6/2012 | De Smedt et al. ............. 606/87 |
| 2012/0172884 A1 | 7/2012 | Zheng et al. ................... 606/91 |
| 2012/0191205 A1 | 7/2012 | Bojarski et al. ............. 623/20.32 |
| 2012/0191420 A1 | 7/2012 | Bojarski et al. .................. 703/1 |
| 2012/0192401 A1 | 8/2012 | Pavlovskaia et al. ........... 29/428 |
| 2012/0197260 A1 | 8/2012 | Fitz et al. ...................... 606/88 |
| 2012/0197408 A1 | 8/2012 | Lang et al. ................. 623/18.11 |
| 2012/0201440 A1 | 8/2012 | Steines et al. ................ 382/131 |
| 2012/0209276 A1 | 8/2012 | Schuster ........................ 606/88 |
| 2012/0209394 A1 | 8/2012 | Bojarski et al. ............ 623/30.32 |
| 2012/0215226 A1 | 8/2012 | Bonutti ......................... 606/87 |
| 2012/0221008 A1 | 8/2012 | Carroll et al. ................. 606/87 |
| 2012/0226283 A1 | 9/2012 | Meridew et al. ............... 606/81 |
| 2012/0232669 A1 | 9/2012 | Bojarski et al. ............... 623/20.3 |
| 2012/0232670 A1 | 9/2012 | Bojarski et al. ........... 623/20.35 |
| 2012/0232671 A1 | 9/2012 | Bojarski ..................... 623/20.35 |
| 2012/0239045 A1 | 9/2012 | Li .................................. 606/88 |
| 2012/0245647 A1 | 9/2012 | Kunz et al. ................. 606/86 R |
| 2012/0245699 A1 | 9/2012 | Lang et al. ................... 623/20.3 |
| 2012/0265208 A1 | 10/2012 | Smith ............................ 606/87 |
| 2012/0271366 A1 | 10/2012 | Katrana et al. ............. 606/86 R |
| 2012/0276509 A1 | 11/2012 | Iannotti et al. ............... 434/267 |
| 2012/0277751 A1 | 11/2012 | Catanzarite et al. ........... 606/88 |
| 2012/0289966 A1 | 11/2012 | Fitz et al. ...................... 606/88 |
| 2012/0296337 A1 | 11/2012 | Fitz et al. ...................... 606/80 |
| 2013/0018379 A1 | 1/2013 | Fitz et al. ...................... 606/87 |
| 2013/0018380 A1 | 1/2013 | Fitz et al. ...................... 606/88 |
| 2013/0018464 A1 | 1/2013 | Fitz et al. ................... 623/14.12 |
| 2013/0023884 A1 | 1/2013 | Fitz et al. ...................... 606/88 |
| 2013/0024000 A1 | 1/2013 | Bojarski et al. ............ 623/20.14 |
| 2013/0030419 A1 | 1/2013 | Fitz et al. ........................ 606/1 |
| 2013/0030441 A1 | 1/2013 | Fitz et al. ...................... 606/87 |
| 2013/0079781 A1 | 3/2013 | Fitz et al. .......... A61B 17/1675 |
| 2013/0079876 A1 | 3/2013 | Fitz et al. .......... A61F 2/30756 |
| 2013/0081247 A1 | 4/2013 | Fitz et al. ............... B23Q 17/00 |
| 2013/0096562 A1 | 4/2013 | Fitz et al. ........... A61B 17/1764 |
| 2013/0103363 A1 | 4/2013 | Lang et al. ............. G06F 17/50 |
| 2013/0110471 A1 | 5/2013 | Lang et al. ............. G06F 17/50 |
| 2013/0123792 A1 | 5/2013 | Fitz et al. ............ A16B 17/1739 |
| 2013/0184713 A1 | 7/2013 | Bojarski et al. ...... A61B 17/154 |
| 2013/0197870 A1 | 8/2013 | Steines et al. .......... G06F 17/50 |
| 2013/0211409 A1 | 8/2013 | Burdulis, Jr. et al. ........................ A61B 17/158 |
| 2013/0211410 A1 | 8/2013 | Landes et al. ...... A61B 17/1767 |
| 2013/0211531 A1 | 8/2013 | Steines et al. ........ A61F 2/3859 |
| 2013/0245803 A1 | 9/2013 | Lang ...................... G06F 17/50 |
| 2013/0253522 A1 | 9/2013 | Bojarski et al. ... A61B 17/1764 |
| 2013/0289570 A1 | 10/2013 | Chao .................. A61B 17/157 |
| 2013/0296874 A1 | 11/2013 | Chao .................. A61B 17/157 |
| 2013/0297031 A1 | 11/2013 | Hafez ................. A61F 2/30942 |
| 2013/0317511 A1 | 11/2013 | Bojarski et al. ....... A61B 19/50 |
| 2013/0331850 A1 | 12/2013 | Bojarski et al. ....... A61F 2/4657 |
| 2014/0005792 A1 | 1/2014 | Lang et al. .......... A61F 2/30942 |
| 2014/0029814 A1 | 1/2014 | Fitz et al. ............... G06T 7/0014 |
| 2014/0031826 A1 | 1/2014 | Bojarski et al. ........ A61B 17/17 |
| 2014/0039631 A1 | 2/2014 | Bojarski et al. ........... A61F 2/30 |
| 2014/0058396 A1 | 2/2014 | Fitz et al. ............ A61B 17/1739 |
| 2014/0058397 A1 | 2/2014 | Fitz et al. ............ A61B 17/1764 |
| 2014/0066935 A1 | 3/2014 | Fitz et al. ............ A61B 17/1739 |

(56) References Cited

U.S. PATENT DOCUMENTS

| | | | |
|---|---|---|---|
| 2014/0066936 A1 | 3/2014 | Fitz et al. | A61B 17/1682 |
| 2014/0074441 A1 | 3/2014 | Fitz et al. | A61B 17/1739 |
| 2014/0086780 A1 | 3/2014 | Miller et al. | A61F 5/01 |

FOREIGN PATENT DOCUMENTS

| | | | |
|---|---|---|---|
| AU | 2005309692 A1 | 6/2006 | A61F 2/38 |
| AU | 2005311558 A1 | 6/2006 | A61B 17/17 |
| AU | 2002310193 B2 | 3/2007 | A61L 27/00 |
| AU | 2006297137 A1 | 4/2007 | A61F 2/38 |
| AU | 2002310193 B8 | 5/2007 | A61L 27/00 |
| AU | 2007202573 A1 | 6/2007 | A61L 27/00 |
| AU | 2007212033 A1 | 8/2007 | A61B 17/15 |
| AU | 2007226924 A1 | 9/2007 | A61F 2/30 |
| AU | 2009221773 A1 | 9/2009 | A61F 2/38 |
| AU | 2009246474 A1 | 11/2009 | A61F 2/30 |
| AU | 2010201200 A1 | 4/2010 | A61F 2/30 |
| AU | 2011203237 A1 | 7/2011 | A61F 2/38 |
| AU | 2010217903 A1 | 9/2011 | A61F 2/30 |
| AU | 2010236263 A1 | 11/2011 | A61B 17/90 |
| AU | 2010264466 A1 | 2/2012 | A61F 2/38 |
| AU | 2010289706 A1 | 3/2012 | A61F 2/38 |
| AU | 2010315099 A1 | 5/2012 | A61B 5/103 |
| AU | 2010327987 A1 | 6/2012 | A61B 17/68 |
| AU | 2011203237 B2 | 6/2012 | A61F 2/08 |
| AU | 2012216829 A1 | 10/2012 | A61F 2/08 |
| AU | 2012217654 A1 | 10/2013 | |
| AU | 2007212033 B2 | 1/2014 | A61B 17/15 |
| AU | 2014200073 A1 | 1/2014 | A61B 17/15 |
| AU | 2012289973 A1 | 3/2014 | A61F 2/30 |
| AU | 2012296556 A1 | 3/2014 | A61F 2/38 |
| CA | 2501041 A1 | 4/2004 | A61F 2/30 |
| CA | 2505371 A1 | 5/2004 | A61F 2/30 |
| CA | 2505419 A1 | 6/2004 | G06T 7/00 |
| CA | 2506849 A1 | 6/2004 | G06T 7/00 |
| CA | 2546958 A1 | 6/2005 | A61F 2/08 |
| CA | 2546965 A1 | 6/2005 | A61F 2/08 |
| CA | 2804883 A1 | 6/2005 | A61F 2/30 |
| CA | 2588907 A1 | 6/2006 | A61B 17/15 |
| CA | 2590534 A1 | 6/2006 | A61F 2/38 |
| CA | 2623834 A1 | 4/2007 | A61F 2/38 |
| CA | 2641241 A1 | 8/2007 | A61B 17/15 |
| CA | 2646288 A1 | 9/2007 | A61F 2/30 |
| CA | 2717760 A1 | 9/2009 | A61F 2/38 |
| CA | 2765499 A1 | 12/2010 | A61F 2/38 |
| CA | 2771573 A1 | 3/2011 | A61F 2/38 |
| CA | 2779283 A1 | 5/2011 | A61F 2/38 |
| CA | 2782137 A1 | 6/2011 | A61F 2/38 |
| CA | 2546965 C | 3/2013 | A61F 2/08 |
| CN | 1728976 A | 2/2006 | A61F 2/30 |
| CN | 1729483 A | 2/2006 | G06T 7/00 |
| CN | 1729484 A | 2/2006 | G06T 7/00 |
| CN | 1913844 A | 2/2007 | A61F 2/08 |
| CN | 101111197 A | 1/2008 | A61B 17/17 |
| CN | 101384230 A | 3/2009 | A61F 2/30 |
| CN | 101442960 A | 5/2009 | A61F 2/38 |
| CN | 100502808 C | 6/2009 | A61F 2/30 |
| CN | 102006841 A | 4/2011 | A61F 2/38 |
| CN | 102125448 A | 7/2011 | A61B 17/00 |
| CN | 102405032 A | 4/2012 | A61F 2/30 |
| CN | 102448394 A | 5/2012 | A61B 17/90 |
| CN | 101420911 B | 7/2012 | A61B 17/15 |
| CN | 102599960 A | 7/2012 | A61B 17/16 |
| CN | 1913844 B | 9/2012 | A61B 17/15 |
| CN | 102711670 A | 10/2012 | A61F 2/38 |
| CN | 102724934 A | 10/2012 | A61F 2/38 |
| CN | 102805677 A | 12/2012 | A61F 2/38 |
| CN | 1729483 B | 10/2013 | G06T 7/00 |
| CN | 103476363 A | 12/2013 | A61F 2/30 |
| DE | 60336002 | 3/2011 | A61F 2/30 |
| DE | 60239674 | 5/2011 | A61F 2/38 |
| DE | 602004032166 | 5/2011 | A61F 2/44 |
| DE | 602005027391 | 5/2011 | A61B 17/17 |
| EP | 1555962 | 4/2004 | A61F 2/30 |
| EP | 1558181 | 5/2004 | A61F 2/30 |
| EP | 1567985 | 6/2004 | G01R 33/56 |
| EP | 1575460 | 6/2004 | A61F 2/46 |
| EP | 1686930 | 6/2005 | A61F 2/08 |
| EP | 1814491 | 6/2006 | A61F 2/38 |
| EP | 1833387 | 6/2006 | A61B 17/17 |
| EP | 1686931 A1 | 8/2006 | A61F 2/08 |
| EP | 1951136 | 5/2007 | A61B 17/88 |
| EP | 1981409 | 8/2007 | |
| EP | 1996121 | 9/2007 | A61F 2/30 |
| EP | 1928359 A2 | 6/2008 | A61F 2/38 |
| EP | 2114312 | 8/2008 | A61F 2/38 |
| EP | 2124764 | 9/2008 | A61B 17/15 |
| EP | 2259753 | 9/2009 | A61F 2/38 |
| EP | 2265199 | 9/2009 | A61B 17/58 |
| EP | 2303193 | 11/2009 | A61F 2/30 |
| EP | 2403434 | 9/2010 | A61F 2/30 |
| EP | 2405865 | 9/2010 | A61F 2/38 |
| EP | 2419035 | 10/2010 | A61B 17/90 |
| EP | 2445451 | 12/2010 | A61F 2/38 |
| EP | 1555962 B1 | 2/2011 | A61F 2/30 |
| EP | 2292188 A2 | 3/2011 | A61F 2/46 |
| EP | 2292189 A2 | 3/2011 | A61F 2/46 |
| EP | 2470126 | 3/2011 | A61F 2/38 |
| EP | 1389980 B1 | 4/2011 | A61F 2/30 |
| EP | 1686930 B1 | 4/2011 | A61F 2/08 |
| EP | 1833387 B1 | 4/2011 | A61B 17/17 |
| EP | 2316357 A1 | 5/2011 | A61B 17/17 |
| EP | 2324799 A2 | 5/2011 | A61F 2/38 |
| EP | 2496183 | 5/2011 | A61F 2/38 |
| EP | 2335654 A1 | 6/2011 | A61F 2/38 |
| EP | 2509539 | 6/2011 | A61F 2/38 |
| EP | 2512381 | 6/2011 | A61F 2/38 |
| EP | 2292188 A3 | 5/2012 | A61F 2/46 |
| EP | 2292189 A3 | 5/2012 | A61F 2/46 |
| EP | 2324799 A3 | 1/2013 | A61F 2/38 |
| EP | 2419035 A4 | 1/2013 | A61B 17/15 |
| EP | 2591756 A1 | 5/2013 | A61F 2/38 |
| EP | 2649951 A2 | 10/2013 | A61B 17/15 |
| EP | 2671520 A3 | 12/2013 | A61B 17/15 |
| EP | 2671521 A3 | 12/2013 | A61B 17/15 |
| EP | 2671522 A3 | 12/2013 | A61B 17/15 |
| EP | 2114312 B1 | 1/2014 | A61F 2/38 |
| EP | 2710967 A2 | 3/2014 | A61B 17/15 |
| EP | 1686931 B1 | 2/2015 | A61F 2/38 |
| GB | 2484042 A | 3/2012 | A61F 2/38 |
| GB | 2489884 A | 10/2012 | |
| GB | 2484042 B | 3/2014 | A61F 2/38 |
| HK | 1059882 A1 | 8/2011 | A61F 2/30 |
| HK | 1072710 A1 | 8/2011 | A61F 2/30 |
| HK | 1087324 A1 | 11/2011 | A61B 17/15 |
| HK | 1104776 A1 | 11/2011 | A61B 17/15 |
| JP | 2002085435 A | 3/2002 | A61F 2/28 |
| JP | 2004202126 A | 7/2004 | A61F 2/28 |
| JP | 2006510403 A | 3/2006 | A61F 2/46 |
| JP | 2006263241 A | 10/2006 | A61B 19/00 |
| JP | 2007511470 A | 6/2007 | A61F 2/38 |
| JP | 2007514470 A | 6/2007 | A61F 2/38 |
| JP | 2011519713 A | 7/2011 | A61F 2/44 |
| JP | 2011224384 A | 11/2011 | A61F 2/30 |
| JP | 2012091033 A | 5/2012 | A61F 2/30 |
| JP | 2012518519 A | 8/2012 | A61F 2/38 |
| JP | 2012176318 A | 9/2012 | A61F 2/30 |
| JP | 5053515 B2 | 10/2012 | A61F 2/30 |
| JP | 2012187415 A | 10/2012 | A61F 2/30 |
| JP | 2012523897 A | 10/2012 | A61F 2/08 |
| JP | 5074036 B2 | 11/2012 | A61F 2/38 |
| JP | 2012531265 A | 12/2012 | A61F 2/30 |
| JP | 2013503007 A | 1/2013 | A61F 2/38 |
| JP | 5148284 B2 | 2/2013 | A61B 17/56 |
| JP | 5198069 B2 | 5/2013 | A61F 2/38 |
| JP | 2014000425 A | 1/2014 | A61F 2/30 |
| KR | 20050072500 A | 7/2005 | A61B 5/055 |
| KR | 20050084024 A | 8/2005 | A61F 2/46 |
| KR | 20120090997 A | 8/2012 | A61F 2/38 |
| KR | 20120102576 A | 9/2012 | A61F 2/38 |
| MX | 2012007140 A | 1/2013 | A61F 2/38 |
| NZ | 597261 A | 11/2013 | A61F 2/30 |
| SG | 173840 A1 | 9/2011 | A61F 2/30 |
| SG | 175229 A1 | 11/2011 | A61B 17/90 |

(56) References Cited

FOREIGN PATENT DOCUMENTS

| | | | | |
|---|---|---|---|---|
| SG | 176833 | A1 | 1/2012 | ............... A61F 2/38 |
| SG | 178836 | A1 | 4/2012 | ............... A61F 2/38 |
| SG | 193484 | A1 | 10/2013 | ............... A61F 2/30 |
| TW | 200509870 | A | 3/2005 | ............ A61B 17/15 |
| TW | 1231755 | B | 5/2005 | ............... A61F 2/30 |
| TW | 200800123 | A | 1/2008 | ............... A61F 2/30 |
| TW | 1330075 | B | 9/2010 | ............ A61B 17/15 |
| WO | 2004051301 | A3 | 12/2004 | ............... G06T 7/00 |
| WO | 2004049981 | A3 | 4/2005 | |
| WO | 2005051239 | A1 | 6/2005 | |
| WO | 2005051240 | A1 | 6/2005 | ............... A61F 2/08 |
| WO | 2006058057 | A2 | 6/2006 | ............... A61F 2/38 |
| WO | 2006060795 | A1 | 6/2006 | ............ A61B 17/17 |
| WO | 2007041375 | A2 | 4/2007 | ............... A61F 2/38 |
| WO | 2007062103 | A1 | 5/2007 | ............ A61B 17/88 |
| WO | 2007092841 | A2 | 8/2007 | ............ A61B 17/15 |
| WO | 2007092841 | A3 | 8/2007 | ............ A61B 17/15 |
| WO | 2007109467 | A1 | 9/2007 | ............... A61B 2/30 |
| WO | 2007109641 | A2 | 9/2007 | ............... A61F 2/30 |
| WO | 2007109641 | A3 | 9/2007 | ............... A61F 2/30 |
| WO | 2008101090 | A2 | 8/2008 | ............... A61F 2/38 |
| WO | 2008112996 | A1 | 9/2008 | ............ A61B 17/15 |
| WO | 2008101090 | A3 | 11/2008 | ............... A61F 2/38 |
| WO | 2008157412 | A2 | 12/2008 | ............ A61B 17/17 |
| WO | 2007041375 | A3 | 4/2009 | ............... A61F 2/38 |
| WO | 2008157412 | A3 | 4/2009 | ............ A61B 17/17 |
| WO | 2009111626 | A2 | 9/2009 | ............... G06K 9/00 |
| WO | 2009111639 | A1 | 9/2009 | ............ A61B 17/58 |
| WO | 2009111656 | A1 | 9/2009 | ............... A61F 2/38 |
| WO | 2009140294 | A1 | 11/2009 | ............... A61F 2/30 |
| WO | 2010099231 | A2 | 9/2010 | ............... A61F 2/38 |
| WO | 2010099231 | A3 | 9/2010 | ............... A61F 2/38 |
| WO | 2010099353 | A1 | 9/2010 | ............... A61F 2/30 |
| WO | 2010099359 | A1 | 9/2010 | ............... A61F 2/00 |
| WO | 2010121147 | A1 | 10/2010 | ............ A61B 17/90 |
| WO | 2011028624 | A1 | 3/2011 | ............... A61F 2/38 |
| WO | 2011056995 | A2 | 5/2011 | ............... A61F 2/38 |
| WO | 2011/071979 | A2 | 6/2011 | ............... A61F 2/38 |
| WO | 2011072235 | A2 | 6/2011 | ............... A61F 2/38 |
| WO | 2011075697 | A2 | 6/2011 | ............... A61F 2/38 |
| WO | 2009111626 | A3 | 9/2011 | ............... A61F 2/38 |
| WO | 2011056995 | A3 | 9/2011 | ............... A61F 2/38 |
| WO | 2011075697 | A3 | 10/2011 | ............ A61B 2/38 |
| WO | 2011072235 | A3 | 12/2011 | ............... A61F 2/38 |
| WO | 2012112694 | A1 | 8/2012 | ............ A61B 6/00 |
| WO | 2012112694 | A2 | 8/2012 | ............ A61B 6/00 |
| WO | 2012112698 | A2 | 8/2012 | ............... A61F 2/30 |
| WO | 2012112701 | A2 | 8/2012 | ............... A61F 2/30 |
| WO | 2012112702 | A2 | 8/2012 | ............... A61F 2/30 |
| WO | 2012112694 | A3 | 1/2013 | ............ A61B 6/00 |
| WO | 2012112701 | A3 | 1/2013 | ............... A61F 2/30 |
| WO | 2012112702 | A3 | 1/2013 | ............... A61F 2/30 |
| WO | 2013020026 | A1 | 2/2013 | ............... A61F 2/30 |
| WO | 2013025814 | A1 | 2/2013 | ............... A61F 2/38 |
| WO | 2012112698 | A3 | 3/2013 | ............... A61F 2/30 |
| WO | 2013056036 | A1 | 4/2013 | ............... A61F 2/38 |
| WO | 2013119790 | A1 | 8/2013 | ............... A61F 2/38 |
| WO | 2013119865 | A1 | 8/2013 | ............ A61F 17/90 |
| WO | 2013131066 | A1 | 9/2013 | ............... A61F 2/38 |
| WO | 2013152341 | A1 | 10/2013 | |
| WO | 2013155500 | A1 | 10/2013 | ............... A61F 2/38 |
| WO | 2013155501 | A1 | 10/2013 | ............... A61F 2/30 |
| WO | 2014008444 | A1 | 1/2014 | ............ A61B 17/92 |
| WO | 2014035991 | A1 | 3/2014 | ............ A61B 17/56 |
| WO | 2014047514 | A1 | 3/2014 | ............... A61F 2/76 |

OTHER PUBLICATIONS

Hofmann et al, "Natural-Knee II System", Intermedics Orthopedics, Austin, TX, 1995.

Extended European Search Report, Application No. EP 12837887,4, dated Apr. 20, 2016.

International Search Report and Written Opinion dated Jul. 1, 2010 for PCT/US2010/025466.

International Preliminary Report on Patentability dated Jun. 7, 2011 for PCT/US2010/025466.

International Search Report and Written Opinion dated Apr. 23, 2010 for PCT/US2010/025467.

International Preliminary Report on Patentability dated Oct. 11, 2011 for PCT/US2010/025467.

International Search Report and Written Opinion dated Jan. 5, 2009 for PCT/US2008/009837.

International Preliminary Report on Patentability dated Apr. 1, 2010 for PCT/US2008/009837.

Mahfouz et al., "Three-dimensional Morphology of the Knee Reveals Ethnic Differences," Clin. Orthop. Relat. Res., vol. 470, No. 1, Jan. 2012, pp. 172-185.

Dennis et al, Coventry Award Paper, Multicenter Determination of In Vivo Kinematics After Total Knee Arthroplasty, Clinical Orthopaedics and Related Research, No. 416, pp. 37-57, c 2003 Lippincott Williams & Wilkins, Inc., USA.

Mahfouz et al, A Robust Method for Registration of Three-Dimensional Knee Implant Models to Two-Dimensional Fluoroscopy Images, IEEE Transactions on Medical imaging, vol. 22, No. 12, Dec. 2003, c 2003 IEEE, USA.

Mahfouz et al, Automatic methods for characterization of sexual dimorphism of adult femora: distal femur, Computer Methods in Biomechanics and Biomedical Engineering, 2007; iFirst article, 1-10, c 2007 Taylor & Francis, GB.

Mahfouz et al, Patella sex determination by 30 statistical shape models and nonlinear classifiers, Forensic Science international, FSI-5154, pp. 1-10, c 2007 Elsevier Ireland Ltd., IE.

Merkl et al, Unsupervised Three-Dimensional Segmentation of Medical Images Using an Anatomical Bone Atlas, published in biomedical conference in Singapore, Dec. 2005, University of Tennessee/Department of Mechanical, Aerospace and Biomedical Engrg., Knoxville, TN, USA.

Shapiro et al., "Similarity-Based Retrieval for Biomedical Applications", Studies in Computational Intelligence, Springer, 73, pp. 355-387, 2008.

\* cited by examiner

| MEDIAL | c1 | c2 | c3 | c4 |
|---|---|---|---|---|
| MEAN | 2.15 | 1.94 | 3.38 | 2.60 |
| STD | 0.98 | 0.36 | 2.09 | 1.22 |
| MEAN | 2.73 | 2.46 | 3.98 | 3.34 |
| STD | 1.31 | 1.19 | 2.20 | 1.41 |
| LATERAL | c1 | c2 | c3 | c3 |
| MEAN | 5.13 | 2.12 | 4.92 | 2.43 |
| STD | 6.11 | 0.96 | 2.09 | 0.91 |
| MEAN | 6.20 | 2.44 | 5.89 | 2.79 |
| STD | 9.64 | 1.09 | 4.24 | 0.94 |

FIG. 21

| SAGITAL ARCS | M | L | PROFILE ARCS | | M | L |
|---|---|---|---|---|---|---|
| 0 | 2.45 | 1.95 | 3.08 | 11.41 | 0.79 | 0.17 |
| 10 | 2.68 | 1.77 | | | 0.86 | 0.16 |
| 20 | 2.53 | 1.84 | | | 0.82 | 0.16 |
| 30 | 2.42 | 2.03 | | | 0.78 | 0.18 |
| 40 | 2.01 | 1.88 | 3.73 | 2.02 | 0.54 | 0.93 |
| 50 | 1.96 | 1.96 | | | 0.53 | 0.97 |
| 60 | 2.21 | 2.12 | | | 0.59 | 1.05 |
| 70 | 2.30 | 2.38 | | | 0.62 | 1.18 |
| 80 | 2.54 | 2.70 | 2.09 | 2.18 | 1.22 | 1.24 |
| 90 | 2.15 | 2.31 | | | 1.03 | 1.06 |
| 100 | 1.95 | 2.09 | | | 0.93 | 0.96 |
| 110 | 1.71 | 2.18 | | | 0.82 | 1.00 |
| 120 | 1.46 | 2.31 | 2.29 | 2.91 | 0.64 | 0.79 |
| 130 | 1.27 | 2.56 | | | 0.56 | 0.88 |
| 140 | 2.62 | 2.54 | | | 1.14 | 1.01 |
| 150 | 2.62 | 2.94 | | | 1.14 | 1.01 |

FIG. 31

HIGH VARIATION  LOW VARIATION

HIGH VARIATION  LOW VARIATION $$ADI(c) = min_{i \in c}\{min_{j \in c, i \neq j}\{\frac{min_{x_i \in C_i, x_j \in C_j}|d(y, v_j) - d(x_i, v_j)|}{max_{k \in c}\{max_{x,y \in C} d(x,y)\}}\}\}$$

|  |  | TEA | BML | APH | MAP | LAP | PA | ON | APA | AML | PML | DML | CTA |
|---|---|---|---|---|---|---|---|---|---|---|---|---|---|
| White | mean | 6.71 | 7.81 | 6.13 | 6.69 | 5.89 | 98.43 | 0.78 | 6.10 | 3.63 | 5.40 | 5.54 | 6.37 |
|  | std | 0.43 | 0.70 | 0.44 | 0.43 | 0.43 | 3.56 | 0.22 | 2.70 | 0.33 | 0.46 | 0.45 | 2.66 |
| Black | mean | 6.68 | 7.88 | 6.07 | 6.71 | 7.04 | 97.75 | 0.82 | 6.35 | 3.68 | 5.30 | 5.58 | 6.56 |
|  | std | 0.47 | 0.77 | 0.36 | 0.28 | 0.36 | 3.35 | 0.19 | 4.19 | 0.52 | 0.52 | 0.51 | 1.78 |
| Asian | mean | 7.55 | 5.25 | 5.23 | 5.98 | 6.00 | 95.17 | 0.76 | 3.47 | 3.38 | 4.88 | 4.38 | 7.12 |
|  | std | 0.40 | 1.68 | 0.62 | 0.33 | 0.35 | 3.59 | 0.42 | 2.53 | 0.47 | 0.46 | 0.45 | 2.65 |
| White Vs Black | t-test | 0.61 | 0.78 | 0.40 | 0.82 | 0.03 | 0.28 | 0.28 | 0.01 | 0.47 | 0.22 | 0.80 | 0.88 |
|  | Power Test | 102 | 19275 | 1165 | 13108 | 171 | 709 | 887 | 81 | 7175 | 637 | 14481 | 3527 |
| White Vs Asian | t-test | 0.01 | 0.01 | 0.01 | 0.01 | 0.01 | 0.01 | 0.64 | 0.03 | 0.01 | 0.01 | 0.01 | 0.07 |
|  | Power Test | 4 | 7 | 9 | 7 | 5 | 107 | 7146 | 26 | 76 | 7 | 4 | 321 |
| Black Vs Asian | t-test | 0.01 | 0.01 | 0.01 | 0.01 | 0.01 | 0.11 | 0.43 | 0.01 | 0.01 | 0.01 | 0.01 | 0.25 |
|  | Power Test | 7 | 8 | 9 | 5 | 5 | 164 | 704 | 13 | 73 | 10 | 5 | 398 |

TABLE 1

FIG. 75

|  |  | ML | AP | EW | TTA | LPH | LPW | MPH | MPW |
|---|---|---|---|---|---|---|---|---|---|
| White | Mean | 7.81 | 5.73 | 1.32 | 82.96 | 4.85 | 3.25 | 5.13 | 3.08 |
|  | std | 0.37 | 0.32 | 0.58 | 34.05 | 0.36 | 0.37 | 0.33 | 0.27 |
| Black | Mean | 7.88 | 5.73 | 1.44 | 79.29 | 5.03 | 3.22 | 5.15 | 3.14 |
|  | std | 0.4 | 0.34 | 0.79 | 33.89 | 0.39 | 0.38 | 0.43 | 0.32 |
|  | t-test | 0.41 | 0.96 | 0.4 | 0.63 | 0.05 | 0.64 | 0.73 | 0.34 |
|  | Power test | 759 | 266834 | 758 | 2223 | 177 | 2425 | 5382 | 592 |

TABLE 2

FIG. 76

| Flexion Angle | Length % |
|---|---|
| 0 | 24.85 |
| 20 | 17.90 |
| 40 | 10.35 |
| 60 | 17.32 |
| 80 | 28.15 |
| 100 | 39.36 |
| 120 | 46.60 |
| 140 | 47.23 |

TABLE 3

FIG. 77

DEFORMABLE ARTICULATING TEMPLATES

CROSS REFERENCE TO RELATED APPLICATIONS

The present application is a continuation of U.S. patent application Ser. No. 14/640,082 filed Mar. 6, 2015, which is a divisional of U.S. patent application Ser. No. 13/203,012 filed Feb. 25, 2010 (§ 371 date of Aug. 24, 2011), which is a national phase entry application of International PCT Patent Application No. PCT/US2010/25466 filed Feb. 25, 2010, which claims the benefit of U.S. Provisional Patent Application Ser. No. 61/208,509 filed. Feb. 25, 2009 and U.S. Provisional Patent Application Ser. No. 61/222,560, filed Jul. 2, 2009, the disclosure of each of which is hereby incorporated herein by reference.

TECHNICAL

The present disclosure relates to orthopaedic implants and, more specifically, to methods and devices utilized to design orthopaedic implants and orthopaedic jigs for use with joint replacement and revision procedures.

INTRODUCTION TO THE INVENTION

Of primary interest to the knee prosthetics industry is the analysis of the intrinsic shape differences of the knee joint between different ethnic populations for development of implantable orthopaedic devices. The study presented is thus three-fold: by developing a novel automatic feature detection algorithm, a set of automated measurements can he defined based on highly morphometric variant regions, which then allows for a statistical framework when analyzing different populations' knee joint differences.

Ethnic differences in lower limb morphology focuses on the differences between Asian and Western populations because this variation is of great import in implant design. For example, Chinese femora are more anteriorly bowed and externally rotated with smaller intermedullary canals and smaller distal condyles than Caucasian femora. Likewise, Caucasian femora are larger than Japanese femora in terms of length and distal condyle dimensions. Ethnic differences in proximal femur bone mineral density (BMD) and hip axis length also exists between American Blacks and Whites. The combined effects of higher BMD, shorter hip axis length, and shorter intertrochanteric width may explain the lower prevalence of osteoporotic fractures in Black women compared to their White counterparts. Similarly, elderly Asian and Black men have been found to have thicker cortices and higher BMD than White and Hispanic men, which may contribute to greater bone strength in these ethnic groups. In general, Blacks have thicker bone cortices, narrower endosteal diameters, and greater BMD than Whites. Interestingly, though, these traits are most pronounced in African Blacks compared to American Blacks.

The following analysis considers metric and geometric morphometric variation in the lower limb of modern American Blacks, Whites and East Asians. Three-dimensional statistical bone atlases are used in order to facilitate rapid and accurate data collection in the form of automated measurements, as well as measurements used in biomedical studies and some newly-devised measurements. The shape analysis is conducted with a statistical treatment combining Principal Components Analysis (PCA) and Multiple Discriminant Analysis; metric analysis is performed using t-tests, power tests, and linear discriminant analysis in the Implant Design and Analysis Suite (see co-pending U.S. patent application Ser. No. 12/673,640, entitled, IMPLANT DESIGN ANALYSIS SUITE, the disclosure of which is incorporated herein by reference) system. The results of these analyses add to the existing knowledge of morphological variation in the knee joint and provide useful information that can be extracted for knee prosthesis design as will be outlined in the remainder of this disclosure.

The innovativeness of the instant approach derives, in part, from the use of Computed Tomography (CT) scans for data collection combined with the computational power and precision offered by statistical bone atlases. An exemplary data set that comprises 943 male and female individuals (81.5% American White, 9% American Black and 9.5% East Asians, where the overall male/female ratio 65/35%) was scanned using CT scans. Only normal femora and tibia were included in this study; femora or tibia with severe osteophytes and other abnormalities were specifically excluded. Only one femur and tibia was chosen from each individual, with no preference taken to either right or left side.

The bones were CT scanned using 0.625 mm×0.625 mm×0.625 mm cubic voxels. The result is high resolution, three dimensional radiographs in the form of DICOM image slices. This stacked image data was then segmented and surface models were generated. This process has been found to be reliable with negligible inter- and intra-observer error. These models were then added to the ethnicity-specific statistical bone atlases.

Briefly, a bone atlas is an average mold, or template mesh, that captures the primary shape variation of a bone and allows for the comparison of global shape differences between groups or populations. Bone atlases were developed initially for automatic medical image segmentation; however, it can be used as a way to digitally recreate a bone and conduct statistical shape analyses. In addition, bone atlases have proven useful in biological anthropology as a means of studying sexual dimorphism and for reconstructing hominid fossils and making shape comparisons among fossil species.

For the ethnicity difference analysis, a previously developed technique for creating a statistical representation of bone shape was employed in a novel manner. Three separate statistical atlases of femora were compiled with one atlas containing only American White femora, one atlas containing only American Black femora, and one atlas containing only East Asian femora. Likewise, three separate atlases were created for the tibia and divided in the same manner (i.e., American White, Black tibiae and East Asians). The processes of creating these statistical atlases and adding bones to the atlases are outlined hereafter.

First, all of the bone models in the dataset were compared, and a bone model with average shape characteristics was selected to act as a template mesh. The points in the template mesh were then matched to corresponding points in all of the other training models. This ensures that all of the bones have the same number of vertices and the same triangular connectivity. Next, a series of registration and warping techniques was used to select corresponding points on all the other bone models in the training set. This process of picking point correspondences on new models to be added to the atlas is 'non-trivial'. The matching algorithm described hereafter uses several well-known techniques of computer vision, as well as a novel contribution for final surface alignment.

During the first step in the matching algorithm, the centroids of the template mesh and the new mesh were aligned, and the template mesh was pre-scaled to match the bounding box dimensions of the new mesh. Second, a rigid alignment of the template mesh to the new mesh was performed using a standard vertex-to-vertex Iterative Closest Point (ICP) algorithm. Third, after rigid alignment, a general affine transformation was performed without iteration. This method was applied to align the template mesh to the new mesh using 12 degrees of freedom (including rotations, translations, scaling, and shear). After the affine transformation step, the template and new model have reached the limits of linear transformation, but local portions of the models still remain significantly distant. Since the goal of final surface-to-surface matching is to create new points on the surface of the new model that will have similar local spatial characteristics as the template model, a novel non-linear iterative warping approach was developed to reduce misalignment.

Referring to FIG. 1, to achieve point correspondence, an iterative algorithm is used where the closest vertex-to-vertex correspondences are found from the template to the new model as before, but now the correspondences from the new model to the template model are also found. Using both of these point correspondences, points on the template mesh are moved toward locations on the new mesh using a non-symmetric weighting of the vectors of correspondence. Next, a subroutine consisting of an iterative smoothing algorithm is applied to the now-deformed template mesh. This smoothing algorithm seeks to average the size of adjacent triangles on the template mesh, thereby eliminating discontinuities. At the beginning of the warping algorithm, the smoothing algorithm uses the actual areas of the surrounding triangles to dictate the smoothing vector applied to each point, which aids in effectively removing outlying points with large triangles. Consequently, at the beginning of the process, the template mesh makes large steps, and larger smoothing is required. Toward the end of the process, however, the smoothing vector is normalized by the total area of the surrounding triangles, which allows for greater expansion of the template mesh into areas of high curvature. After this procedure has been completed on all the femora and tibiae in their respective atlases, the atlases are ready for morphological shape analyses and automated metric comparisons.

An innovative statistical treatment was used to analyze global shape differences between the two groups. This method utilizes the power of (linear and nonlinear) PCA both as a means of variable reduction and as a global shape descriptor. This method is designed to find points of high discrimination between different gender and/or different ethnic groups when normalized against the first principal component (PC), which is considered primarily to scale. This procedure highlights areas on models that would be highly discriminating without the use of any other information. The landmarks identified by this algorithm provide adequate discrimination without the use of any other landmarks between ethnic groups. This feature finder algorithm is used to examine femoral and tibial shape differences independent of the size differences between American Whites, Blacks and East Asians.

A wide array of comparisons was made using specific measurements at defined landmarks on the ethnicity-specific statistical atlases. These landmarks were chosen based on surgical importance, clinical relevance, and historical measurements. Since the atlas consists of homologous points on each femur or tibia model, it provides ample information for automating this process. Also, each bone model in the atlas is aligned to the same coordinate frame. A total of 99 femur and 23 tibia measurements, angles, and indices were calculated. Furthermore, for purposes of brevity, only the most significant metric properties are discussed in the results section. Unless otherwise specified, the measurements outlined below represent three dimensional (3D) Euclidean distances between pairs of landmarks, and angles are measured as 3D rotations between vectors. In some instances these measurements were projected onto a plane for comparison with previous work in the field. A subset of these measurements is shown in FIGS. 2-4. The landmarks that define the measurement endpoints are first computed and then defined relative to surgical and anatomical axes.

Presented are novel methods to ascertain ethnic differences on the distal femur and proximal tibia on a global scale, to discover regions that were likely to offer discriminating information, and to measure relevant surgical and anatomical features to aid implanted prosthesis design. Different studies have tried to identify ethnical differences of the femur and tibia using measurement techniques that lacked accuracy or precision. Unfortunately, these methods have been unable to find features of smaller consequence.

The ordered series of methods used pursuant to the instant disclosure evidenced significant global differences among sex and race, which subsequently allowed for isolation of regions likely to be highly different using the feature finder method, and finally allowed for the coding of algorithms to locate and measure surgically relevant anatomic features with a high degree of accuracy and repeatability. Bones with different scales were considered to have the possibility of shape changes dependent on size. In this way, correlations between measured variables and size were removed in order to expose demonstrable shape differences inherent to the ethnicities.

The inventor has used the foregoing analysis to determine that American Blacks have longer, straighter femora with narrower knees than American Whites. In addition, this analysis revealed differences in the dimensions and orientation of the lateral condyle that result in overall shape differences in the distal femur: American Blacks have a trapezoidal-shaped knee, and American Whites have a more square-shaped knee. For each group, the differences in the distal femur are echoed in the adjacent tibia, whereby American Blacks have a longer lateral tibial condyle. The mean medial-lateral length of the tibial plateau is slightly longer in Blacks than in Whites, but this difference was not overly significant given the sample size. However, American Blacks do have significantly longer and more robust tibiae. In this study, major shape difference was found between East Asian population and both American whites and American blacks.

It is not clear to what extent genetic differences contribute to lower limb morphology, admixed individuals present a challenge. Indeed, blood type data indicates that since their arrival in the United States, American Blacks have become more similar to American Whites and more divergent from their ancestral West African population.

Although racial differences in lower limb morphology are apparent and register statistically significant, there may be more statistical noise in the American Black sample versus the American White sample. This noise may be a result of the combined effects of genetic admixture since their arrival in the United States, as well as relaxed selection in a more temperate environment. Nonetheless, as discussed earlier, the effects of admixture have not erased the distinctive morphological differences between these subgroups of the American population.

In order, to understand normal knee joint kinematics, one must first understand the anatomy of the articulating surfaces of the knee joint. The knee joint is the articulation of the two largest bones in the human lower extremity, the tibia and the femur. The articular surfaces at the knee joint consists of the curved surfaces that form the lateral and medial condyles of the distal portion of the femur and are in contact with the lateral and medial tibial plateaus of the proximal portion of the tibia.

The femoral condyles blend into an anterior groove, the trochlea, which is the articulation for the patella or kneecap. The tibial plateaus are separated by an intercondylar eminence, which serves as an attachment point for the anterior cruciate ligament and the menisci. The tibial plateaus are also asymmetric, with the lateral plateau the smaller of the two. Anatomical studies of the femorotibial articulation have shown that the medial compartment has greater contact area than the lateral compartment.

The fibula is attached to the tibia's lateral side by a dense membrane along its length and at the ends by cartilaginous joints supported by ligaments. The connection of the bones permits very little relative movement. The proximal tibia-fibular joint is below the level of the tibia-femoral articulation, while the distal ends of the two bones form the proximal end of the ankle joint.

In the normal knee, posterior femoral rollback during an increasing flexion routinely occurs. Greater amounts of posterior femoral rollback have been observed during activities requiring greater magnitudes of flexion such as a deep knee bend maneuver. Posterior rollback is substantially greater at the lateral femorotibial articulation than medially, therefore creating a medial pivot type of axial rotational pattern in which the tibia internally rotates relative to the femur as flexion increases. Numerous kinematic evaluations have found a similar pattern and magnitude of posterior femoral rollback during deep flexion activities. This differs somewhat from axial rotational patterns observed after total knee arthroplasty (TKA), which showed lower magnitudes of axial rotation and occasional pathologic rotational patterns such as lateral pivot rotation and reverse screw-home rotation (tibia externally rotating relative to the femur with increasing flexion).

Also, the anterior translation of the femur on the tibia observed after TKA has numerous potential negative consequences. First, anterior femoral translation results in a more anterior axis of flexion, lessening maximum knee flexion. Second, the quadriceps moment arm is decreased, resulting in reduced quadriceps efficiency. Third, anterior sliding of the femoral component on the tibial polyethylene (PE) surface risks accelerated PE wear.

A primary objective of TKA should be to reproduce the kinematics of a normal knee. At present, this objective is largely overlooked. Numerous in vivo, weightbearing, and fluoroscopic analyses have shown that normal knee kinematics are difficult to obtain after TKA using existing orthopaedic implants. Multiple kinematic abnormalities (reduced posterior femoral rollback, paradoxical anterior femoral translation, reverse axial rotational patterns, and femoral condylar lift-off) are commonly present. Understanding these kinematic variances assisted in design of better TKA implants, which work toward reducing and eliminating these kinematic abnormalities or at least accommodating them without creating adverse conditions that limit implant performance or longevity. Most of the knee implants are off-the shelve-knee systems, which are designed for average motion—not patient specific kinematics. Accordingly, TKA motion and kinematics of the knee that are indistinguishable from a normal knee should utilize customization for each patient. Currently, customization is a difficult task, but the instant disclosure addresses this customization, in part, by offering a deformable articulating template (DAT) methodology described hereafter.

For purposes of the instant disclosure, radius of curvature is the radius of a circle having a circumferential curvature that approximates the curvature of a rounded object. For example, the radius of curvature is infinite for a straight line, while the radius of decreases from infinity as the curvature increases. As can be seen in FIG. 5, the radius of curvature for the smaller circle is less than the radius of curvature for the larger circle because the curvature of the smaller circle is greater than the curvature of the larger circle. Simply put, the smaller the radius of curvature, the larger the curvature.

Referring to FIGS. 6 and 7, the inventor has found that one may map and simulate the curvature of the natural knee condyles by applying two or more radii of curvature along the camming surfaces from anterior to posterior. In particular, it has been found that for the Caucasian population, five distinct radii of curvature (identified as r1-r5) closely track the curvature of the camming surfaces of the condyles from anterior to posterior. Moreover, it has been found that asymmetry in the radii of the curvature of the condyles is responsible for imposing an internal rotation of the tibia with respect to the femur during flexion. Beyond 20° of flexion, sliding motion begins on both condyles.

Extension of the knee joint produces a coupled external rotation of the tibia with respect to the femur; this rotation has been described as the "screw-home" movement of the knee. This screw-home movement is due to the existence of a larger area of bearing surface on the medial condyle than on the lateral condyle. When the whole articular surface of the lateral condyle has been used up, the femur rotates around the tibial spine until the joint is screwed home or close packed in extension. As the knee joint flexes and extends, this rotation causes the tibial motion on the femur to assume a spiral or helicoid form that results from the anatomical configuration of the medial femoral condyle. As the tibia slides on the femur from the fully extended position, it descends and ascends the curves of the medial femoral condyle and simultaneously rotates externally. This motion is reversed as the tibia moves back into the fully flexed position. The screw-home mechanism gives more stability to the knee in any position than would be possible if the femorotibial joint was a pure hinge joint.

Referring to FIG. 8, the meniscal cartilages (menisci) between the femoral condyles and the tibial articular surfaces are two crescentic fibrocartilage structures that serve to deepen the articular surfaces of the tibia for reception of the femoral condyles. On cross-section, the menisci have a wedge-like appearance. The menisci perform several important functions, including (1) load transmission across the joint, (2) enhancement of articular conformity, (3) distribution of the synovial fluid across the articular surface, and (4) prevention of hone impingement during joint motion. When the menisci are present, the load-bearing area for each condyle approximates 6 $cm^2$, but this surface area decreases to approximately 2 $cm^2$ when the menisci are damaged or severely degraded. Therefore, when the effective area of load bearing is increased, the stress transferred to the cartilages is reduced and vice versa.

Referencing FIGS. 9 and 10, in the normal knee joint, the anterior cruciate ligament (ACL) and the posterior cruciate ligament (PCL) are intrinsic, lying inside the joint in the intercondylar space. These ligaments control the anterior-posterior and axial rotational motion in the joint. The anterior cruciate ligament provides the primary restraint for anterior movement of the tibia relative to the femur while the posterior cruciate ligament offers the primary restraint to posterior movement of the tibia, accounting for over 90% of the total resistance to this movement. FIG. 10 shows the change in length of the ACL and PCL during different flexion angles of the knee joint. A detailed description of the effect of ACL and PCL constraints on the design of posterior stabilized knee implants will be discussed in more detail hereafter.

The morphologic shape of the distal femur should dictate the shape, orientation, and kinematics of the prosthetic replacement used for TKA. Traditional prosthetic designs incorporate symmetric femoral condyles with a centered trochlear groove. Traditional surgical techniques center the femoral component to the distal femur and position it relative to variable bone landmarks. However, documented failure patterns and kinematic studies demonstrate how traditional design and surgical techniques reflect a poor understanding of distal femoral morphology and knee joint kinematics, in addition to a disregard for the patella and its tracking of the distal femur.

The trochlea is designed to guide and hold the patella. Patella tracking is influenced by many different factors: the geometry of the trochlear groove, the geometry of the posterior side of the patella, soft tissue extensor mechanism and the orientation of the tibia. The normal movement of the patella on the femur during flexion is a vertical displacement along the central groove of the femoral patellar surface down the intercondylar notch. The geometry of the trochlear groove and the posterior side of the patella constrains patella tracking, particularly at high flexion angles. The patella is held centrally by the conformity of the facets with the sulcus of the femur and by the patellofemoral ligaments. These ligaments represent a conformation of the capsule into thickened structures on the medial and lateral side of the patella. These ligaments are located superiorly and inferiorly on either side, and extend from the anterior surface of the patella posteriorly to the side of each femoral condyle. These ligaments also constrain the motion of the patella, but can be overruled by the sulcus constraints or by external forces. In a normal knee it is acceptable to presume that the tracking of the patella will be very similar to the orientation of the trochlea. As a result, the orientation of the trochlear groove of a knee prosthesis should be similar to the orientation of the natural trochlea to reproduce this natural patella track.

In sum, the knee joint is an example of very well balanced system. A slight change within this system, affects the whole system. Changes within the patella-femoral joint can have considerable long term effects, as the transmitted forces within this part of the knee joint are relatively high. TKA easily induces changes within the patella-femoral joint. At present, the simulated trochlear groove orientation of TKA components does not conform to the natural trochlear orientation. Accordingly, the groove orientation of future femoral components should incorporate a trochlear groove that simulates the natural orientation of the trochlear groove of a natural femur.

BRIEF DESCRIPTION OF THE DRAWINGS

FIG. 21 is an exemplary chart representing measurements of radii of curvature for a series of distal femurs for both human males and females, as well as where the measurements were taken.

FIG. 31 is the mathematical representation of the curvature displayed in FIG. 24.

FIGS. 66A and 66B are exemplary listings of parameters used to describe an exemplary femoral component designed in accordance with the instant disclosure.

FIG. 75 (Table 1) lists important femur measurements means, standard deviations, t-tests, and power test results for typical Asians, typical American Whites, and typical American Blacks.

FIG. 76 (Table 2) lists important tibia measurements— means, standard deviations, t-tests, and power test results for typical Asians, typical American Whites, and typical American Blacks.

FIG. 77 (Table 3) lists percentage length change in anterior cruciate ligament and posterior cruciate ligament with respect to knee flexion angle.

DETAILED DESCRIPTION OF EXEMPLARY EMBODIMENTS

The exemplary embodiments of the present invention are described and illustrated below to encompass methods and devices for designing prosthetic knee implants and, more specifically, to devices and methods for designing knee implants that more closely track the biomechanics of the natural knee and the resulting implants themselves. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
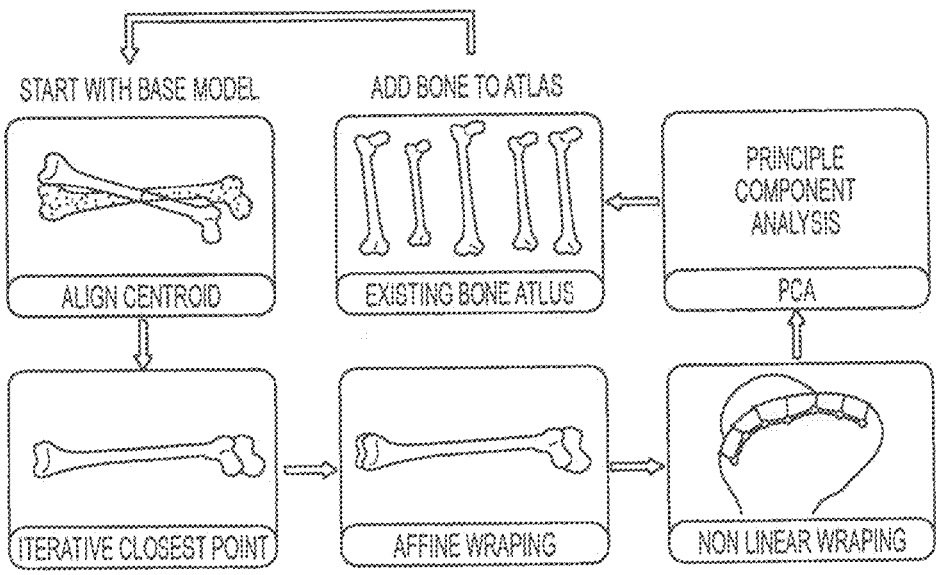
FIG. 1 is a flow chart outlining the process of atlas creation.
Figure 2:
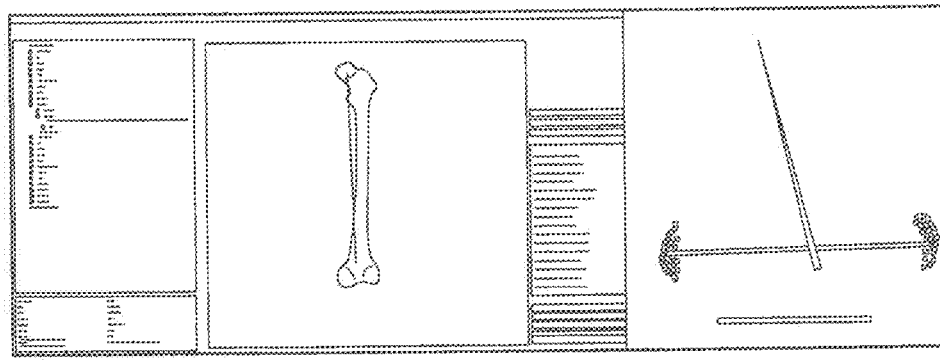
FIG. 2 is a screen shot and associated image showing automatic calculation of landmarks using the IDAS software.
Figure 3:
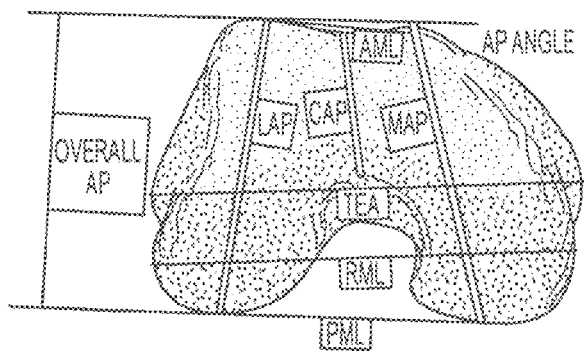
FIG. 3 is a distal end view of a femur showing the axes, landmarks, and measurements taken.
Figure 4:
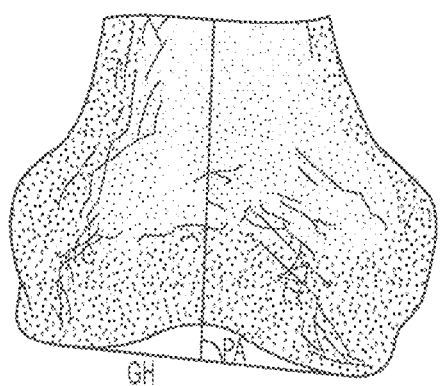
FIG. 4 is a frontal view of the femur of FIG. 3, showing certain axes, landmarks, and measurements taken.
Figure 5:
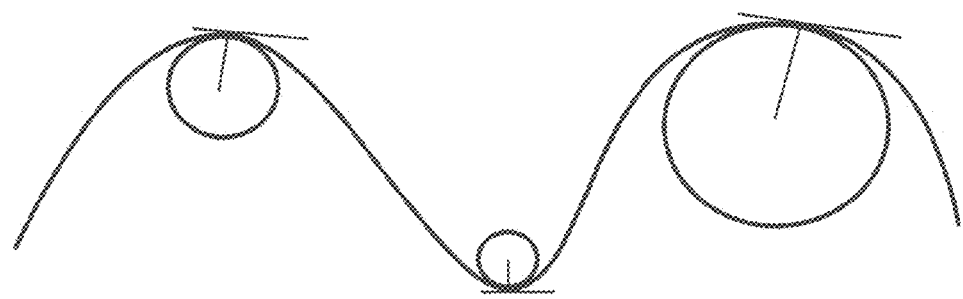
FIG. 5 is an exemplary diagram showing how curvature on the surface of a bone may be approximated using circles having different radii.

The following are definitions that relate to axes, landmarks, and measurements with respect to the distal femur (see FIGS. 2-4). These definitions also govern the proper construction of these terms as used in the instant disclosure.

Transepicondylar Axis (TEA)—This measurement is known in the anthropological literature as biepicondylar breadth. To compute the clinical transepicondylar axis (TEA), rough sets of vertices were manually defined on an average femur on the most lateral prominence of the lateral epicondyle and the most medial prominence of the medial epicondyle. This step was only performed once, since vertices in the atlas femora are homologous. Using these rough sets of points, a search region of 10 mm radius was defined from the centroid of the rough sets of vertices on both the lateral and medial sides. Defining the vector from each of these centroids then gives a rough direction for the TEA. A pair of points was selected by maximizing the distance in this rough direction; these selected points form the endpoints of the TEA measurement (see FIG. 2).

Distal Anatomical Axis—The distal anatomical axis was defined by locating the shaft centroids at the distal one-third and distal one-fifth of the overall femur length.

Central AP Axis (CAP)—Using the distal anatomical axis and the TEA, a mutually perpendicular axis was defined with termini at the posterior aspect of the intercondylar notch and the most anterior portion of the intercondylar groove. The length of this axis is recorded as CAP (FIG. 3). This axis is similar to 'height of intercondylar notch'.

Femoral Saddle Point—A landmark located at the most distal extension of the intercondylar groove.

Knee Center (K)—Using the two endpoints of the CAP measurement and the femoral saddle point, a plane is defined which bisects the femur into medial and lateral sides. The intersection of this plane with the TEA is the knee center, which forms the distal endpoint of the mechanical axis (MA) of the femur. The proximal endpoint of the MA is the center of the femoral head (see proximal femur measurements below).

AP Direction—Using the MA and the TEA, a mutually perpendicular vector with its origin at the knee center is used to define the antero-posterior (AP) direction, resulting in a direction similar to Whiteside's line.

Anterior Medio-lateral Width (AML) and Posterior Medio-lateral Width (PML) The AP direction was used to locate four landmarks: the most anterior and posterior points on the medial and lateral condyles of the distal femur. Connecting the two most anterior points gives a measurement of anterior medio-lateral width (AML) along the trochlear line, while connecting the two most posterior points gives a measure of posterior medio-lateral width (PML) measured along the posterior condylar axis (PCA) (see FIG. 2).

AP Length of Medial and Lateral Condyles (LAP and MAP)—Connecting the pairs of lateral and medial vertices defined above, respectively, gives the AP length of the lateral condyle (LAP) and medial condyle (MAP) (see FIG. 3).

Posterior Plane—A unique plane containing the endpoints of the PML measurement, which is also parallel to the MA, was used to define the posterior plane.

Overall AP Length—The minimum distance between the prominences of the lateral anterior condyle and the posterior plane (see FIG. 3).

AP Angle—The angle of the AML vector relative to the posterior plane (see FIG. 3).

Distal Medial-lateral Length (DML)—The most distal aspects of the medial and lateral condyles were recorded using MA as a reference direction. The distance between these two landmarks was denoted as DML.

Posterior Angle (PA)—The angle between the vector connecting the DML length and the mean axis of the femur (see FIG. 4).

Condylar Twist Angle (CTA)—The angle between the TEA and PCA.

Patellar Groove Height (GH)—Calculated between the posterior aspect of the intercondylar notch and the midpoint between the two DML axis points (see FIG. 4).

Femoral Shaft Curvature (SC)—The radius of curvature of the femoral mean axis.

Figure 11:
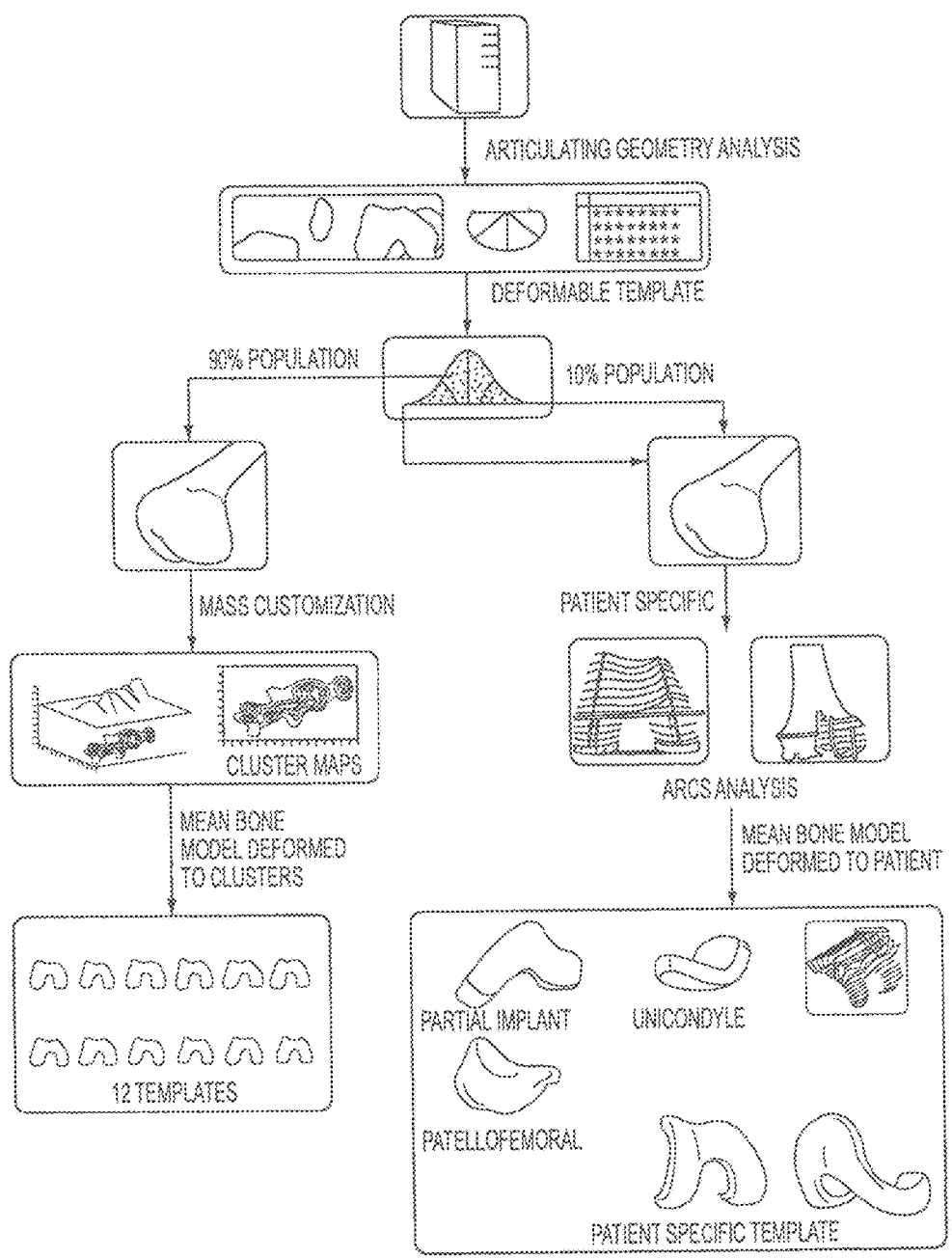
FIG. 11 is an overall schematic of an exemplary process for designing an orthopaedic implant that is customized for a patient or comprises one of a series of templates for general populations.

Referring to FIG. 11, a schematic overview of the exemplary knee design process 100 includes obtaining one or more electronic three dimensional (3D) bone representations 102 that are stored in an electronic database. For purposes of designing a total knee implant, in the case of total knee arthroplasty, that will replace the distal portion of the femur, the proximal portion of the tibia, the cartilage therebetween, and at least a portion of the patella, it is useful to have 3D bone representations of the distal femur, the proximal tibia, and the patella, as well as 3D jig representations utilized to prepare the femur, tibia, and patella for accepting TKA orthopaedic components. To generate these 3D bone representations and 3D jig representations, a patient or cadaver may undergo a CT scan, a series of X-rays, an MRI, and/or ultrasound imaging. The images of the bones and soft tissues from these tests, and possibly interpolated aspects of bone or soft tissue, are utilized to construct one or more 3D bone representations and one or more 3D jig representations.

The images from the foregoing tests are loaded into a computer for data analysis. As is known to those skilled in the art, an MRI creates a series of 2D "slices" of the relevant portion of the human anatomy. These 2D slices may then be segmented and stacked upon one another to create a 3D model or representation of the human anatomy. To the extent MRI is used to construct the slices, the precision of the 3D model depends in part upon how "thick" the slices are from the MRI. An analogous process is utilized for CT scans, X-rays, and ultrasounds where the 2D images are taken from distinct points and utilized to construct a 3D model of the anatomical feature in question, for exemplary purposes only this anatomical feature in question is described in the context of a human knee joint.

This same process for taking 2D images and using these images to create a 3D model is applicable to generating any 3D model of a human joint or bone(s). This same process may be applied to a living or dead human being in order to generate a plurality of bone or joint models for further analysis. It should also be understood that these same 2D images are useful to construct 3D models of cartilage that may be selectively interposed between bones, in exemplary form the femur and tibia, to more accurately depict the anatomy of each human feature (bone, joint, etc.). As will be discussed hereafter, the 3D models of the cartilage may be useful in constructing the 3D jig models.

Figure 12:
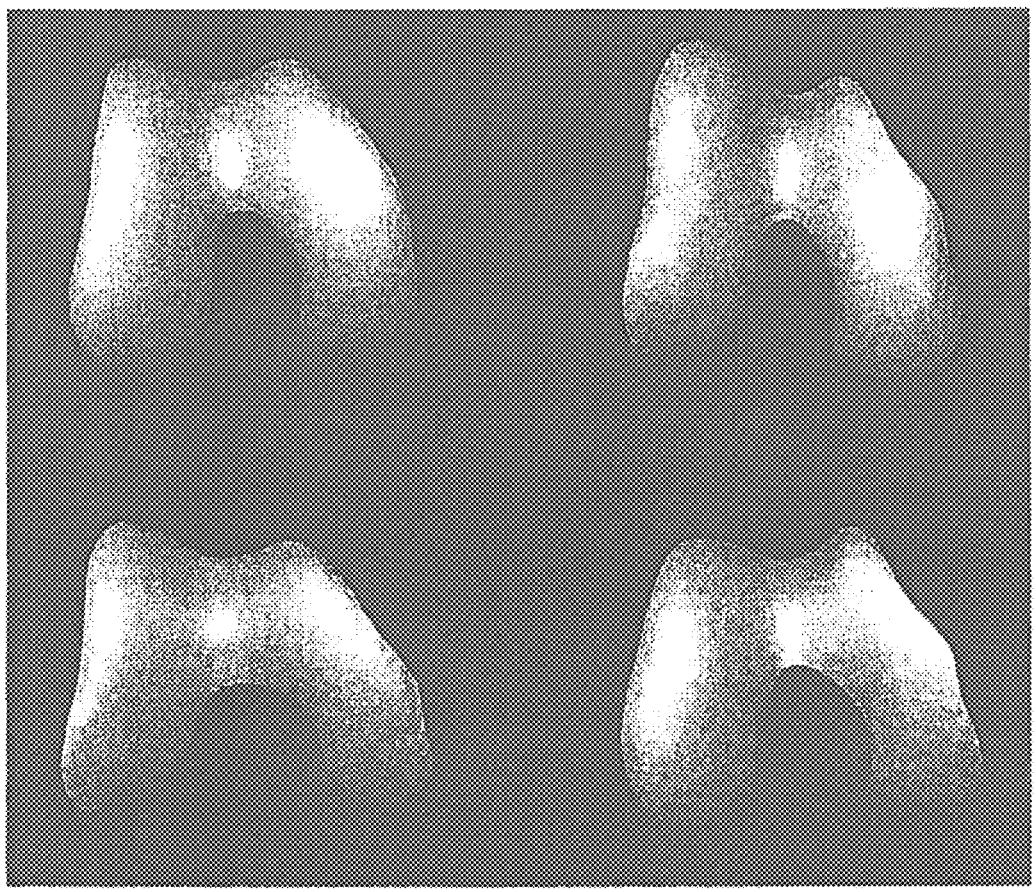
FIG. 12 is a bottom view of several electronic 3D distal femur models generated from medical imaging equipment that correspond to actual natural femurs from human patients.

Referring to FIG. 12, a series of 3D distal femoral representations are shown. As will be discussed in more detail hereafter, the exemplary knee design process 100 may be utilized to design and construct a customized knee implant that is unique to the anatomy of each patient. In addition, the exemplary knee design process 100 may be utilized to design and construct one or more generic implants that may be utilized to approximate the anatomies of larger populations where customization costs are not commercially feasible or preferable.

Referring back to FIG. 11, after one or more bones have been modeled so that 3D representations, in electronic form, have been generated, the 3D representations are stored in a database 104 that correlates additional data with the 3D representations. In exemplary form, the database 104 also includes data specific to each 3D representation in order to classify the representation including, without limitation, age, gender, race, and height of the human from which the bones, joint, etc., were scanned. At the same time, each 3D representation may include a grade or evaluation as to the condition of the bone, joint, etc. In exemplary form, when a 3D depiction of a knee joint (at least the proximal tibia and distal femur) is saved in the database 104, classifications for cartilage wear, bone degeneration, and osteophyte growth can be identified.

Figure 13:
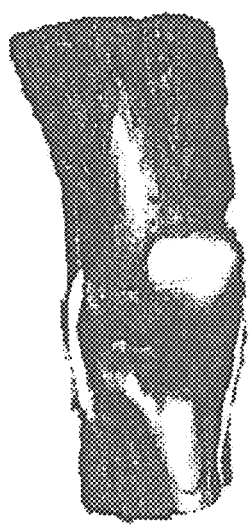
FIG. 13 is an electronic model of a human knee joint, including cartilage and ligaments, based upon medical imaging equipment data of an actual human knee joint, with the joint shown in the flexed position.
Figure 14:
FIG. 14 is an electronic model of a human knee joint, including cartilage and ligaments, based upon medical imaging equipment data of an actual human knee joint, with the joint shown proximate full extension.

Referring to FIGS. 13 and 14, subsequent to the generation of each individual bone model, the exemplary process 100 includes generation of a 3D model of the knee joint 300. This 3D model 300 of the knee joint includes orienting the distal femur 302, proximal tibia 304, and patella 306 as each would be when the joint was in full extension. Thereafter, computer software is operative to reposition the bones of the 3D model to create a virtual range of motion for the knee joint through full flexion. At the same time, the 3D models 300 may include cartilage (not shown) that interposes the bones 302, 304, 306 to represent the natural cartilage that cooperates with the proximal end of the tibia 304 to form medial and lateral condyle receivers.

Figure 15:
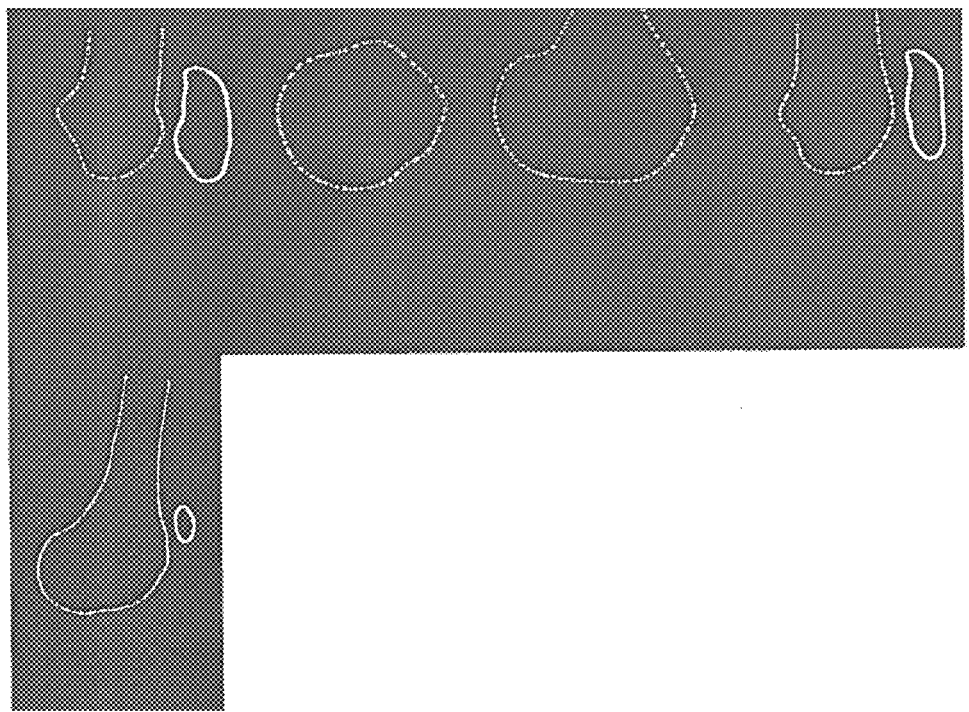
FIG. 15 is a series of 2D vertical slice representations of a knee joint showing the interaction between the tibia, femur, and patella proximate full extension.
Figure 16:
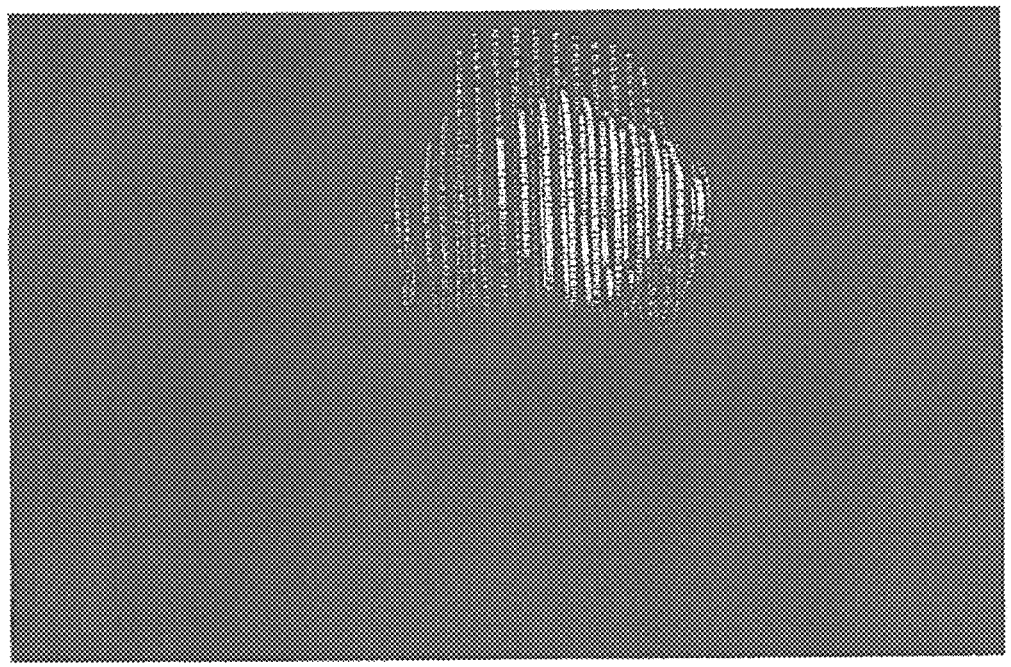
FIG. 16 is a 3D representation of the 2D slices of FIG. 15 in addition to other vertical slices to show where the slices are taken and the relative positions of the tibia, femur, and patella proximate full extension.

Referencing FIGS. 15 and 16, the 3D joint model 300 is useful to generate 2D contact profiles or "slices" showing how the orientation of each slice changes as knee joint is taken through its range of motion. In particular, these 2D representations are useful in understanding that a prosthetic implant, just like a natural knee, can be thought of as a series of slices that combine and work together to form the entire joint. As a result, by evaluating and understanding the geometry of each slice, specific contours may be seen that will be unique to each patient or may be generalized over a more encompassing population. It should be noted that the 3D joint model 300 may incorporate different topographies depending upon ethnicity, gender, and/or age. These differing topographies result in differing slices.

Figure 17:
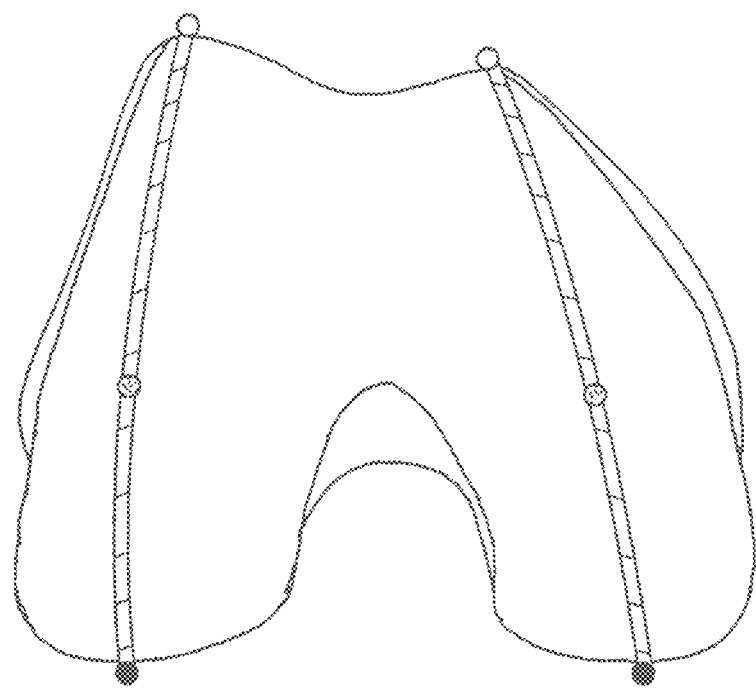
FIG. 17 is a distal view of the femur showing furthest anterior, distal and posterior points along the medial and lateral camming paths.
Figure 18:
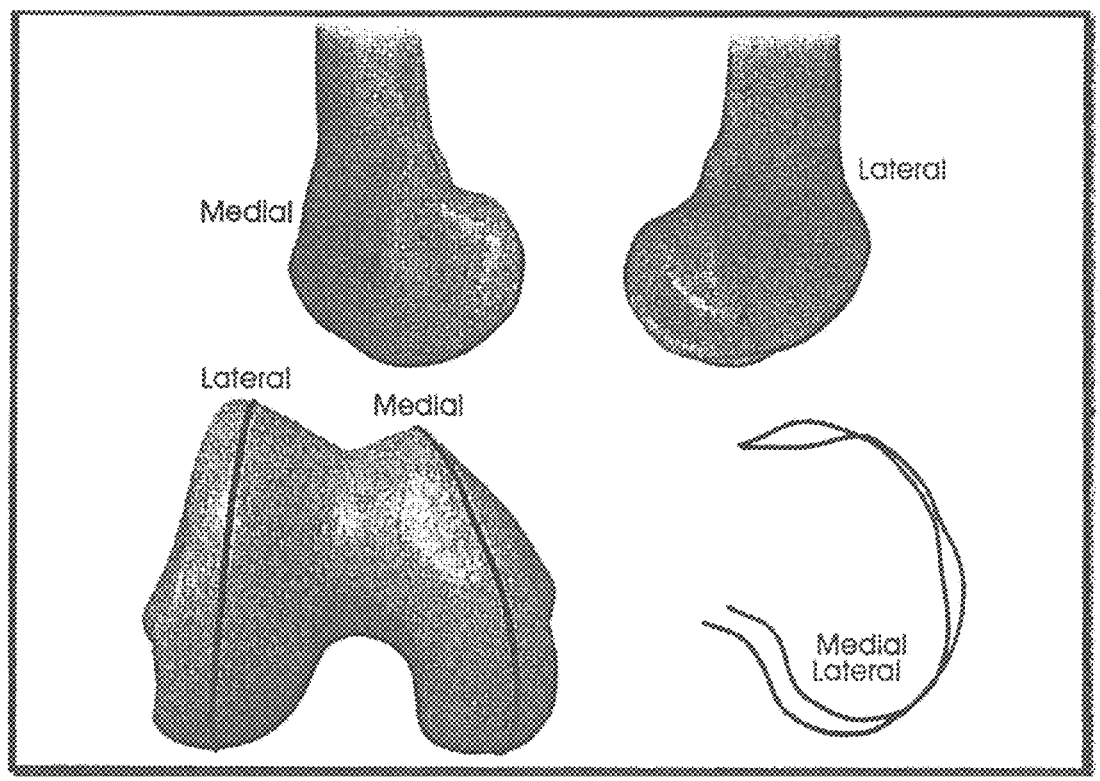
FIG. 18 is a compilation of views of the medial and lateral condyles of a distal femur having a path approximating the most outward portion of the camming surface of each condyle throughout the range of motion of each condyle.
Figure 19:
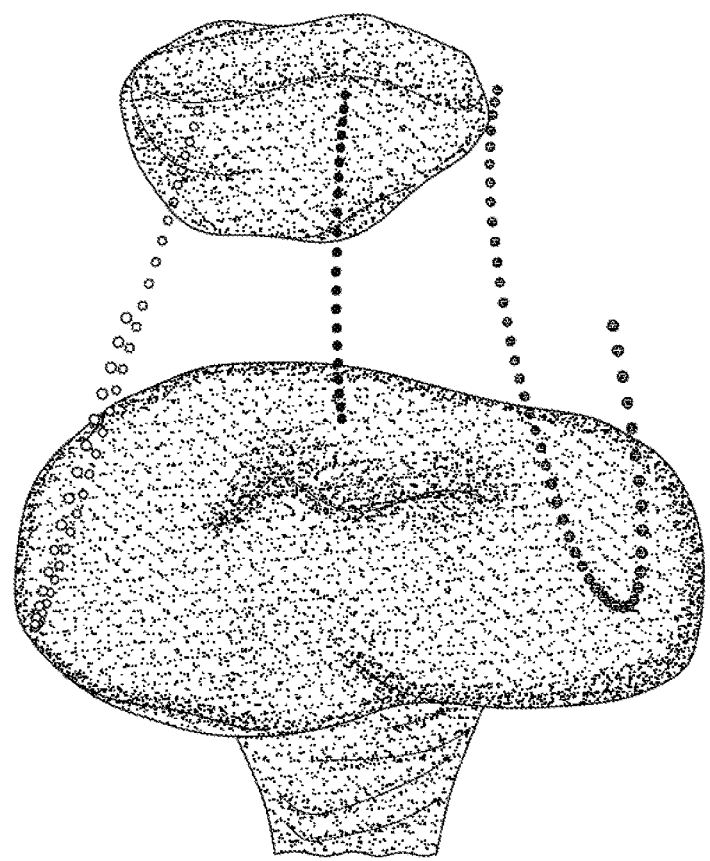
FIG. 19 is an elevated posterior view of a 3D representation showing a tibia and patella relative to the path of the outward most portion of the camming surface of each condyle for an exemplary distal femur, as well as the inner most surface of the trochlear groove associated with the distal femur.
Figure 20:
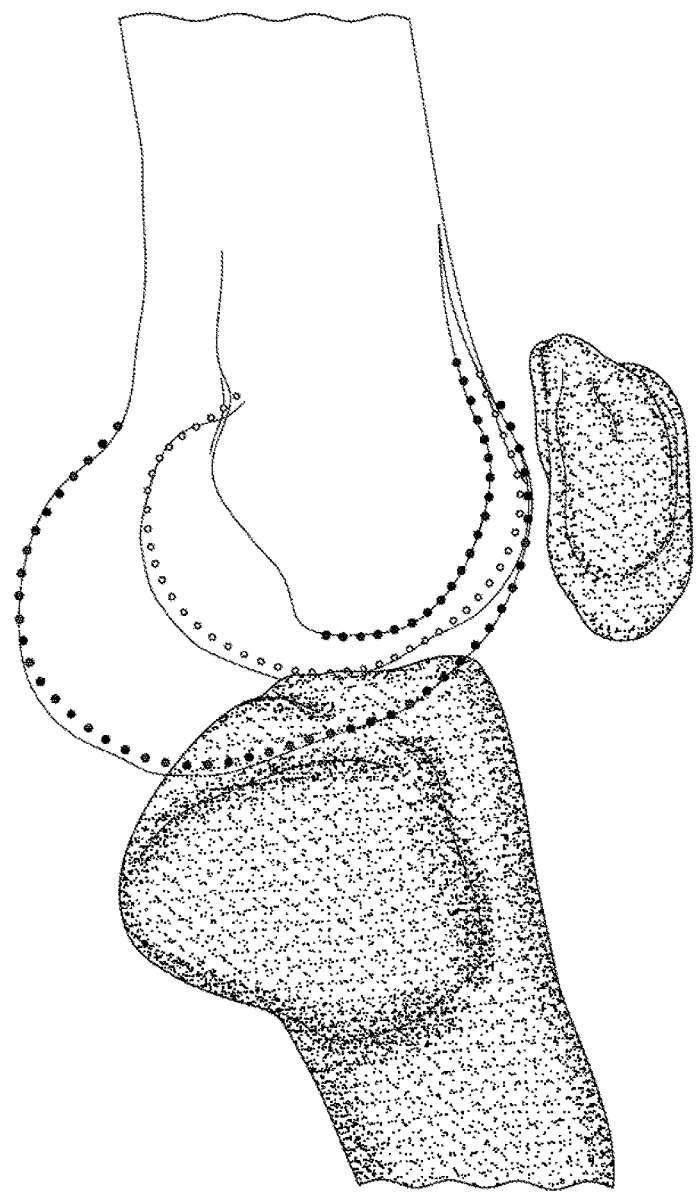
FIG. 20 is a lateral profile view of a knee joint showing the tibia and patella of FIG. 18, as well as the camming paths and trochlear groove path, in addition to showing the distal femur in phantom.

Referring to FIGS. 17-20, after each 3D model 300 has been generated and saved, a series of radii of curvature measurements are taken for both the medial and lateral condyles 308, 310 associated with each 3D model. In exemplary form, a distal femoral 3D model includes corresponding medial and lateral condyles 308, 310 separated by a trochlear groove 312. Each lateral and medial condyle 308, 310 includes a camming surface having points along the camming surface that are farthest away from the center of the bone as the femur rotates through its range of motion. In order to calculate medial profile, a plane defined by the medial anterior point (most anterior point in medial condyle), the medial distal point (most distal point on medial condyle) and the medial posterior point (most posterior point in medial condyle) is intersected with the distal femora this results in contour that corresponds to the most protruding points on medial condyle surface, the same method is used to calculate the lateral profile as shown in FIGS. 17, 19 and 20. These 3D paths are then converted to a single best-fit path within one plane for each condyle.

For the sulcus profile calculation, a set of contours is extracted by intersecting the distal femur with a series of planes rotating around the transepicondylar axis with a 10 degree increment. The lowest points on these contours are then used to define the sulcus points as shown in FIG. 19.

A similar procedure is utilized to generate a set of points along a 3D path of the trochlear groove using the points along the surface that are closest to the center of the bone as the femur rotates through its range of motion. These closest points (i.e., lowest portion of the trough) are shown in FIGS. 19 and 20. This 3D path is then converted to a single best-fit path within one plane (as shown in FIGS. 19 and 20).

Figure 22:
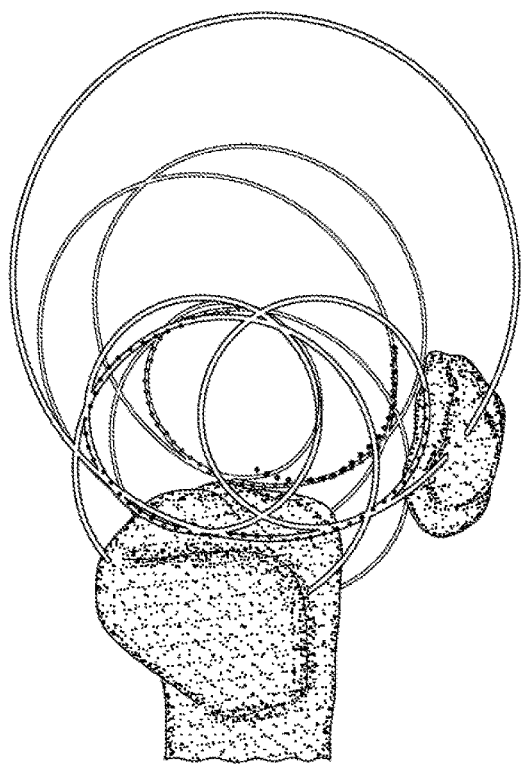
FIG. 22 is a lateral profile view of a knee joint showing the tibia and patella relative to the positions and size of corresponding radii of curvature for the outermost camming surface paths of the lateral and medial condyles.

Referring to FIGS. 21 and 22, the inventors of the present invention have found that the shape of the 2D paths for both the medial and lateral condyle bearing surfaces, as well as the 2D path for the trochlear groove, are important in attempting to design a prosthetic femoral component that closely resembles the natural shape of the distal femur. In order to generate specific sizing and curvature measurements for generation of the femoral component, the inventors have found that application of four radii of curvature to each femoral condyle accurately resembles the curvature of the natural femur condyles.

Figure 23:
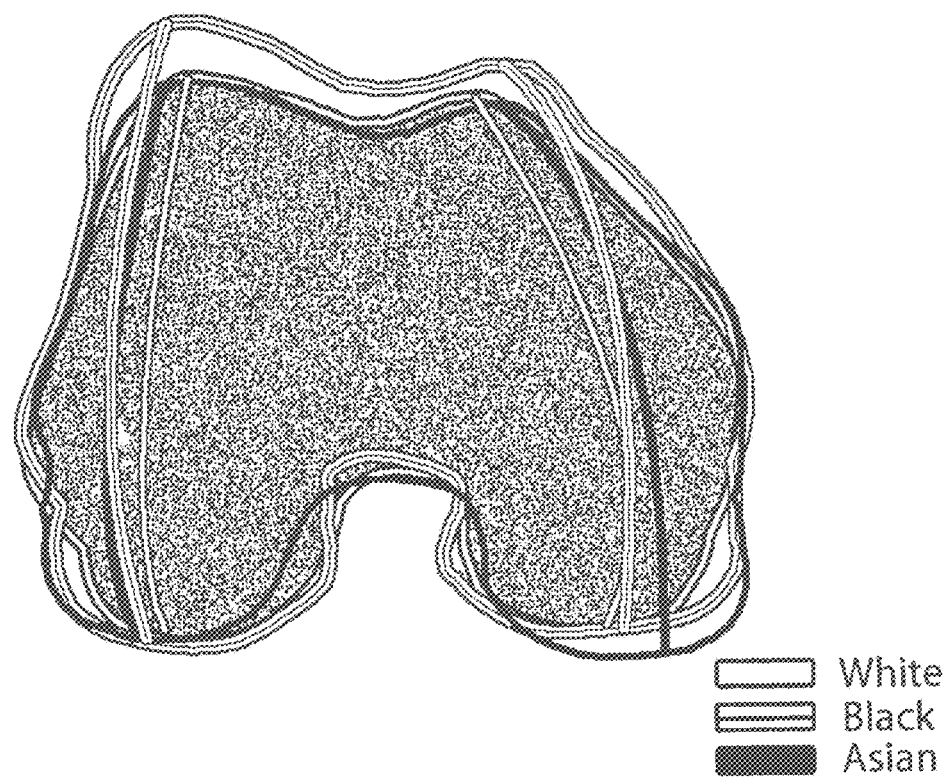
FIG. 23 is a frontal view showing a common differences between the shape of a distal femur among Asians, American Whites, and American Blacks.
Figure 24:
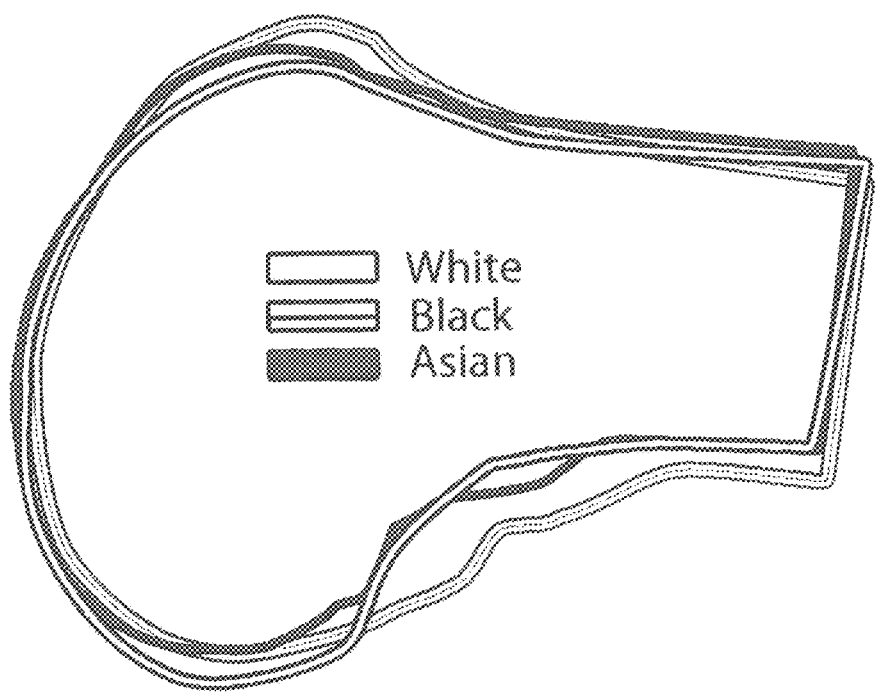
FIG. 24 is a profile view showing a common differences between the shape of a medial femoral condyle among Asians, American Whites, and American Blacks.
Figure 25:
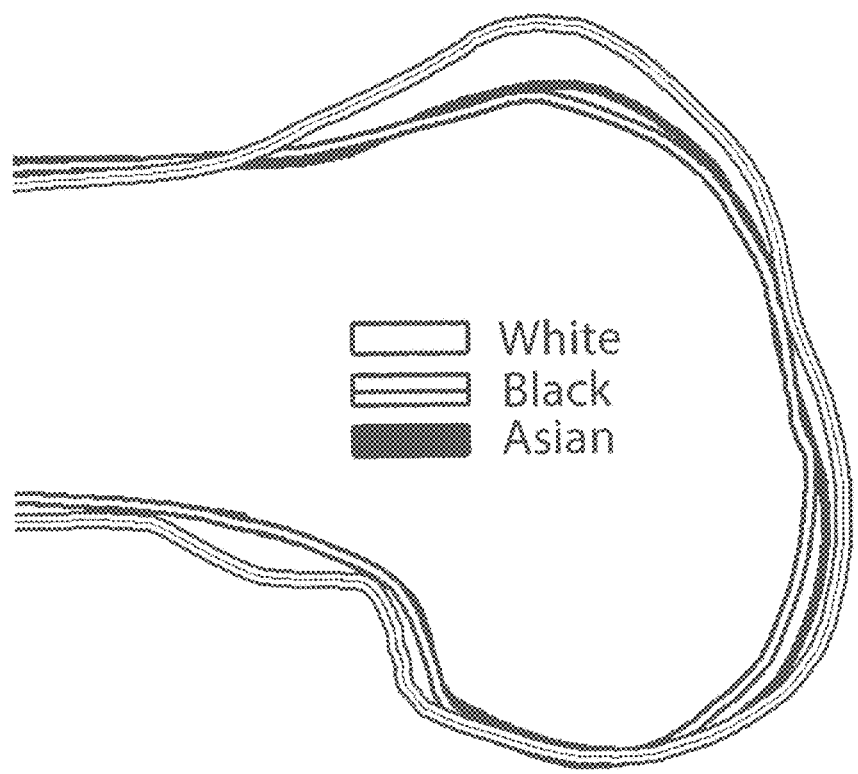
FIG. 25 is a profile view showing a common differences between the shape of a lateral femoral condyle among Asians, American Whites, and American Blacks.

Referencing FIGS. 23-25, FIG. 23 is a composite view of the lateral and medial femoral condyles for the Whites, Blacks, and Asians, whereas FIG. 24 shows the medial profile for a medial femoral condyle for Whites, Blacks, and Asians, and FIG. 25 shows the lateral profile for a lateral femoral condyle for Whites, Blacks, and Asians.

Figure 26:
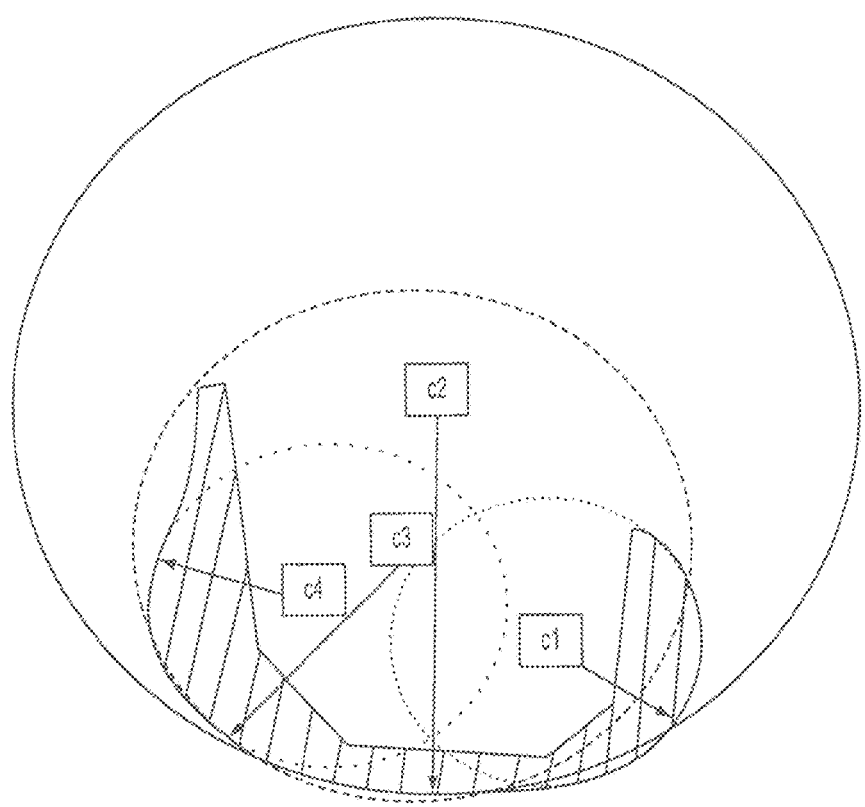
FIG. 26 is an exemplary profile cross-section of an exemplary lateral condyle prosthetic showing how the measurements of c1-c4 translate into the curvature of a prosthetic device fabricated in accordance with the instant disclosure.

Referring back to FIGS. 6 and 21, as well as FIG. 26, each path for the outermost medial condyle camming surface and the outermost lateral condyle camming surface is segmented into four zones. It has been identified by the inventors that the curvature of each of these zones can be approximated by the curvature of a circle. In other words, each zone has a curvature that approximates the constant arc of a circle. For example, the first zone has a radius of curvature, identified as $c_1$. Simply put, this $c_1$ value is the radius of a circle that most closely approximates the curvature of this portion of the camming surface 2D path, which is the most posterior portion of the path. The second zone, immediately adjacent to the first zone, has a radius of curvature of $c_2$. Again, this $c_2$ value is the radius of a circle that most closely approximates the curvature of this second zone. The third zone follows the second zone and also includes a radius of curvature, $c_3$. Finally, the fourth zone, which approximates the contour of the anterior portion of each of the respective condyles, has a radius of curvature of $c_4$.

In the circumstances where a series of knee joints are electronically modeled from X-rays, CT scans, MRIs, etc., a comparison may be carried out to discern how the radii of curvature vary within each zone and across all zones. The chart in FIG. 21 is derived from actual 3D bone models derived from human X-rays, CT scans, MRIs, and/or ultrasounds. This chart includes mean radii of curvature in metric units (in centimeters) for each zone based upon gender. In addition to giving the mean radius of curvature for each zone, the table also represents the standard deviation for each zone to provide a quick comparison between the zones for the lateral and medial condyles.

Referring back to FIGS. 22 and 26, a profile view of a human knee joint removes the distal portion of the femur and replaces it with circles corresponding to the radii of curvature for each of the four zones ($c_1$-$c_4$) for both the medial and lateral condyles. This figure provides a representative view of what radii of curvature represent in terms of are and the relative sizes of the circles in relation to the adjacent anatomical features of the distal femur. As will be discussed hereafter, these circles are relevant in attempting to approximate the curvature of a native distal femur in a prosthetic implant. The locations of the centers of the circles may be used inside an exemplary model. They may be calculated using linear square fitting of a circle in each set of curve points, which gives radii and centers of best approximating circles for the curves.

Figure 27:
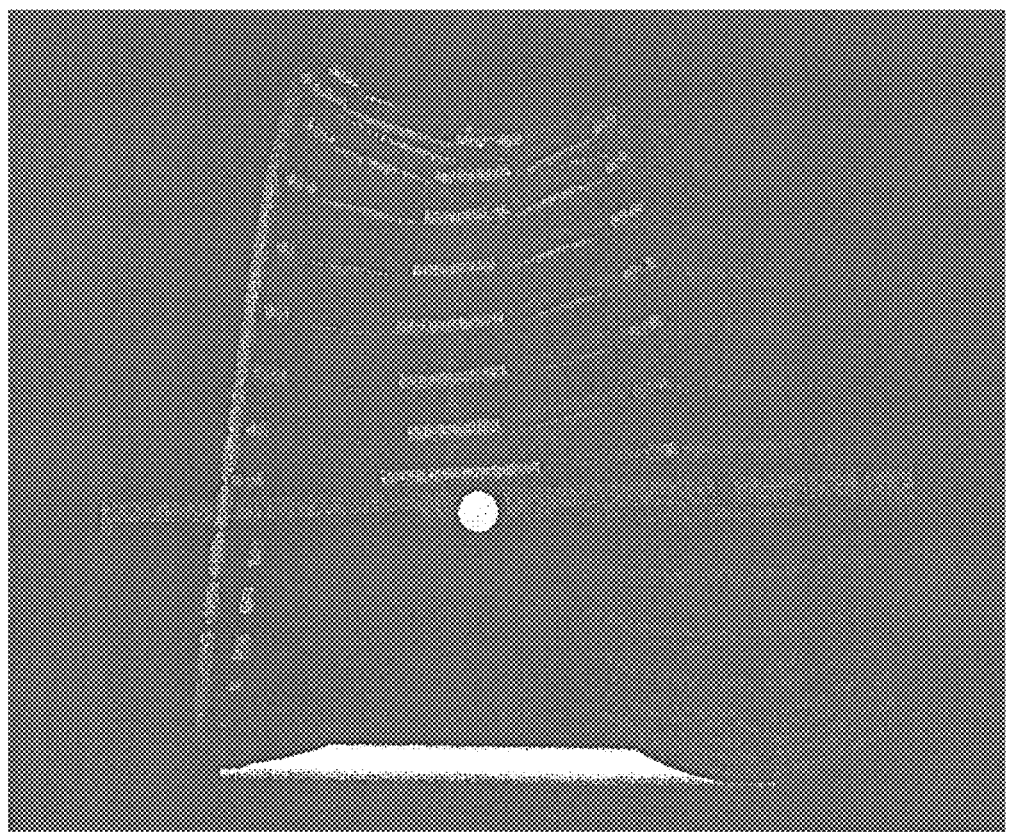
FIG. 27 is a 3D representation showing the outermost camming surface paths of the lateral and medial condyles for an exemplary distal femur, as well as the innermost path of the trochlear groove, in addition to the arcuate profiling of the lateral and medial condyles and the trochlear groove.
Figure 28:
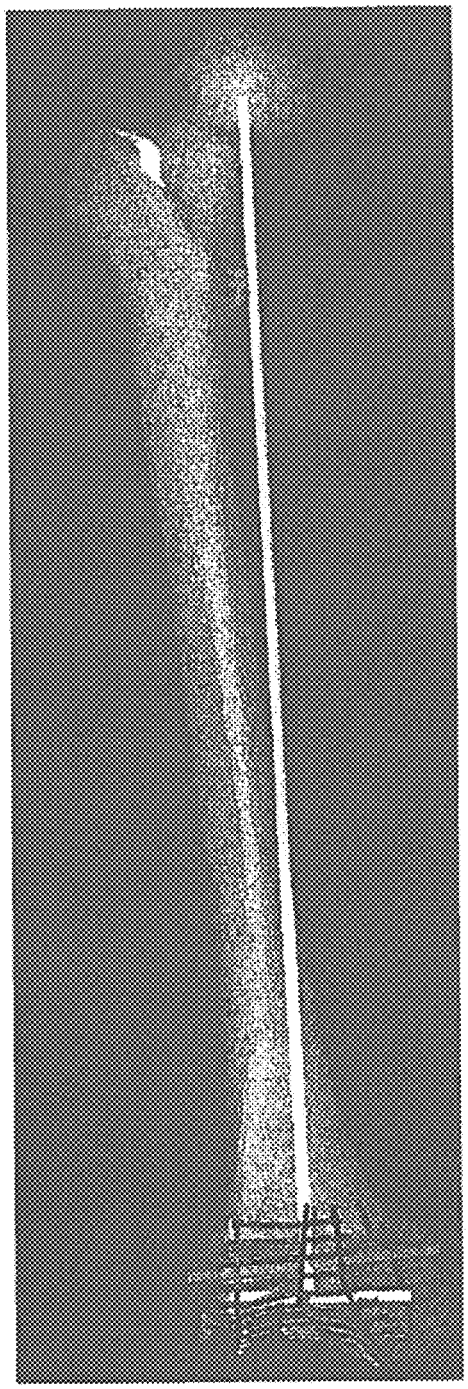
FIG. 28 is the 3D representation of FIG. 22 overlaid onto a 3D bone model of a natural femur.
Figure 29:
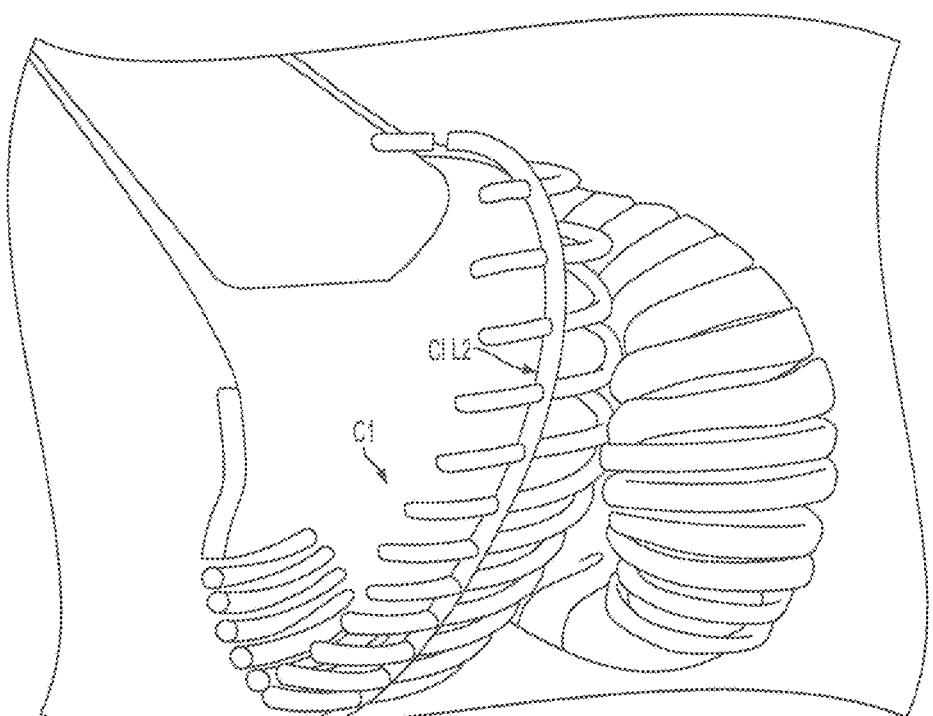
FIG. 29 is a magnified view of FIG. 23 showing the distal portion of the femur and the overlaid 3D representation.
Figure 30:
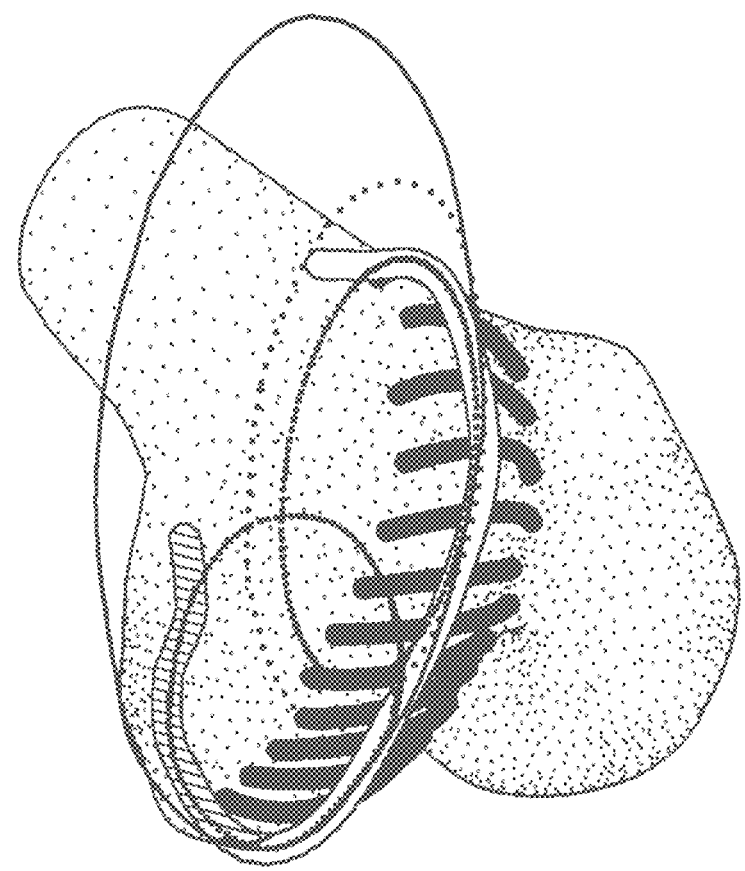
FIG. 30 is a perspective view of a distal portion of a femur including an exemplary 3D representation of the surface.
Figure 32:
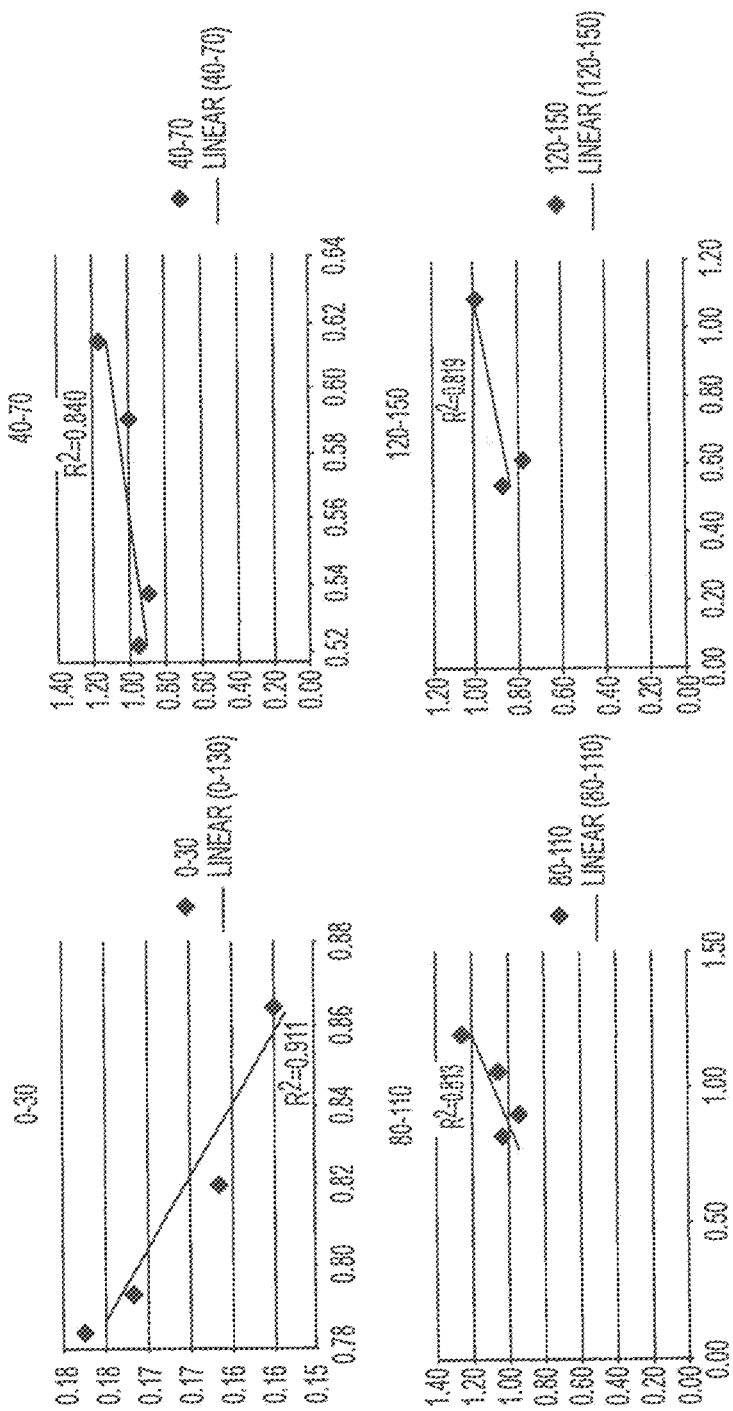
FIG. 32A is a graphical image plotting the ratio of the medial and lateral condyles to one another for 0-30 degrees.
FIG. 32B is a graphical image plotting the ratio of the medial and lateral condyles to one another for 40-70 degrees.
FIG. 32C is a graphical image plotting the ratio of the medial and lateral condyles to one another for 80-110 degrees.
FIG. 32D is a graphical image plotting the ratio of the medial and lateral condyles to one another for 120-150 degrees.

Referring to FIGS. 27-32, as discussed above, 3D paths are created that track the outermost camming points throughout the range of motion for both the medial and lateral condyles, as well as the innermost points throughout the range of motion of the trochlear groove. Each outermost camming path is utilized in conjunction with the path for the trochlear groove to mathematically map the topography of both condyles and the trochlear groove. Curvature of the medial, lateral and sulcus profiles are then calculated by finding best number of circles passing that accurately approximate the curve as shown in FIG. 27. To capture the curvature of the condylar surface, the curves produced earlier by intersecting the femur with the planes around TEA are trimmed around the medial, lateral and sulcus profiles, the circle of curvature of each of these trimmed contours are then calculated as shown in FIG. 27.

Each outermost condyle camming path, in addition to the trochlear groove trough path, is divided into variable degree increments along the range of motion of the distal femur as it rotates with respect to the tibia. In the images provided, ten degree increments were used, although other increments are within the scope of the disclosure (e.g., 5-15 degree increments may be employed in some exemplary embodiments). The length of each path is divided into ten degree increments, with a curve being applied at the boundary of each increment. A separate medial-lateral curve is applied to the widthwise portion (medial to lateral) of each condyle and the trochlear groove at each ten degree increment. The arch of each separate medial-lateral curve is chosen to most closely approximate the medial-lateral curvature at each point along the respective paths. Thereafter, a radius of curvature is determined for each medial-lateral curve.

Figure 33:
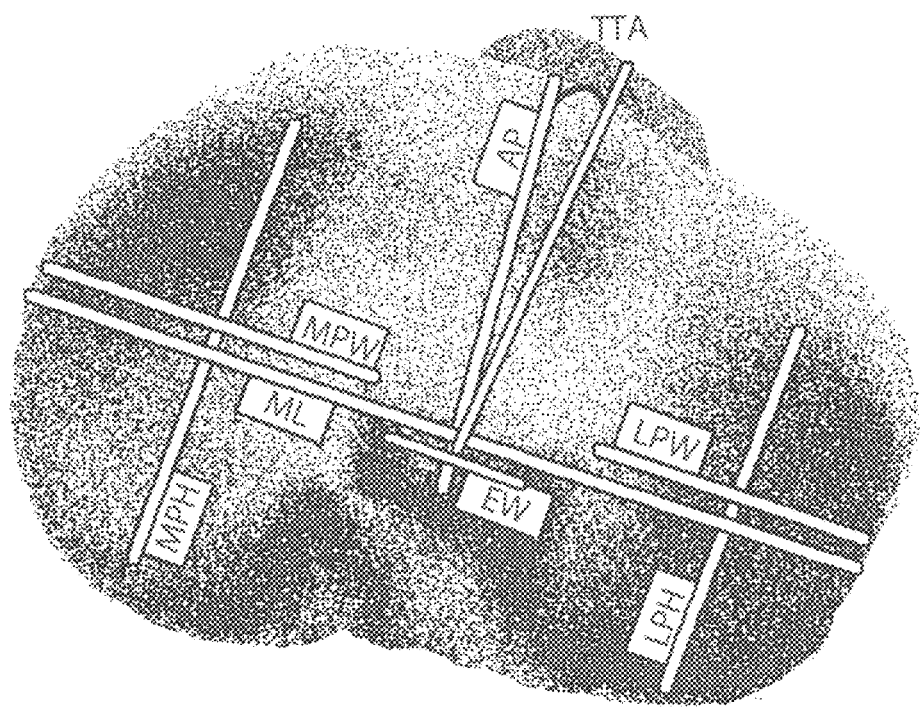
FIG. 33 is a proximal end of a tibia showing the axes, landmarks, and measurements taken in accordance with the instant disclosure.

Referring to FIG. 33, the following landmarks and measurements were identified automatically for the distal femur:
1) Intercondylar Eminence Points—The two highest projecting points on the medial and lateral intercondylar eminences.
2) Eminence Midpoint—The midpoint between the lateral and medial intercondylar eminence points.
3) Tibial Tuberosity—The most anteriorly protruding point on the tibial tuberosity.
4) ML—Maximum width of the tibia plateau in the medial-lateral direction.
5) AP—Length of the tibial plateau in the anterior-posterior (AP) direction and passing through the midpoint of the tibial intercondylar eminence (i.e. eminence midpoint).
6) Eminence Width (EW)—Distance between medial and lateral intercondylar eminence points.
7) Tibial Twist Angle (TTA) Angle between the AP direction and a line connecting the intercondylar eminence midpoint and tibial tuberosity.
8) Lateral Plateau Height (LPH)—Length of the lateral tibial plateau in the AP direction.
9) Lateral Plateau Width (LPW)—Length of the lateral tibial plateau in the ML direction.
10) Medial Plateau Height (MPH) Length of the medial tibial plateau in the AP direction.
11) Medial Plateau Width (MPW)—Length of the medial tibial plateau in the ML direction.
12) Eminence ML Ratio (EMLR) Ratio of MPW (i.e. medial plateau width) over ML.
13) Maximum Length—Length of the tibia from the medial malleolus to the intercondylar eminence.

Figures 34A, 34B, 34C:
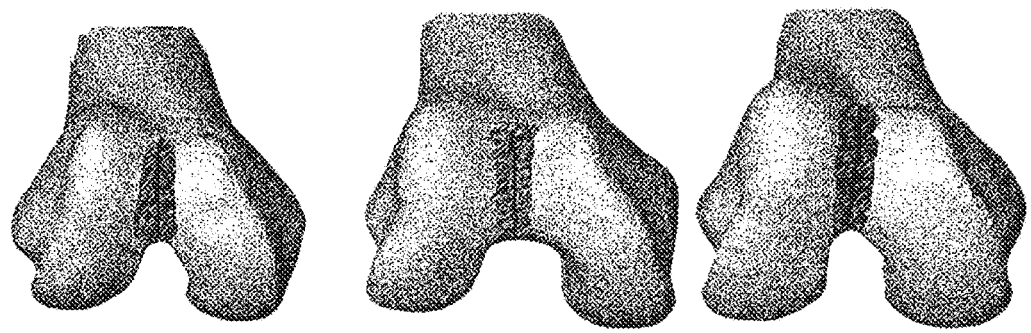
FIG. 34A is an end view of a distal femur showing the trochlear path of a typical Asian.
FIG. 34B is an end view of a distal femur showing the trochlear path of a typical American White.
FIG. 34C is an end view of a distal femur showing the trochlear path of a typical American Black.
Figures 35, 36:
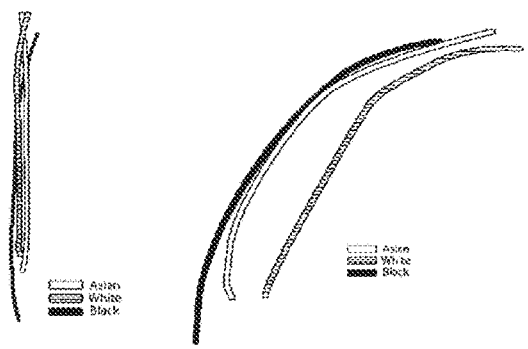
FIG. 35 is a composite view showing the trochlear paths for a typical Asian, American White, and American Black.
FIG. 36 is a composite profile view showing the shape of trochlear paths for a typical Asian, American White, and American Black.
Figure 37:
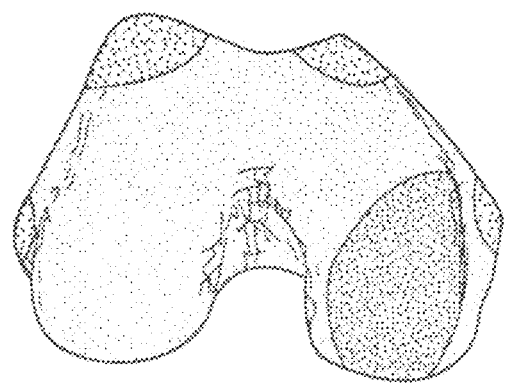
FIG. 37 is a distal view of a femur showing areas of maximum difference between an Asian and an American White.
Figure 38:
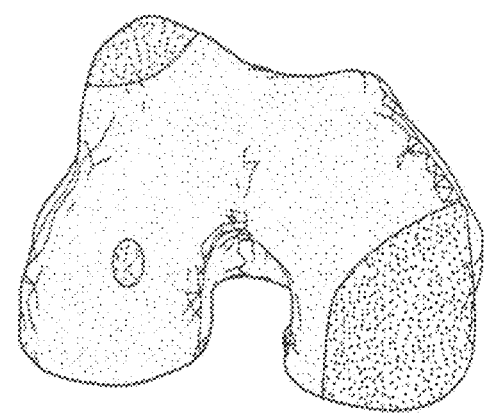
FIG. 38 is a distal view of a femur showing areas of maximum difference between an American White and an American Black.
Figure 39:
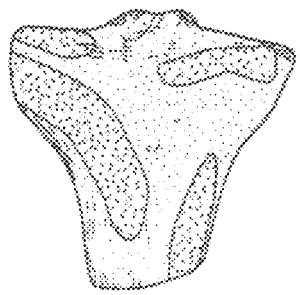
FIG. 39 is a elevated perspective view of a tibia showing areas of maximum difference between an American White and an American Black.
Figure 40:
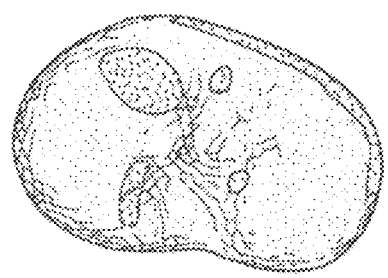
FIG. 40 is a proximal view of a tibia showing areas of maximum difference between an Asian and an American White.

Referring to FIGS. 34A-36, it can be seen that the trochlear groove for different ethnicities has a different shape and path. FIG. 34A represents the trochlear groove path for a typical Asian, while FIG. 34B represents the trochlear groove path for a typical American White, while FIG. 34C represents the trochlear groove path for a typical American Black. In addition, FIG. 35 provides a composite view of the trochlear groove path for a typical Asian, a typical American White, and a typical American Black. Finally, FIG. 36 provides a profile view showing how the shape of the trochlear groove also varies among Asians, American Whites, and American Blacks. The results from the feature finder shape analysis tool, as described above, highlight shape differences in the femoral shaft, lateral condyle, and greater trochanter, in addition to the distal femur.

Referring to Table 1 and FIGS. 37-40, the results from the t-tests and power tests for the automated measurements. In American Blacks, the lateral condyle has higher AP height ($p<0.01$) whereas the medial condyle height wasn't significant, thereby creating a more trapezoidal-shaped knee as opposed to the more square-shaped knee in American Whites which resulted in larger AP condyle angle in American blacks. On the other hand, our analysis performed on the distal femur of the East Asian population identified a distinct pattern in the AP and ML where the AP and ML measurements are smaller in the East Asian population as compared to both the Caucasian and African American populations ($p<0.01$). In general, the Asian population exhibits a more trapezoidal shape than the Caucasian and African American populations ($p<0.01$). In addition, the East Asian population also has a narrower anterior width ($p<0.01$).

Figure 6:
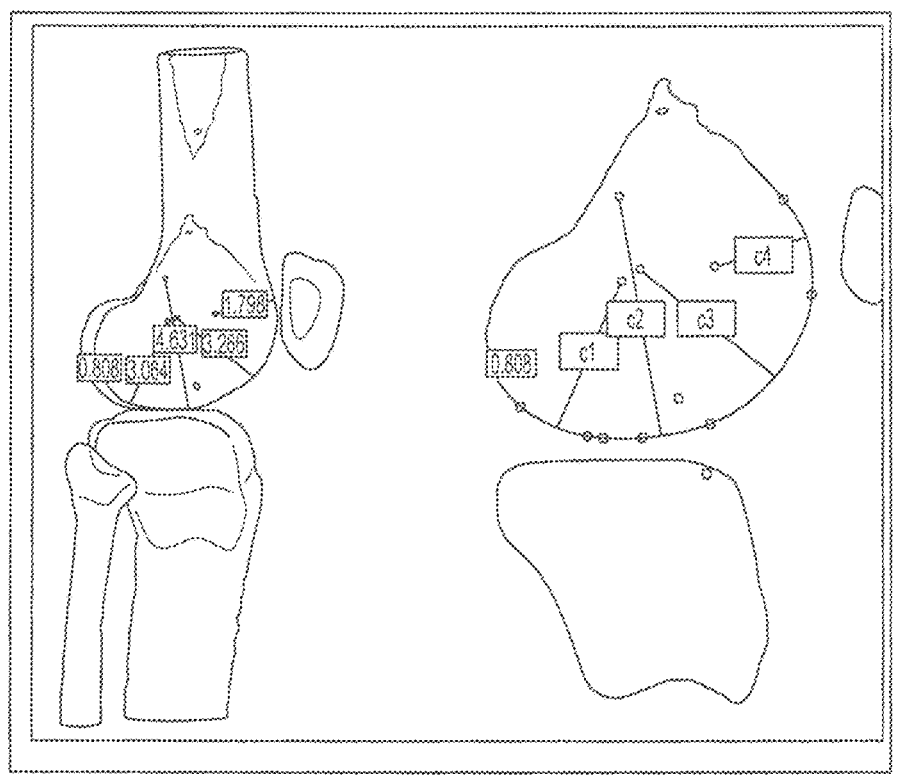
FIG. 6 is a profile view of the lateral condyle of a human knee joint having five radii of curvature applied to approximate the curvature of the camming surfaces from anterior to posterior.
Figure 7:
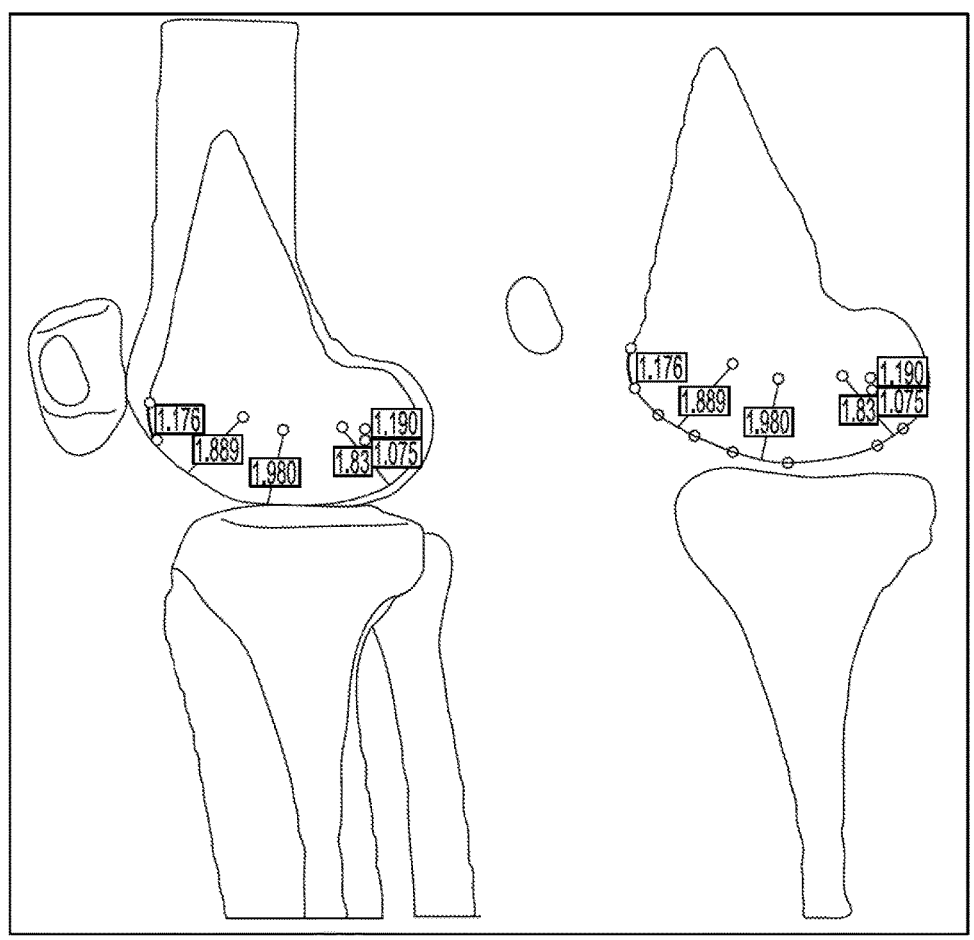
FIG. 7 is a profile view of the medial condyle of a human knee joint having five radii of curvature applied to approximate the curvature of the camming surfaces from anterior to posterior.
Figure 8:
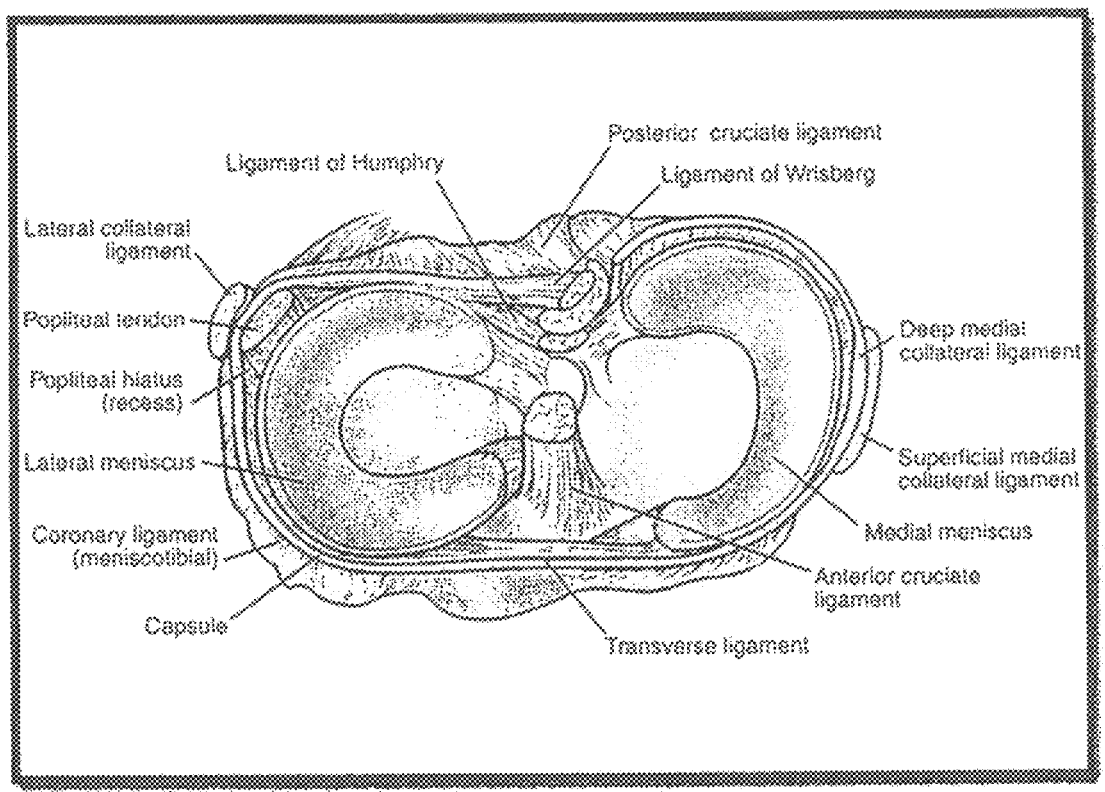
FIG. 8 is a plan view of the proximal end of a human tibia that includes cartilage forming a portion of a human knee joint.
Figure 9:
FIG. 9 is a frontal view of a knee joint showing the anterior cruciate ligament and posterior cruciate ligament during partial knee flexion.
Figure 10:
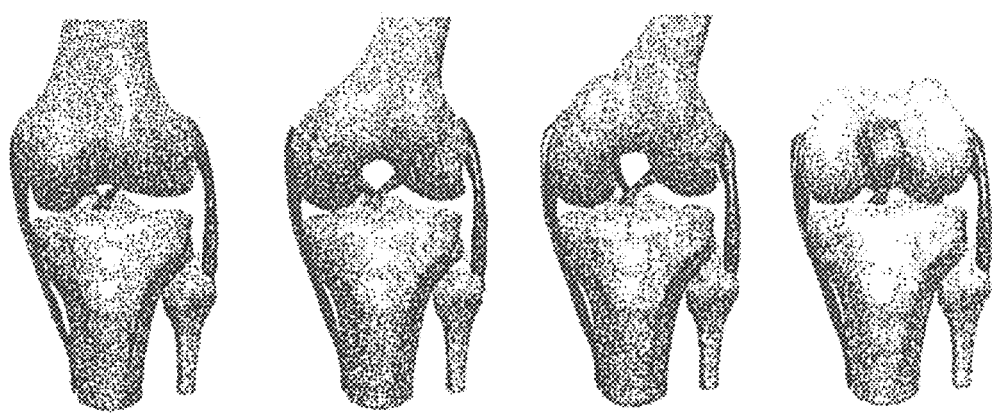
FIG. 10 includes a series of frontal views of a knee joint at various degrees of knee flexion showing the position of the anterior cruciate ligament and the posterior cruciate ligament.

Analyzing the curvature of both lateral and medial profiles it has been found that they can be accurately approximated by four distinct radii of curvature for American black and American white and three distinct radii for East Asians (see FIG. 6). These four radii were found to be consistent between both ethnicities (American Black and American White), however the value of these radii were different in each ethnicity as shown in FIGS. 23-25.

The feature finder results for the tibia indicate that ethnic shape differences between American white and American black are not as significant at the medial and lateral plateau areas as opposed to more shape differences around tibial tuberocity area. Besides minor differences in the proximal anterior tibia, the only area that registered significant was the tip of the medial malleolus (see FIGS. 39 and 40). However, a major shape difference was found between East Asian population and both American White and American Black (FIGS. 23-35). The results from the t-tests and power test underscore these findings, as well. The most significant variables are those related to scale, including maximum length, measures of shaft robusticity, and several measurements of the tibial plateau. In short, American Black tibiae are longer with a more robust shaft and slightly larger tibial plateau.

Table 2 shows the automated measurements for the tibia with lateral plateau height as the most significant measurement ($p<0.05$) which correlates to the significant difference in the lateral femoral condyle height.

Referring back to FIG. 31, the radii of curvature for the medial-lateral curves are determined for both the medial condyle and the lateral condyle at each ten degree increment, from posterior to anterior. The first column is structured in ten degree increments along each outwardmost camming surface path for both the medial and the lateral condyles. The second and third columns refer to the radius of curvature for the medial and lateral condyles at the respective angle increments. The final two columns are ratios corresponding to the curvature of the medial-lateral radius of curvature divided by the radius of curvature for the respective camming surface paths. In other words, the ratio has a numerator that is the radius of curvature from side to side of each condyle, and a denominator that is the radius of curvature for the zone (which is the same number for a zone) along the path of the outermost camming surface of each condyle. This ratio is then plotted for each zone, for various planes taken at specific angles with respect to the mechanical axis (MA).

Figure 41:
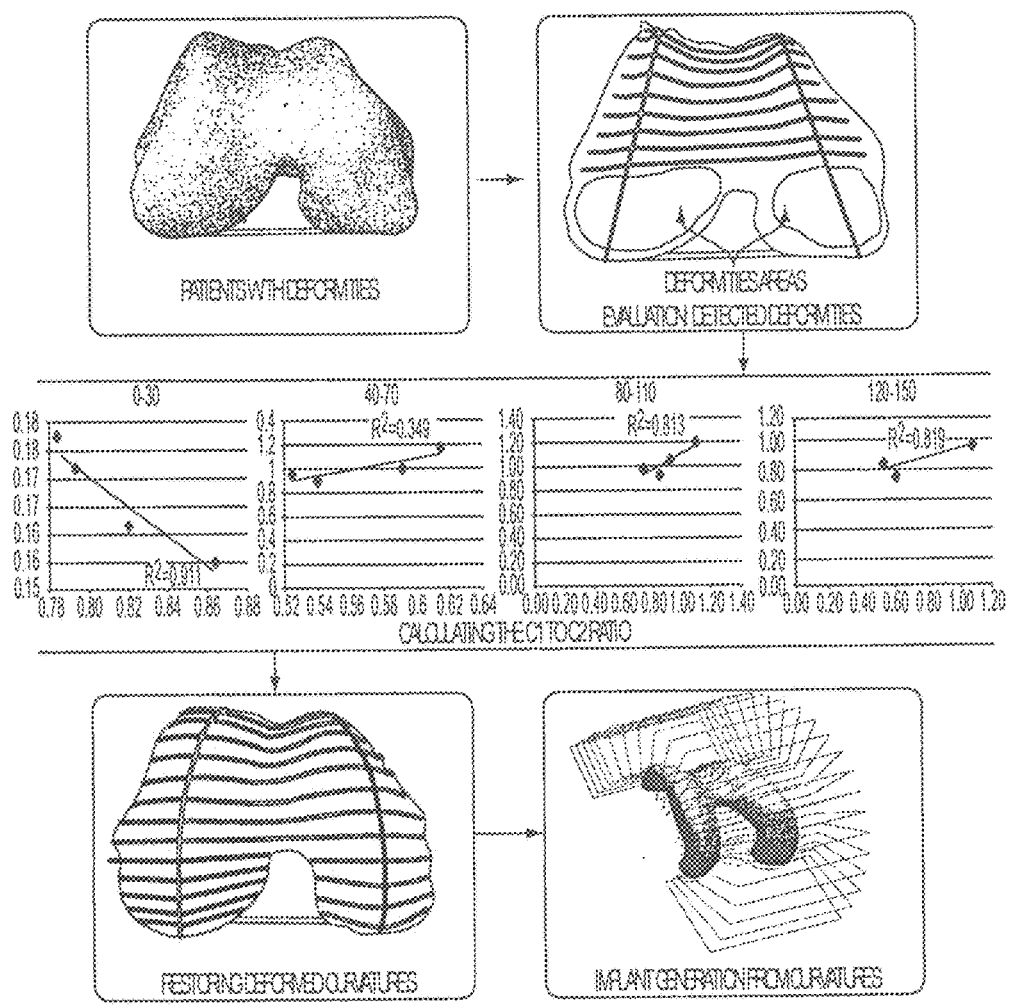
FIG. 41 is a diagram showing an exemplary process for restoring deformed or missing anatomy using C1/C2 ratio in accordance with the instant disclosure.

Referring to FIG. 41, the ratio of C1/C2 (see FIG. 29) can be used to restore deformed anatomy to generate a smooth articulating surface of patient specific implant. The process may begin by calculating lateral and medial profile and the curves for the condylar surface for the patient as outlined in the previous point, these contours are then evaluated to verify that the curvature of each sectional curve is within the normal anatomical range. Deformed sections are then highlighted and C1/C2 ratios are calculated for the anatomical correct sections, these sections are then used to interpolate the ratio for the deformed section, upon completion of this process a smooth implant articulating curvature that mimics the patient correct anatomy is generated.

The results are utilized to approximate the radii of curvature along the condyles, C2, when abnormalities exist within the bone. A relationship between ratios of C1 and C2 for the medial and lateral condyles has been identified and can be used calculated the radius of curvature for a specific location along either condyle, C2.

Using the radii of curvature for the outermost camming surface paths for the medial and lateral condyles, as well as the mapping of the curvature for the medial-lateral arcs, a novel prosthetic implant may be fabricated that is patient specific. At each degree increment, a smooth curve is generated using the radii of curvature and three points along the medial condyle, trochlear groove, and lateral condyle (see FIG. 29). The articular surface of the implant is then approximated using a sweep surface of these smooth curves.

Referring to FIGS. 41 and 26, four distinct radii of curvature have been identified for the outermost camming surface of the lateral and medial condyles.

Figure 42:
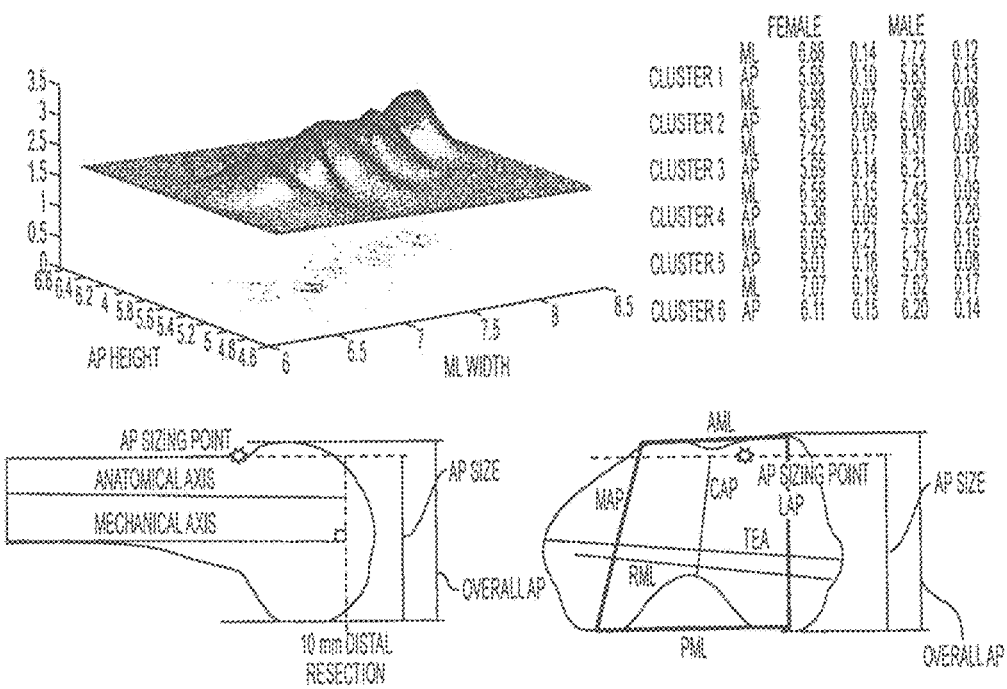
FIG. 42 is an exemplary plot of AP height versus ML width.
Figure 43:
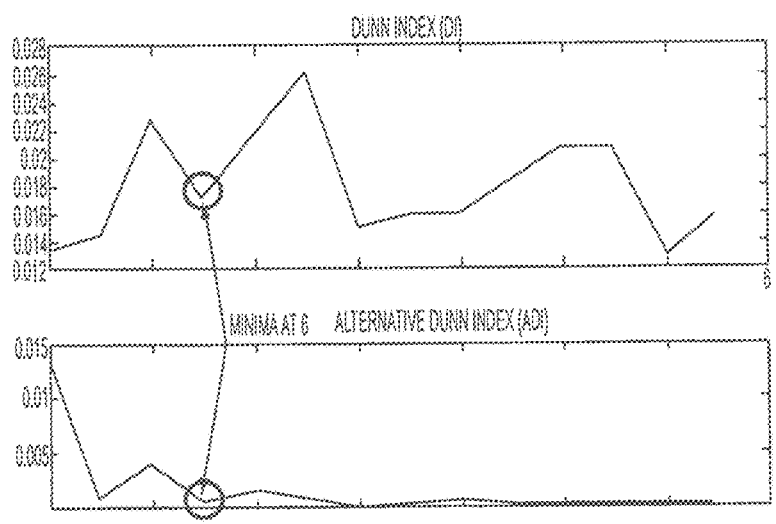
FIG. 43 is a plot for determining the optimum number of clusters using Dunn's Index and modified Dunn's Index.
Figures 44, 45:
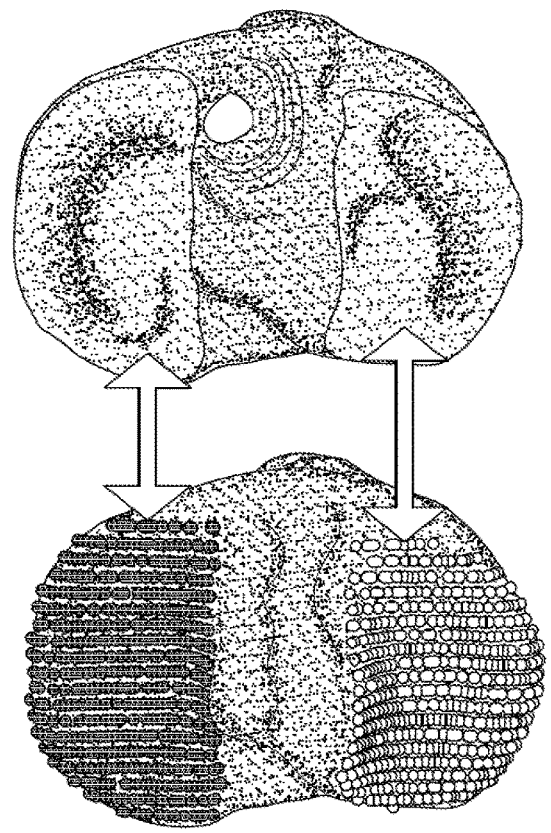
FIG. 44 is an alternative Dunn's Index Equation (ADI).
FIG. 45 is a collection of views depicting an exemplary approximation of a tibial plateau using a series of contours normal to the principal axes of the medial and lateral plateaus.

Referring to FIG. 42-44, six cutting box sizes were identified by analyzing the aspect ratio between the anterior-posterior height and ML Width. The AP height is defined as the distance between the sizing point and most posterior point on the femur while the ML width is defined as the size of the femur in the medial lateral dimension. This aspect ratio are then calculated for all population this ratio along with and not limited to features highlighted in table I are then used as a multidimensional feature vector to cluster the population, best number of clusters are determined using both Dunn's Index and alternative Dunn's Index (see FIGS. 43 and 44) which are used to identify of how compact and well separated the clusters are. In exemplary form, twelve clusters were found that best represent the American White population which are divided into six clusters for males and six for females)

Referring to FIG. 45, the tibial plateau is approximated using a series of contours normal to the principal axis of the medial and lateral plateau. These contours are used to parameterize the surface of the polyethylene for the tibial implant.

Figure 46:
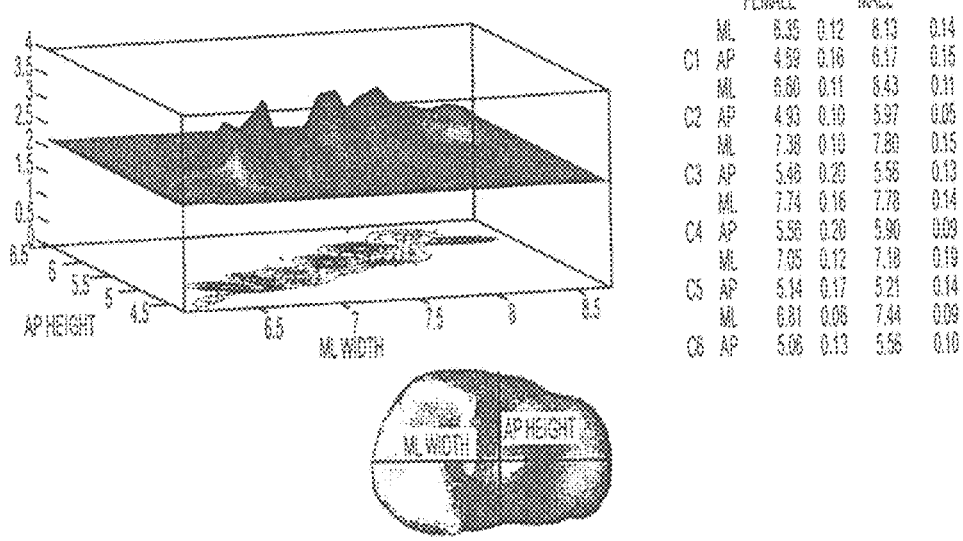
FIG. 46 is an exemplary plot of AP height versus ML width.
Figure 47:
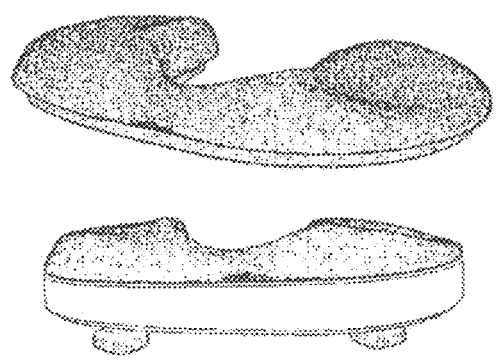
FIG. 47 is a perspective view of an exemplary polyethylene implant.
Figure 48:
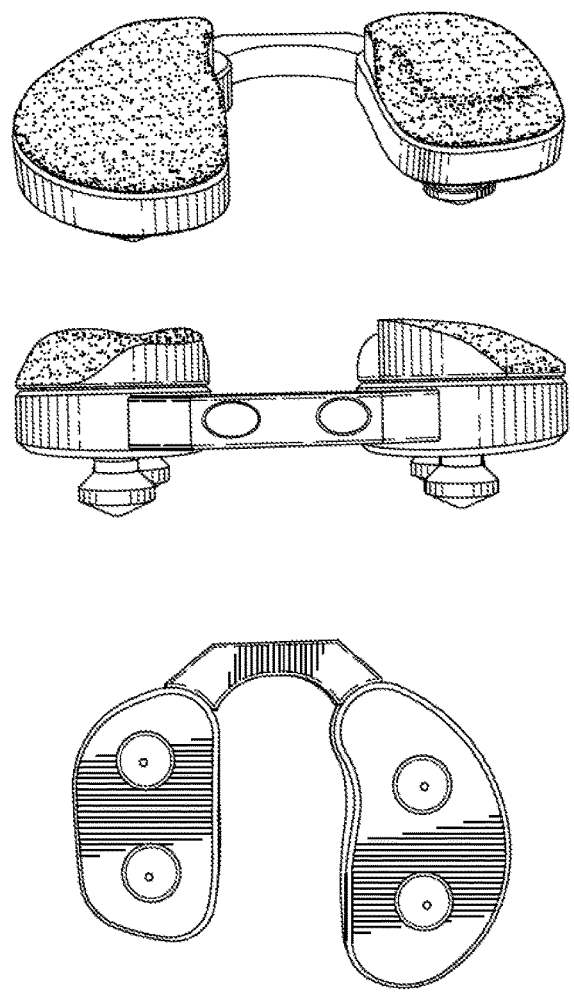
FIG. 48 is a series of perspective views of an exemplary implant.
Figure 49:
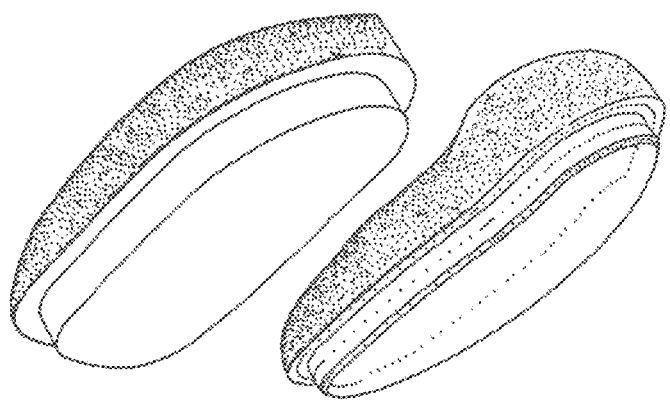
FIG. 49 is a perspective view of an exemplary implant.
Figure 50:
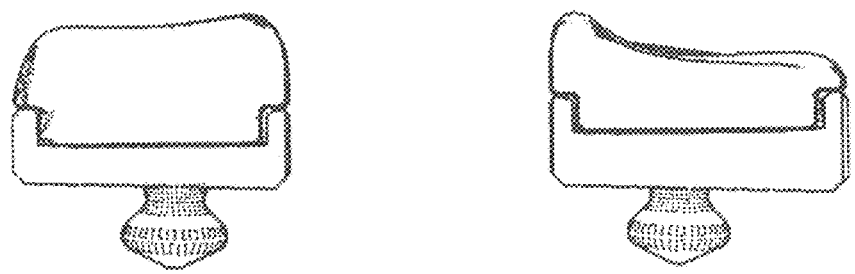
FIG. 50 is a cross sectional view of an exemplary implant.

Referring to FIG. 46, six tibial plate sizes were identified by measuring the length of the tibial surface in the anterior-posterior direction and measuring the tibia length in the medial-lateral direction. The ratio between these two measurements was then clustered using fuzzy c-means to identify six sizes the best fit the population.

Figure 51:
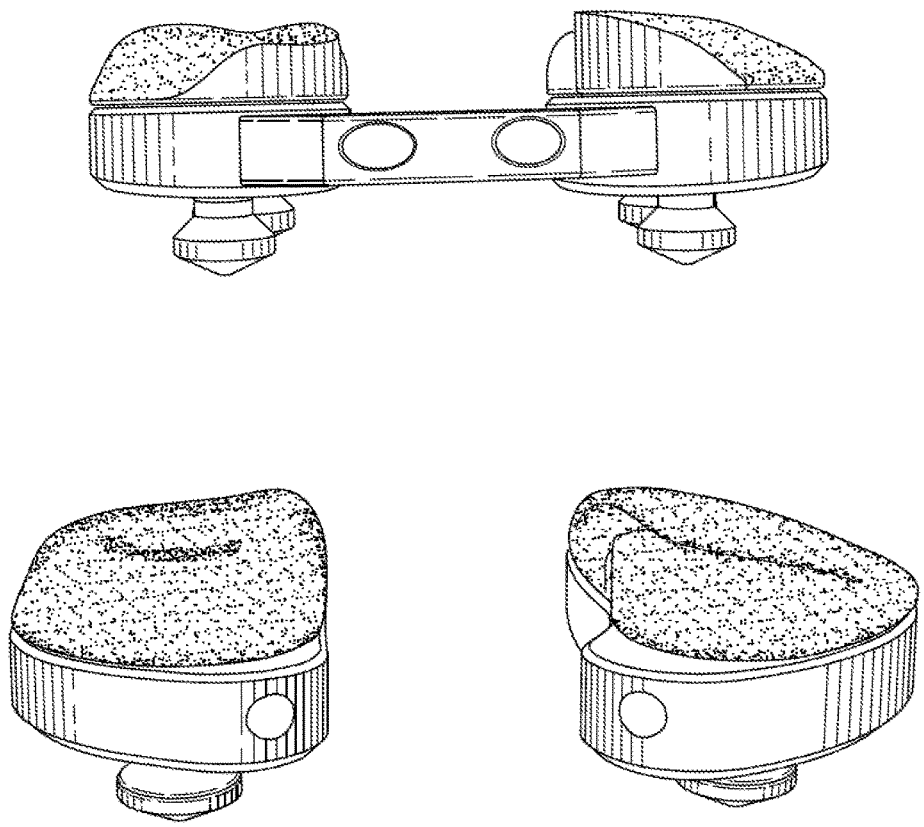
FIG. 51 is a perspective view of an exemplary implant.

Referring to FIG. 47-51, the polyethylene reflects the anatomical shape of the tibial plateau for a cruciate retaining implant (see FIG. 47) and for a bi-cruciate implant (see FIGS. 48-51). The polyethylene can also be modular and may include medial and lateral polyethylene inserts which preserve the tibial eminence. A connector is used (FIG. 39) to ensure the accurate placement of the inserts. Once secured, the connector is removed leaving only the medial and lateral polyethylene inserts and tibial trays in place (FIG. 51).

Figure 52:
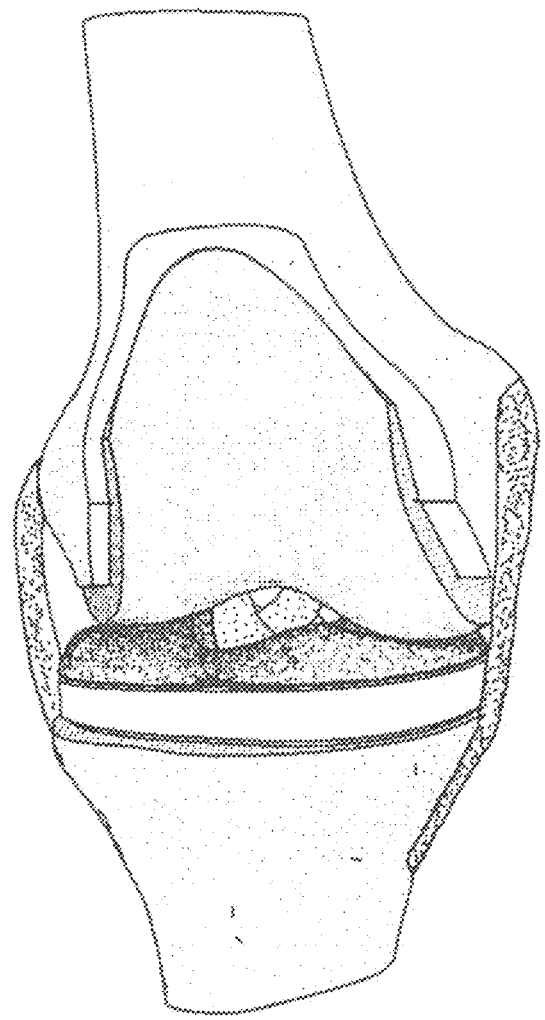
FIG. 52 is an anterior view of exemplary femoral and tibial components fabricated to correspond to the anatomical shape of the patient's knee for a cruciate retaining implant.
Figure 53:
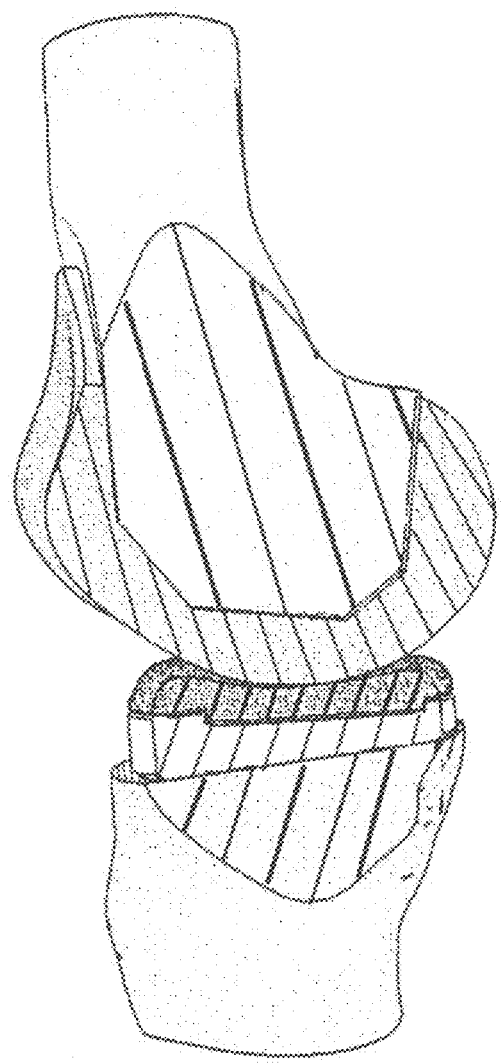
FIG. 53 is a cross-sectional view taken across the lateral condyle and condyle receiver for exemplary femoral and tibial components fabricated to correspond to the anatomical shape of the patient's knee for a cruciate retaining implant.
Figure 54:
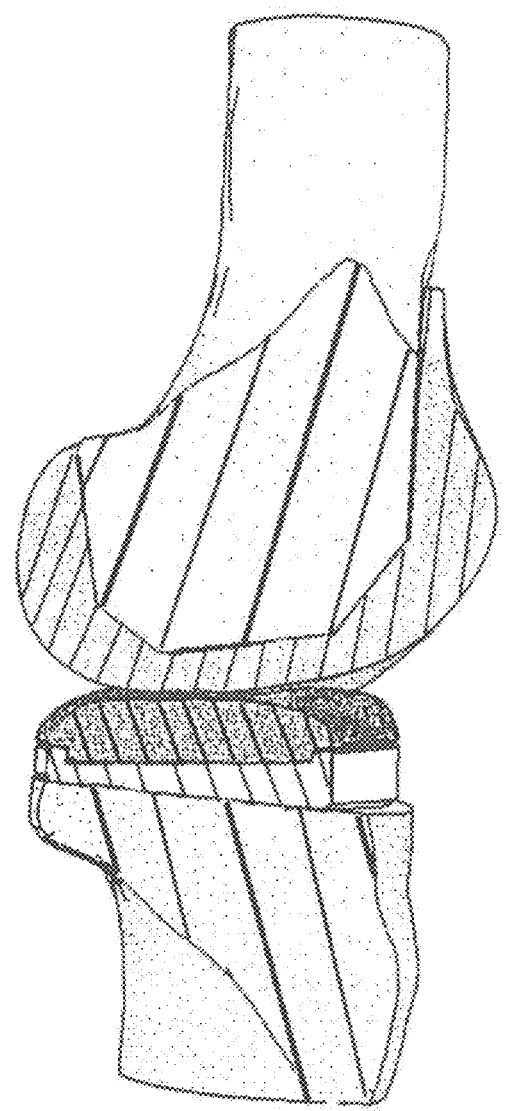
FIG. 54 is a cross-sectional view taken across the medial condyle and condyle receiver for exemplary femoral and tibial components fabricated to correspond to the anatomical shape of the patient's knee for a cruciate retaining implant.

Referring to FIGS. 52-54, the femoral and tibial components of the implant corresponding to the anatomical shape of the knee showing the curvature matching between the two components radii.

Figure 55:
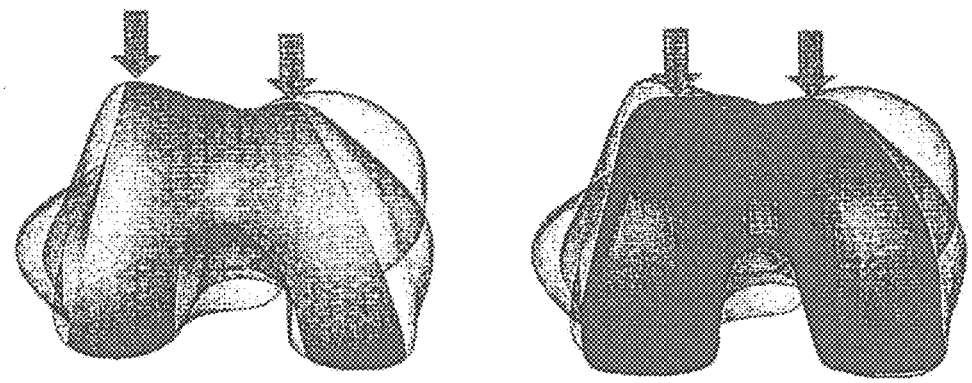
FIG. 55 is a comparison showing the difference between the anatomical implants and existing functional implants.
Figure 56:
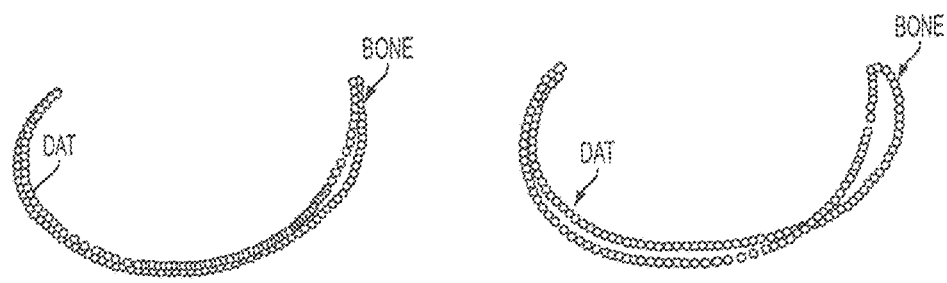
FIG. 56 is a comparison showing the difference in the restoration of the correct ratio between the medial and lateral anterior portions of the knee.
Figures 57, 58:
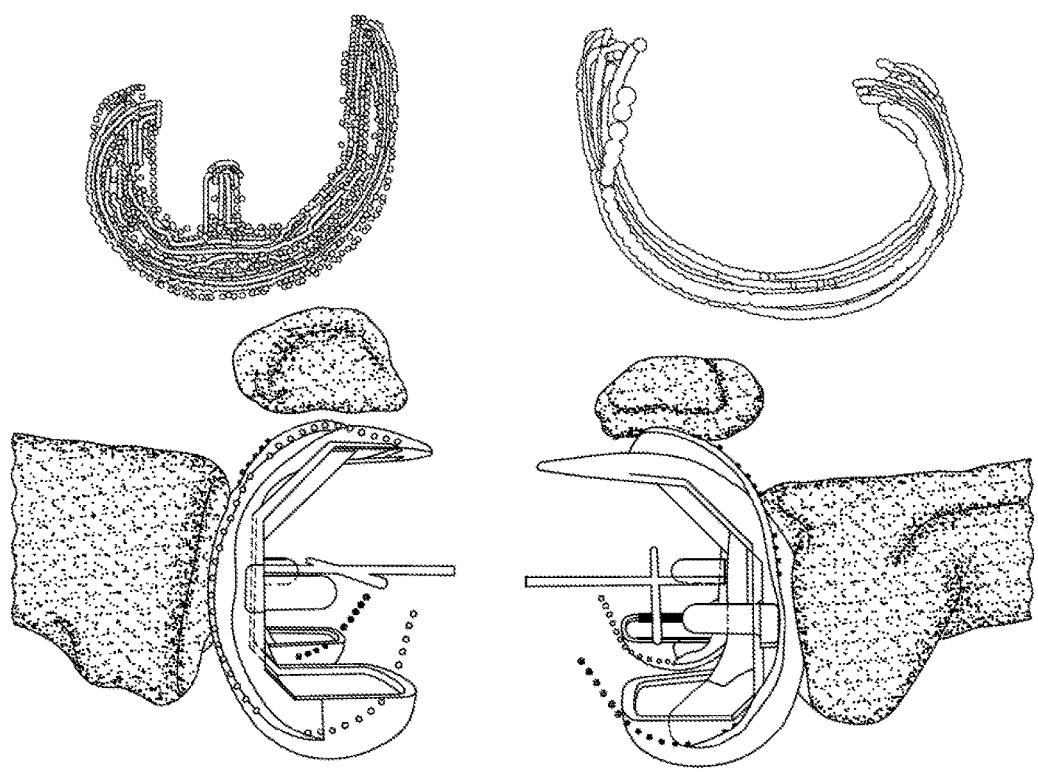
FIGS. 57 and 58 show the profiles of many functional implants.

Referring to FIGS. 55-58, a comparison shows the difference between the anatomical implants and existing functional implants. FIG. 55 shows the difference in the restoration of the correct ratio between the medial and lateral anterior portions of the knee. Existing functional implant (blue) does not properly restore this ratio causing more tension along the quadriceps which can alter the motion of the knee and can cause sublaxation of the patella. FIGS. 56-58 show the curvature of the medial and lateral profiles for the anatomical implant as compared to existing functional implants. FIG. 56 illustrates a direct comparison to a typical implant, whereas FIGS. 57 and 58 shows the profiles of many functional implants.

Figure 59:
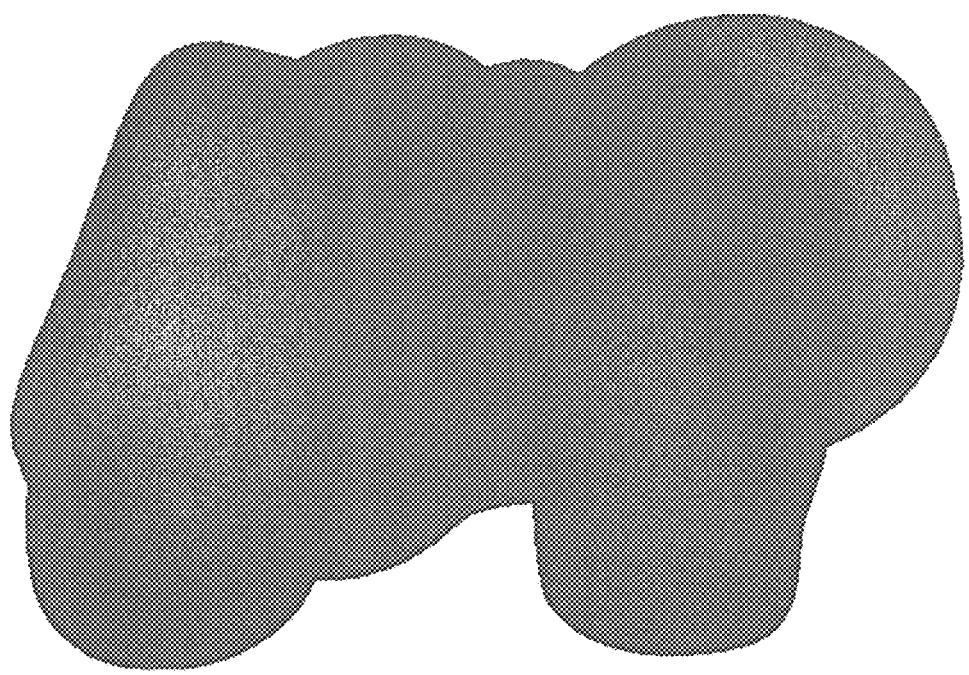
FIG. 59 is an exemplary shaded map showing the variation between African American and Caucasian populations, where less shading corresponds to greater differences, whereas more shading corresponds to less differences.

Referring to FIG. 59, the color map shows the variation between African American and Caucasian populations. The brighter colors show higher differences than darker colors. Little variation exists on the distal end of the femur although the lateral condyle does show slight differences.

An exemplary process of selecting a template that best fit patient anatomy can be described as following. A patient knee will first be imaged and a 3D surface of the patient femur and tibia will be generated. The femoral bone is then analyzed to calculate the medial and lateral camming paths. Medial and lateral sagital curves are then calculated. Anterior posterior size and medial lateral size of the femur are also calculated. The curvature of the camming paths along with the sagital curves, AP size and/or medial lateral width may be used to locate the best template that fit the patient. For patients where implant template doesn't fit their anatomy, a custom implant is generated as shown by the right branch of FIG. 11.

Figure 60:
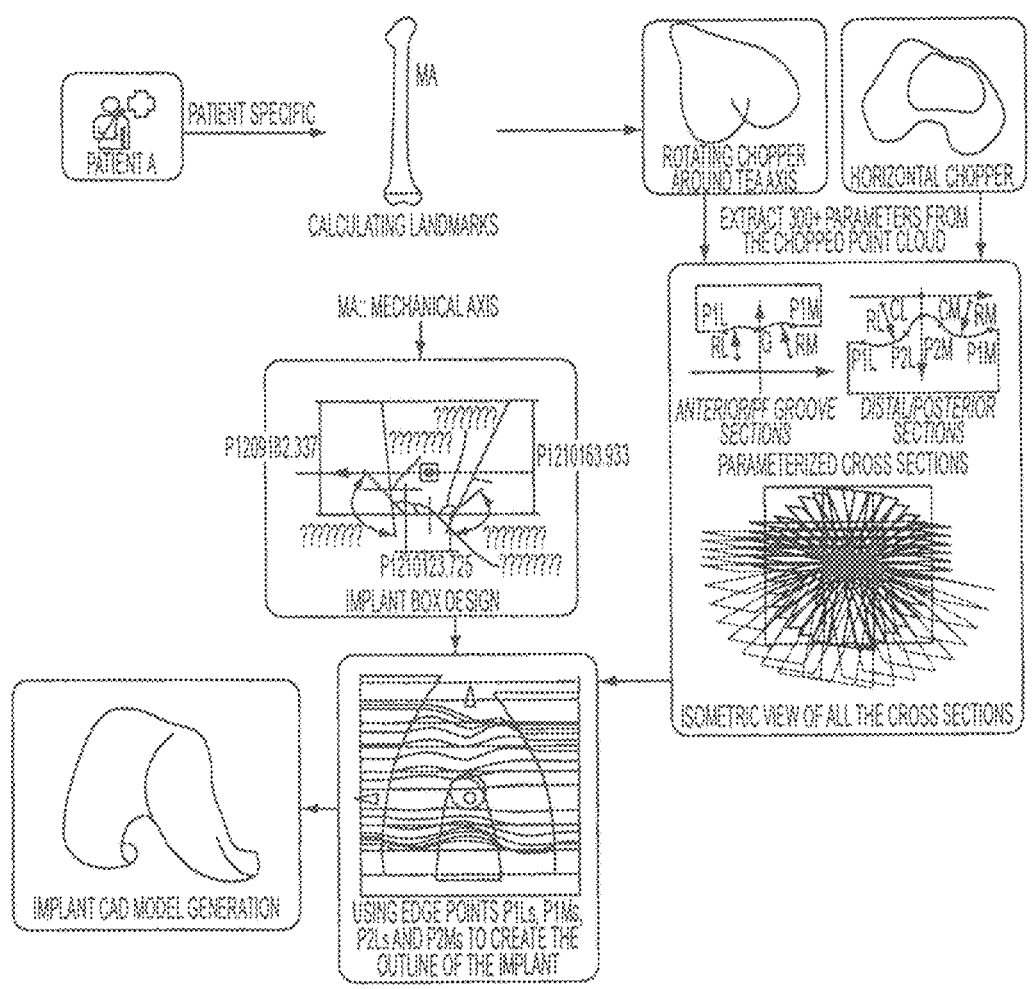
FIG. 60 is an exemplary flow diagram for generating a patient specific implant from the 3D bone model.

Referring to FIG. 60, an exemplary process for generating a patient specific implant from any imaging modality includes generating three dimensional patient specific models, these models are then added to the foregoing discussed (DAT) statistical atlas to achieve point correspondence and normalization, upon completion of this process relevant surgical landmarks are automatically calculated (TEA, MA, PCA, . . . etc).

Figure 61:
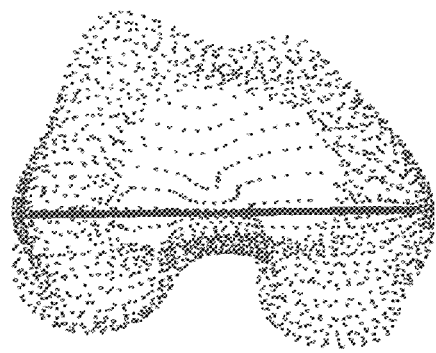
FIG. 61 is a depiction of the point cloud used to represent the surface of patient's bone and used to calculate bone cross sectional contours.
Figure 62:
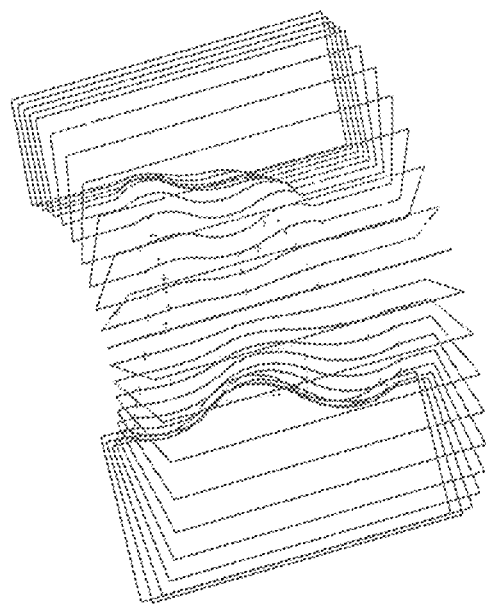
FIG. 62 is a depiction of updating parameterized implant constraints with the patient specific contours at an early stage of creation of a patient specific implant.
Figure 63:
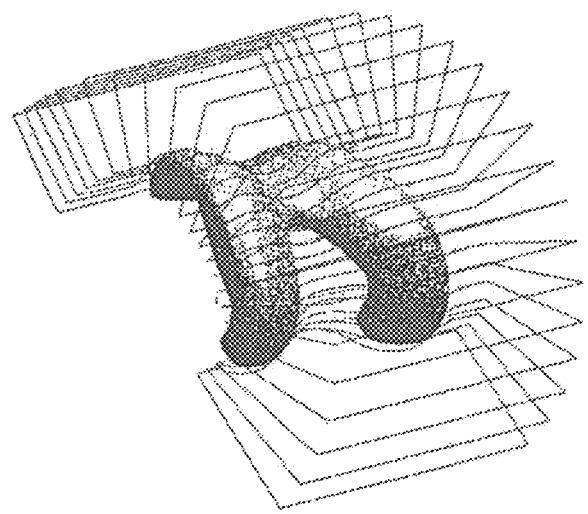
FIG. 63 is a depiction showing sweeping contours to generate smooth articulating implant surfaces that are patient-specific in accordance with the instant disclosure.

Referencing FIGS. 61-63, a rotating plane around the TEA is then used to calculate bone cross sectional contours (see FIG. 61) and another set of contours normal to the MA are then calculated (see FIG. 62). These two sets of contours are then used to update the constraints of the parameterized implant template automatically, upon updating of these constraints, the implant articulating surface is then swept to generate a smooth continuous surface (see FIG. 63). Measurements of the anterior-posterior height and medial-lateral width from the patient's bone are also used to update a template cutting box. This box is then combined with the smooth articulating surface to generate a patient specific implant CAD model. This implant 3D CAD model is then evaluated against the 3D model of the patient specific bone to verify the placement and a simulation of range of motion is performed with the 3D implant model and the 3D bone model. Upon completion of the verification process, the 3D implant model is output from a computer to a manufacturing facility in order to manufacture the implant. In exemplary form, the computer output of the 3D implant model may be in the form of G-code for a CNC machine.

Figure 64:
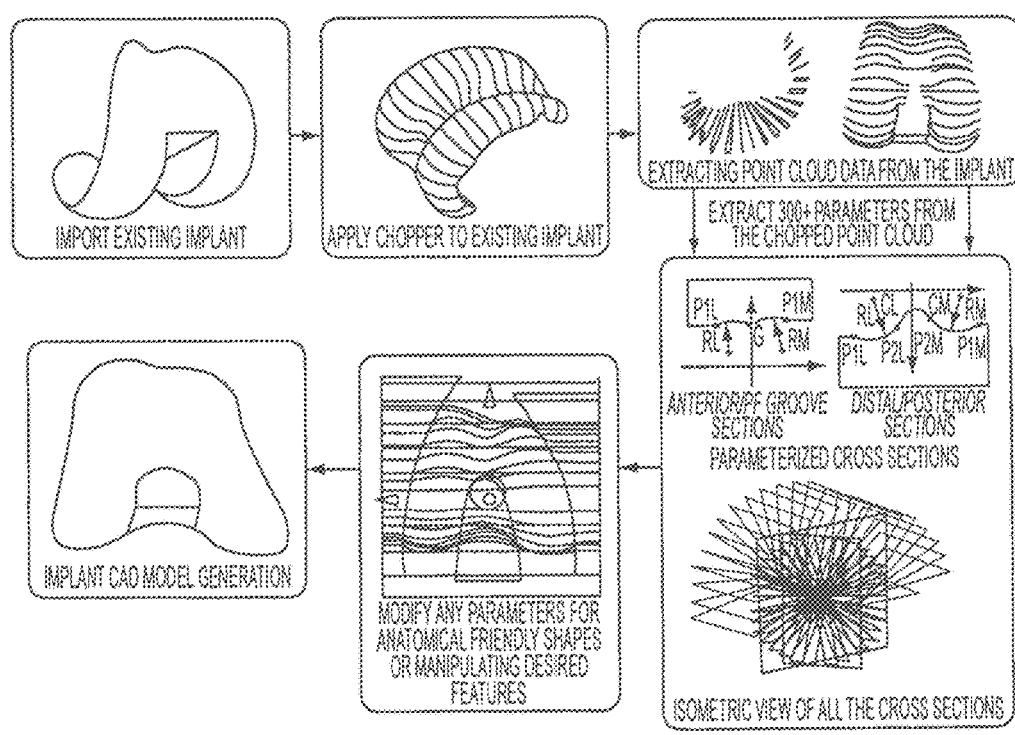
FIG. 64 is an exemplary process flow diagram for updating existing legacy implant systems with anatomical friendly templates.

Referring to FIG. 64, an exemplary flow chart outlines how implant templates generated from the clusters that best fit the population can also be used to update existing legacy systems to ensure conformity with the patient's anatomical trends. This process involves importing a CAD model of an existing implant system and transforming it to same parameterization space as the anatomical templates. This process includes generating a set of three dimensional contours around the implant mid axis. These contours are used to generate a set of constraints in same manner as the anatomical templates. Once the implant is parameterized just as are the templates, the templates parameter values are used to update the parameterized implant features. These parameterized implant features include, but are not limited to, patellar groove curvature, condylar curvature, AP height, and ML width.

Figure 65:
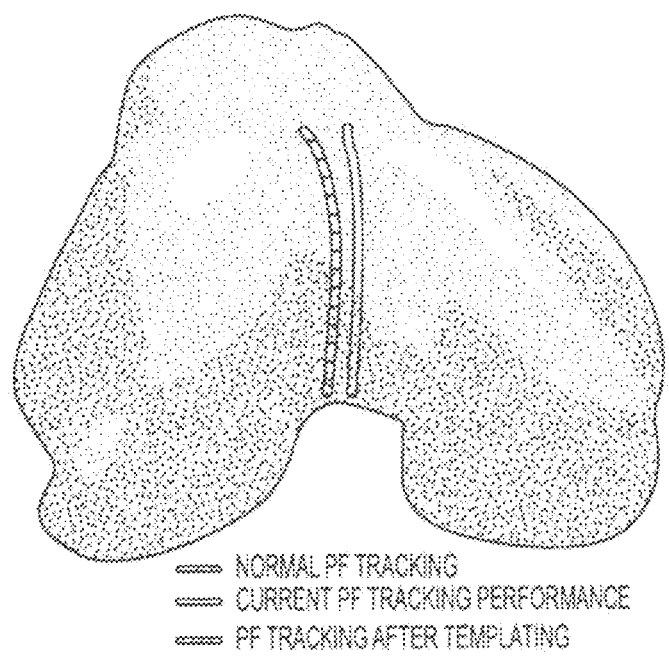
FIG. 65 is a depiction of an updated existing legacy implant system that incorporates a more anatomically accurate patellar groove.

FIG. 65 shows how anatomical friendly templates can be used to update existing implant families to create an implant that mimics an anatomical patellar groove.

Figure 66A:
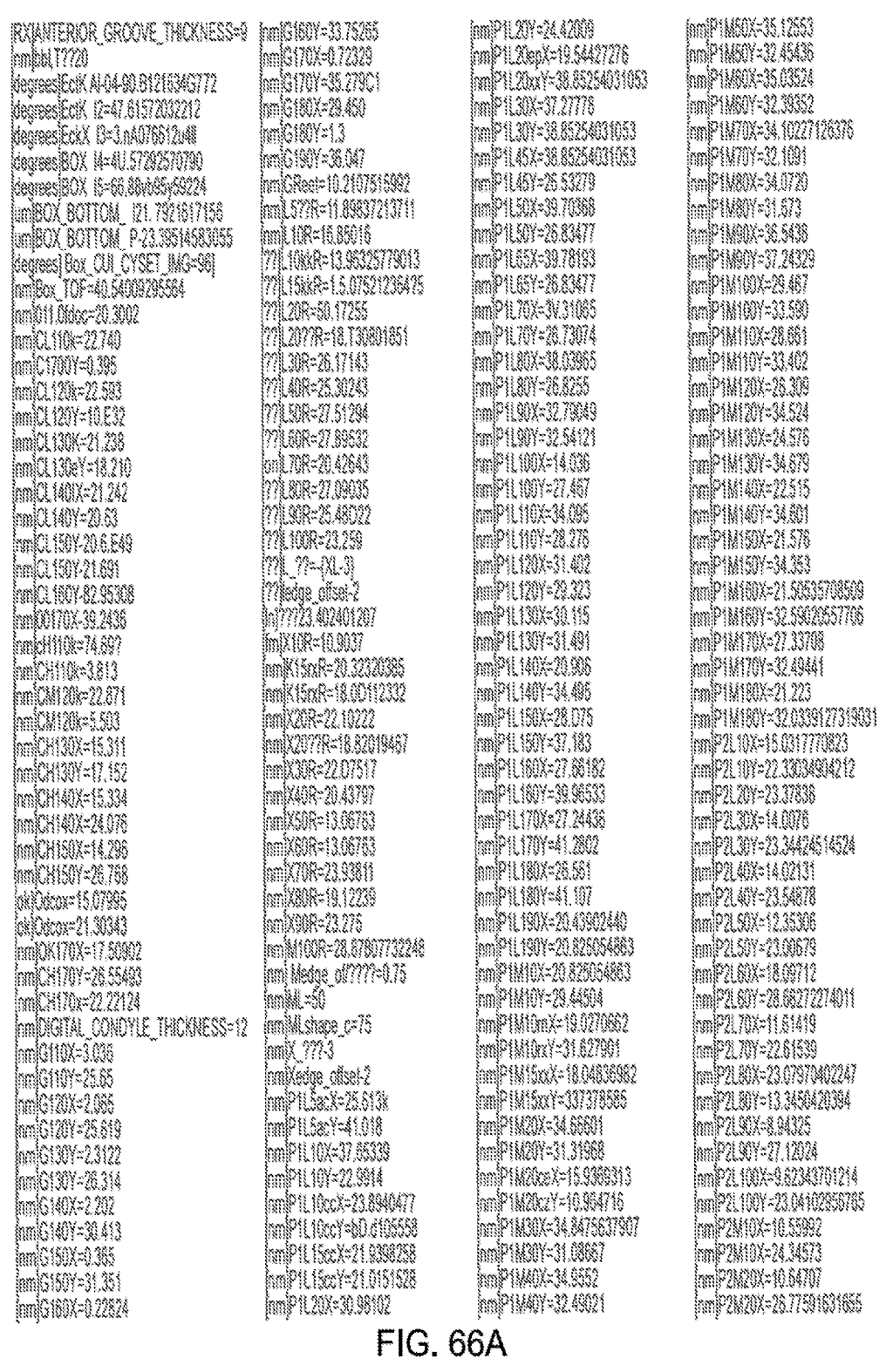
Figure 67:
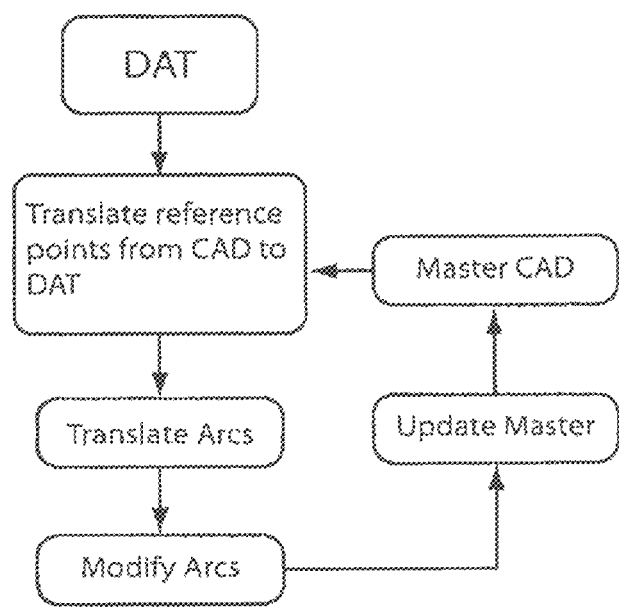
FIG. 67 is an exemplary flow chart describing a process of automatically updating the template parameters and generating an implant CAD.

Referring to FIGS. 66A-66B and 67, an exemplary parametric femoral CAD model consists of 300+ parameters. The CAD model is defined by cross sections around the TEA axis at 10 degrees increment. The parameters define specific points and curvatures of each cross section. The patella-femoral section of the implant is defined by three points from the medial, lateral, and groove curvatures along with 3 radii, as has been previously discussed. As for the condylar cross sections, the medial side and lateral side are defined by two points and a single radius. Shaping information is inherent within the cross-sections in order to create a full implant CAD model automatically.

Figure 68:
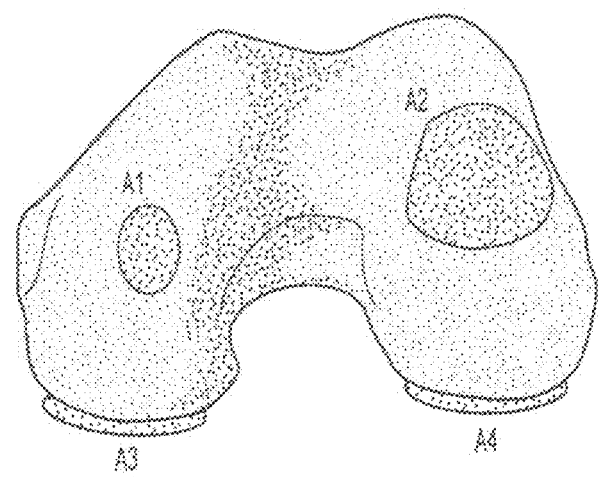
FIG. 68 is a distal femur shown with corresponding contact areas that are highlighted.
Figure 69:
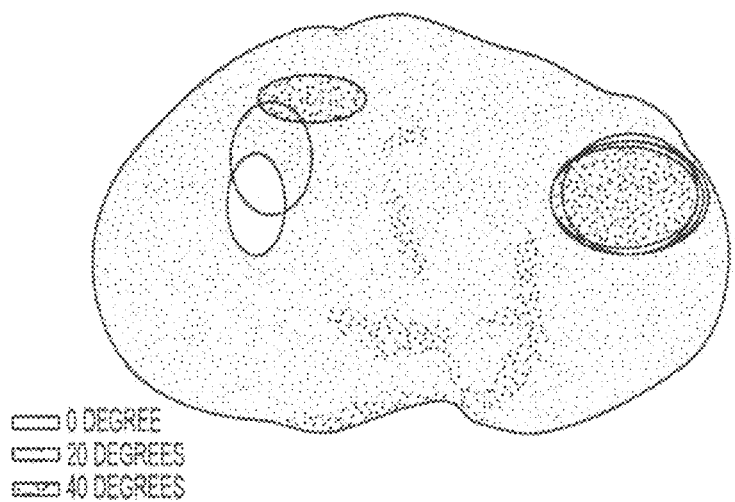
FIG. 69 is a proximal tibia shown with corresponding contact areas that are highlighted for between 0-40 degrees of knee flexion.
Figure 70:
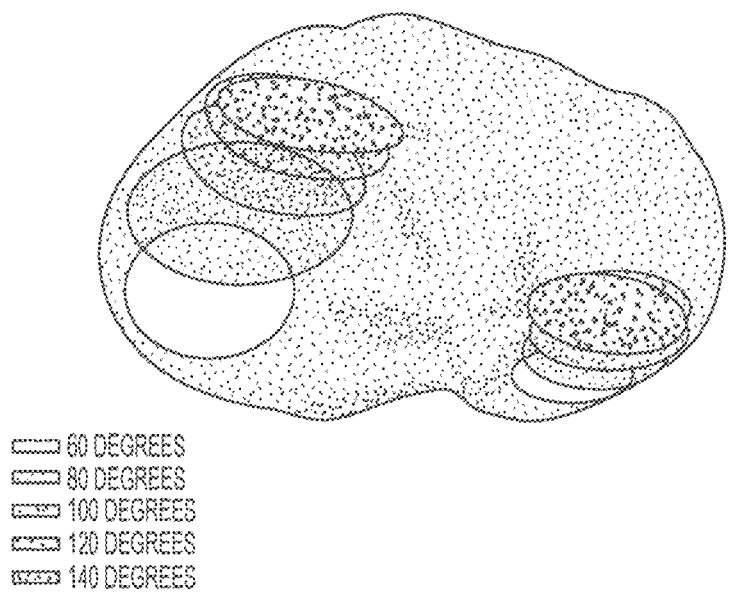
FIG. 70 is a proximal tibia shown with corresponding contact areas that are highlighted for between 60-140 degrees of knee flexion.

Referring to FIG. 68-70, in order to design a functional implant that best mimics the normal knee motion, the full range of the femur relative to the tibia should be completely characterized. To achieve this goal, a set of anatomical areas are localized on the femur and projected on the tibia during the full range of motion. First, the most distal area on the medial side of the femur was localized, which is the area of contact between the femur and tibia in case of full extension (A1) (see FIG. 69). The second area is the most distal area of the lateral condyle (A2), while the third area is the most posterior area of the medial condyle (A3) and the fourth area is the most posterior area of the lateral condyle (A4) (see FIG. 70). During the full range of motion, each of the areas on the femur was projected on the tibia to characterize the motion of these areas relative to the tibial plateau surface. A distinct motion pattern is observed on the medial side where area A1 moves anteriorly until 40 degrees flexion and then disengages from any contact with the tibia surface. At the same time after 40 degrees, the area A3 starts to move anteriorly while performing axial rotation tracking. On the lateral side, the area A2 moves anteriorly with less magnitude compared to A1 until 40 degrees flexion, where it disengages in a similar fashion as A1. At the same time, area A4 comes in contact with and moves anteriorly in a smaller area compared to area A1.

Referring to FIGS. 68-72, in order to achieve the normal motion pattern with a functional PS implant, the design of both the femoral implant curvature and the polyethylene component should be modified to provide a more natural motion. In addition, modifying the cam location on the polyethylene component provides constraint for the femur motion and allows for more axial rotation (see FIG. 71). None of the existing functional implants is operative to provide the same axial rotation as is observed in the normal knee. When a PS implant (see, e.g., FIG. 72) was implanted and thereafter X-ray fluoroscopy studies were carried out to observe the location of the femoral component relative to the cam, it was observed that the cam position intruded into the femoral implant, thereby implying that the cam location does not allow for sufficient axial rotation. In order to improve the axial rotation of the implant joint, the cam position was modified to tilt laterally according to the loci on the medial side. This modification allowed for a better range of axial rotation, which more closely approximated the normal range of motion of a natural knee joint.

Figure 71:
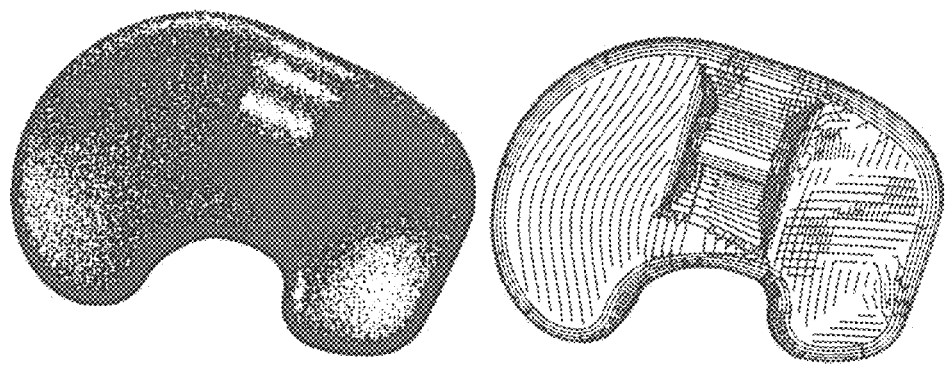
FIG. 71 are overhead views of a tibia tray insert having been modified or redesigned to simulate or approximate normal knee kinematics.
Figure 72:
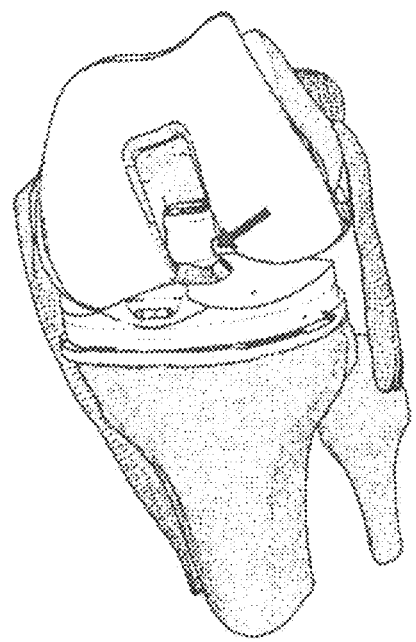
FIG. 72 is a conventional PS knee implant having limited axial rotation.

As seen in FIGS. 69 and 70, the lateral side of the tibia has two distinct loci. The lateral curvatures of the PS polyethylene in FIG. 71 are designed to accommodate such unique conditions. During the flexion from 0 to 40 degrees, the anterior portion of the polyethylene component is defined by four sets of curvatures. This geometry also angles to prevent excessive anterior sliding of the femoral component during these flexion angles. The posterior portion of the polyethylene component is also defined by four sets of curvatures, which engage the lateral condyle from 60 to 140 degrees of flexion. This portion is designed to be flatter to provide smoother motion and prevent impingements. The medial side has one set of curvature that is shaped as a deep dish for the rolling motion during the 60 to 140 degrees of flexion. A second set of curvatures introduce a unique track that first follow the loci from 60 to 120 degrees of flexion and blends into the loci from 0 to 40 degrees of flexion, which allows for a smooth transition between the two loci tracks.

Figure 73:
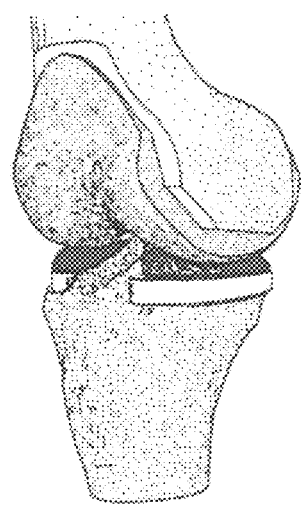
FIG. 73 is an elevated perspective view of an exemplary knee prosthesis designed in accordance with the instant disclosure that provides for retention of the anterior cruciate ligament.
Figure 74:
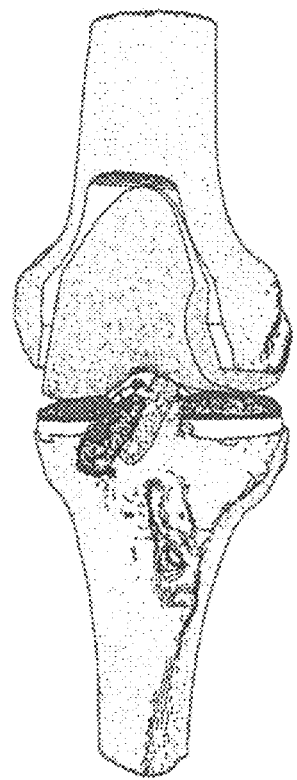
FIG. 74 is a frontal view of an exemplary knee prosthesis designed in accordance with the instant disclosure for use after an anterior cruciate ligament revision surgical procedure.

Referring to FIGS. 73-74 and Table 3, in order to design anatomically friendly bicruicate, ACL, and PCL implants, the location of the PCL and the ACL should be studied as the knee joint is taken through its range of motion. A statistical atlas was utilized to localize and propagate the location of insertions of the ACL and the PCL across an entire population. Both the ACL and PCL were deformed by taking the knee joint through a range of motion in order to map the change in shape and length of the ligament during range of motion. Table 3 highlights the differences in length of the ACL and the PCL as percentage of the ACL length. Using this data, an implant may be designed to accommodate retention of either the PCL or the ACL or both the ACL and PCL.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A system for generating a patient-specific implant, the system comprising:
    a means for generating a three-dimensional electronic representation of a human anatomical feature including size and curvature features matching the human anatomical feature;
    a means for selecting a virtual implant template from a database of virtual implant templates generated by a means for generating a series of the virtual implant templates;
    a means for designing a patient-specific prosthetic implant to imitate the size and curvature features based at least in part on the selected virtual implant template; and
    a means for virtually testing fit of the patient-specific prosthetic implant using the three-dimensional electronic representation of the human anatomical feature.

2. The system of claim 1, further comprising the means for generating the series of the virtual implant templates, where the means for generating the series of the virtual implant templates further comprises:
    a means for generating a plurality of electronic three-dimensional models representing said human anatomical feature across a population of humans, the plurality of electronic three-dimensional models in the database being grouped together;
    a means for associating each of the plurality of models in the database with at least one characteristic selected from the group consisting of: age, race, and gender; and
    a means for designing said plurality of virtual implant templates, where each of the plurality of virtual implant templates is generic to at least a portion of the population of humans for which electronic three-dimensional models were generated.

3. The system of claim 2, wherein the means for designing includes a means for incorporating a size and/or a contour that approximates a mean size and/or a mean contour, respectively, of at least a portion of the population of humans.

4. The system of claim 2, further comprising a means for virtually test fitting at least one of the plurality of virtual implant templates to at least one of the plurality of electronic three-dimensional models.

5. The system of claim 2, further comprising a means for measuring, for at least two of the plurality of electronic three-dimensional models, at least one topography selected from the group consisting of: a medial condyle camming surface topography, a lateral condyle surface topography, and a trochlear groove topography.

6. The system of claim 2, further comprising a means for sweeping the selected virtual implant template, after associating each of the plurality of models in the database with the at least one characteristic, to create a smooth articulating surface template.

7. The system of claim 6, further comprising a means for generating a virtual template cutting guide representing cuts to be made to a human bone to adapt the human bone to accept the patient-specific prosthetic implant.

8. The system of claim 7, further comprising a means for merging the virtual template cutting guide and the smooth articulating surface template to generate a patient-specific virtual model, wherein the patient-specific virtual model is used to generate the patient-specific prosthetic implant.

9. The system of claim 7, wherein the means for generating the virtual template cutting guide automatically measures an anterior-to-posterior height and a medial-to-lateral width of the three-dimensional electronic representation of the human anatomical feature.

10. The system of claim 9, further comprising a means for merging the virtual template cutting guide and the smooth articulating surface template to generate a patient-specific virtual model for use by the means for designing to generate the patient-specific prosthetic implant.

11. The system of claim 1, wherein the human anatomical feature is a femur, and the system further comprises:
   a means for generating a shell of the femur from bone mapping,
   a means for generating profiles/points from the shell by sweeping around the bone every ten degrees,
   a means for generating a curve from the profiles/points, and
   a means for matching at least four radii to the curve.

12. The system of claim 1, wherein the size and curvature features include one or more radii of curvature on an outer surface of the human anatomical feature.

13. The system of claim 1, wherein the means for generating the three-dimensional electronic representation of the human anatomical feature further comprises:
   a means for imaging at least a portion of the human anatomical feature, and
   a means for creating a plurality of 2D image slices of the human anatomical feature taken orthogonal to an axis extending through the human anatomical feature, where each of the plurality of 2D image slices includes a bone segment comprising an enclosed boundary corresponding to an exterior of the patient's bone; and
   a means for virtually constructing a 3D image bone shell of at least the portion of the human anatomical feature for which the plurality of 2D image slices were taken.

14. The system of claim 13, wherein the means for virtually constructing a 3D image bone shell includes software configured to recognize the enclosed boundary of each bone segment by using a template 3D image bone shell that is not patient-specific, wherein the 3D image bone shell depicts a current state of the patient's human anatomical feature.

15. The system of claim 13, wherein the means for imaging comprises a magnetic resonance imaging device and/or a computed tomography device.

16. The system of claim 13, wherein the human anatomical feature comprises at least one bone selected from the group consisting of: a femur, a tibia, and a humerus.

17. The system of claim 13, further comprising means for generating a 3D image surgical jig configured to mate with the 3D image bone shell, wherein the 3D image surgical jig includes topographical features customized to the exterior features of the 3D image bone shell, and the means for generating a 3D image surgical jig includes a software component.

18. The system of claim 17, wherein the software component is configured to output an instruction file for fabricating a surgical jig having tangible topographical features of the 3D image surgical jig.

19. The system of claim 13, further comprising a means for virtually constructing a 3D image cartilage shell representing at least a portion of a patient's cartilage using the plurality of 2D image slices of the human anatomical feature, wherein the means for virtually constructing the 3D image cartilage shell includes software configured to recognize an outline of cartilage appearing in a 2D image slice.

20. The system of claim 1, wherein the human anatomical feature is a bone and the curvature features include a camming surface of bone, the system further comprising a means for identifying a plurality of radii of curvature on the camming surface of the bone.

21. The system of claim 20, wherein the bone is a femoral component of a knee joint, the camming surface includes an anterior-to-distal-to-posterior surface of the medial or lateral condyle, and the means for identifying is configured to identify at least three radii of curvature on the camming surface of the femoral component that are obliquely angled to a medial-lateral direction of the femoral component.

22. The system of claim 20, wherein the bone is a femoral component of a knee joint having a trochlear groove surface that includes an anterior-to-distal surface incorporating at least two radii of curvature obtusely angled to a medial-lateral direction of the femoral component.

23. The system of claim 20, wherein the bone is a femoral component of a knee joint having a trochlear groove surface that includes a medial-to-lateral surface incorporating at least two radii of curvature parallel to a medial-lateral direction of the femoral component.

24. The system of claim 1, further comprising a means for physically forming the patient-specific prosthetic implant using the selected one of the virtual implant templates.

* * * * *